(12) United States Patent
Hubschwerlen et al.

(10) Patent No.: US 8,349,828 B2
(45) Date of Patent: Jan. 8, 2013

(54) AZATRICYCLIC ANTIBIOTIC COMPOUNDS

(75) Inventors: Christian Hubschwerlen, Durmenach (FR); Georg Rueedi, Allschwil (CH); Jean-Philippe Surivet, Kembs (FR); Cornelia Zumbrunn-Acklin, Basel (CH)

(73) Assignee: Actelion Pharmaceuticals Ltd., Allchwil (CH)

( * ) Notice: Subject to any disclaimer, the term of this patent is extended or adjusted under 35 U.S.C. 154(b) by 87 days.

(21) Appl. No.: 12/918,749

(22) PCT Filed: Feb. 19, 2009

(86) PCT No.: PCT/IB2009/050675
§ 371 (c)(1),
(2), (4) Date: Aug. 20, 2010

(87) PCT Pub. No.: WO2009/104147
PCT Pub. Date: Aug. 27, 2009

(65) Prior Publication Data
US 2010/0331318 A1      Dec. 30, 2010

(30) Foreign Application Priority Data

Feb. 20, 2008   (WO) .................. PCT/IB2008/050603
Oct. 3, 2008    (WO) .................. PCT/IB2008/054065

(51) Int. Cl.
   *A61K 31/54*   (2006.01)
   *C07D 279/16*  (2006.01)
(52) U.S. Cl. .................... 514/224.2; 514/230.5; 544/52; 544/105; 546/81
(58) Field of Classification Search ................ 514/224.2, 514/230.5; 544/52, 105; 546/81
See application file for complete search history.

(56) References Cited

U.S. PATENT DOCUMENTS

| | | | |
|---|---|---|---|
| 5,298,518 A | 3/1994 | Miyake et al. | |
| 2007/0060558 A1* | 3/2007 | Sanchez et al. | 514/192 |
| 2010/0113448 A1 | 5/2010 | Itai et al. | |
| 2010/0331318 A1 | 12/2010 | Hubschwerlen et al. | |

FOREIGN PATENT DOCUMENTS

| | | |
|---|---|---|
| EP | 0 106 816 | 4/1984 |
| EP | 0518672 | 12/1992 |
| WO | WO 98/17672 | 4/1998 |
| WO | WO 01/30782 | 5/2001 |
| WO | WO 2004/002490 | 1/2004 |
| WO | WO 2005/019177 | 3/2005 |
| WO | WO 2006/021448 | 3/2006 |
| WO | WO 2006/032466 | 3/2006 |
| WO | WO 2006/046552 | 5/2006 |
| WO | WO 2006/125974 | 11/2006 |
| WO | WO 2007/016610 | 2/2007 |
| WO | WO 2007/071936 | 6/2007 |
| WO | WO 2007/081597 | 7/2007 |
| WO | WO 2007/107965 | 9/2007 |
| WO | WO 2007/115947 | 10/2007 |
| WO | WO 2007/122258 | 11/2007 |
| WO | WO 2007/144423 | 12/2007 |
| WO | WO 2008/003690 | 1/2008 |
| WO | WO 2008/026172 | 3/2008 |
| WO | WO 2008/065198 | 6/2008 |
| WO | WO 2008/078305 | 7/2008 |
| WO | WO 2008/116815 | 10/2008 |
| WO | WO 2008/120003 | 10/2008 |
| WO | WO 2008/125594 | 10/2008 |
| WO | WO 2008/126024 | 10/2008 |
| WO | WO 2008/126034 | 10/2008 |

(Continued)

OTHER PUBLICATIONS

Greene et al., Index of Protective Groups in Organic Synthesis, 3$^{rd}$ Edition (1999).

(Continued)

*Primary Examiner* — Rei-tsang Shiao
(74) *Attorney, Agent, or Firm* — Hunton & Williams LLP

(57) ABSTRACT

The invention relates to antibacterial compounds of formula I

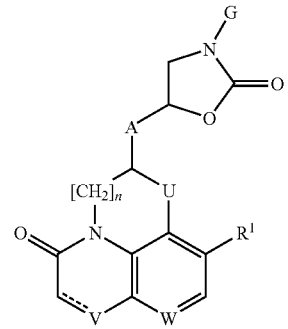

wherein n is 0 or 1; $R^1$ represents H or F; U represents $CH_2$ or, provided n is 1, O or NH; "-----" is a bond or is absent; V represents CH or N when "-----" is a bond, or $CH_2$ or NH when "-----" is absent; W represents CH or N; A represents —$(CH_2)_p$—NH—$(CH_2)_q$— wherein p is 1 and q is 1 or 2 or, provided U represents $CH_2$ and n is 1, p may also be 0 and q is then 2; G represents one of the groups

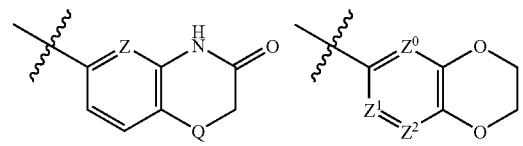

1 wherein Z represents N or CH and Q represents O or S; and $Z^0$, $Z^1$ and $Z^2$ each represent CH, or $Z^0$ and $Z^1$ each represent CH and $Z^2$ represents N, or $Z^0$ represents CH, $Z^1$ represents N and $Z^2$ represents CH or N, or $Z^0$ represents N and $Z^1$ and $Z^2$ each represent CH;
and to salts of such compounds.

22 Claims, No Drawings

FOREIGN PATENT DOCUMENTS

| | | |
|---|---|---|
| WO | WO 2008/128942 | 10/2008 |
| WO | WO 2008/128953 | 10/2008 |
| WO | WO 2008/128962 | 10/2008 |
| WO | WO 2008/148867 | 12/2008 |
| WO | WO 2008/150827 | 12/2008 |
| WO | WO 2008/152603 | 12/2008 |
| WO | WO 2009/000745 | 12/2008 |
| WO | WO 2009/077989 | 6/2009 |
| WO | WO 2009/087153 | 7/2009 |
| WO | WO 2009/104147 | 8/2009 |
| WO | WO 2009/104159 | 8/2009 |

OTHER PUBLICATIONS

Benz, Comprehensive Organic Synthesis, B.M. Trost, 1. Fleming, Eds; Pergamon Press: New York, vol. 6, pp. 381-417 (1991).
Selwood et al., Bioorganic & Medicinal Chemistry Letters, vol. 6, No. 8, pp. 991-994 (1996).
Larock, Comprehensive Organic Transformations, A guide to Functional Group Preparations; 2nd Edition, Wiley-VC; New York, Chichester, Weinheim, Brisbane, Singapore, Toronto, Section: nitriles, carboxylic acids and derivatives, pp. 1941-1949 (1999).
Larock, Comprehensive Organic Transformations, A guide to Functional Group Preparations; 2nd Edition, Wiley-VC; New York, Chichester, Weinheim, Brisbane, Singapore, Toronto, Section: Amines, pp. 1057-1087 (1999).
Abdel-Megeid et al., Egyptian Journal of Chemistry, vol. 20, No. 5, pp. 427-439 (1977).
Svetlik, Journal of Organic Chemistry, vol. 55, pp. 4740-4744 (1990).
Kumar et al., Journal of Organic Chemistry, vol. 59, pp. 4760-4764 (1994).
Liu et al., Journal of Organic Chemistry, vol. 70, pp. 2847-2850 (2005).
Chang et al., Journal of Medicinal Chemistry, vol. 36, pp. 2558-2568 (1993).
Bravo et al., Organic Letters, vol. 5, No. 12, pp. 2123-2126 (2003).
Bartoli et al., Organic Letters, vol. 6, No. 22, pp. 3973-3975 (2004).
Andreou et al., Organic Letters, vol. 7, No. 19, pp. 4083-4086 (2005).
Bartoli et al., Organic Letters, vol. 7, No. 10, pp. 1983-1985 (2005).
International Search Report for International Application No. PCT/IB2009/054357, mailed Jan. 15, 2010.
Written Opinion for International Application No. PCT/IB2009/054357, mailed Jan. 15, 2010.
Albert et al., Journal of Organic Chemistry, vol. 73, pp. 1093-1098 (2008).
Bal et al., Tetrahedron, vol. 37 pp. 2091-2096 (1981).
Brickner, Current Pharmaceutical Design, vol. 2, pp. 175-194 (1996).
Cha et al., Chemical Reviews, vol. 95, vol. 6, pp. 1761-1795 (1995).
Chen et al., Organic Letters, vol. 8, No. 24, pp. 5609-5612 (2006).
Curran et al., Tetrahedron, vol. 49, No. 22, pp. 4841-4858 (1993).
Dess et al., Journal of Organic Chemistry, vol. 48, pp. 4155-4156 (1983).
Fatiadi, Synthesis, pp. 85-127 (1987).
Gould, International Journal Pharmaceutics, vol. 33, pp. 201-217 (1986).
Greene et al., Protecting Groups in Organic Synthesis, 3rd Edition, pp. 23-147, particularly 133-139 and 142-143 (1999).
Greene et al., Protecting Groups in Organic Synthesis, 3rd Edition, pp. 494-653 (1999).
Johannes et al, Organic Letters, vol. 7, No. 18, pp. 3997-4000 (2005).
Kolb et al., Chemical Reviews, vol. 94, vol. 8, pp. 2483-2547 (1994).
Larock, Comprehensive Organic Transformations, A guide to Functional Group Preparations 2nd Edition, Wiley-VC; New York Chichester, Weinheim, Brisbane, Singapore, Toronto, Section Amines, p. 779-784 (1999).
Larock, Comprehensive Organic Transformations. A guide to Functionnal Group Preparations; 2nd Edition, Wiley-VC; New York, Chichester, Weinheim, Brisbane, Singapore, Toronto, Section Nitriles, Carboxylic Acids and Derivatives, pp. 1646-1648 (1999).
Larock, Comprehensive Organic Transformations. A guide to Functional Group Preparations, 2nd Edition, Wiley-VC; New York, Chichester, Weinheim, Brisbane, Singapore, Toronto, 1999. Section Nitriles, Carboxylic Acids and Derivatives, pp. 1653-1655 (1999).
Larock, Comprehensive Organic Transformations. A Guide to Functional Group Preparations, 2nd Edition, Wiley-VC; New York, Chichester, Weinheim, Brisbane, Singapore, Toronto, Section Aldehydes and Ketones, pp. 1235-1236 and 1238-1246 (1999).
Mancuso et al., Journal of Organic Chemistry, vol. 43, pp. 2480-2482 (1978).
Mitsunobu, Synthesis, vol. 1, pp. 1-28 (1981).
Roma et al., Heterocycles, vol. 25, No. 1, pp. 329-332 (1987).
Schaus et al., Journal of the American Chemical Society, vol. 124, pp. 1307-1315 (2002).
Shi et al., Accounts of Chemical Research, 37, pp. 488-496 (2004).
Talbot et al., Clinical Infectious Diseases, vol. 42, pp. 657-668 (2006).
Tokunaga et al., Science, vol. 277, pp. 936-938 (1997).
Unknown, Index of Remington—The Science and Practice of Pharmacy, "Pharmaceutical Manufacturing," 21st Edition, Part 5, (published by Lippincott Williams & Wilkins) (2005).
Vanrheenen et al., Tetrahedron Letters, vol. 23, pp. 1973-1976 (1976).
Vourloumis et al., Tetrahedron Letters, vol. 44, No. 14, pp. 2807-2811 (2003).
Yin et al., Organic Letters, vol. 2, No. 8, pp. 1101-1104 (2000).
Zaragoza et al., Journal of Medicinal Chemistry, vol. 48, pp. 306 (2005).
International Search Report for International Application No. PCT/IB2009/050675 mailed Sep. 17, 2009.

\* cited by examiner

AZATRICYCLIC ANTIBIOTIC COMPOUNDS

CROSS-REFERENCE TO RELATED APPLICATIONS

This application is the national phase application of PCT/IB2009/050675, filed Feb. 19, 2009, which claims the benefit of PCT/IB2008/050603, filed Feb. 20, 2008 and PCT/IB2008/054065, filed Oct. 3, 2008, the contents of all of which are hereby incorporated by reference as if fully set forth herein.

FIELD OF THE INVENTION

The present invention concerns novel azatricyclic antibiotic compounds, a pharmaceutical antibacterial composition containing them and the use of these compounds in the manufacture of a medicament for the treatment of infections (e.g. bacterial infections). These compounds are useful antimicrobial agents effective against a variety of human and veterinary pathogens including among others Gram-positive and Gram-negative aerobic and anaerobic bacteria and mycobacteria.

BACKGROUND OF THE INVENTION

The intensive use of antibiotics has exerted a selective evolutionary pressure on microorganisms to produce genetically based resistance mechanisms. Modern medicine and socio-economic behaviour exacerbate the problem of resistance development by creating slow growth situations for pathogenic microbes, e.g. in artificial joints, and by supporting long-term host reservoirs, e.g. in immuno-compromised patients.

In hospital settings, an increasing number of strains of *Staphylococcus aureus*, *Streptococcus pneumoniae*, *Enterococcus* spp., and *Pseudomonas aeruginosa*, major sources of infections, are becoming multi-drug resistant and therefore difficult if not impossible to treat:
- *S. aureus* is resistant to β-lactams, quinolones and now even to vancomycin;
- *S. pneumoniae* is becoming resistant to penicillin or quinolone antibiotics and even to new macrolides;
- Enteroccocci are quinolone and vancomycin resistant and β-lactam antibiotics are inefficacious against these strains;
- Enterobacteriacea are cephalosporin and quinolone resistant;
- *P. aeruginosa* are β-lactam and quinolone resistant.

Furthermore, the incidence of multi-drug-resistant Gram-negative strains such as Enterobacteriacea and *Pseudomonas aeruginosa*, is steadily increasing and new emerging organisms like *Acinetobacter* spp., which have been selected during therapy with the currently used antibiotics, are becoming a real problem in hospital settings. Therefore, there is a high medical need for new antibacterial agents which overcome multidrug-resistant Gram-negative bacilli such as *A. baumannii*, ESBL-producing *E. coli* and *Klebsiella* species and *Pseudomonas aeruginosa* (Clinical Infectious Diseases (2006), 42, 657-668).

In addition, microorganisms that are causing persistent infections are increasingly being recognized as causative agents or cofactors of severe chronic diseases like peptic ulcers or heart diseases.

Azatricyclic antibiotic compounds have already been described in WO 2007/071936 and WO 2007/122258 (disclosing 3-oxo-1,2-dihydro-3H-2a,6-diaza-acenaphthylene-1-methyl derivatives), WO 2007/081597 (disclosing 4-oxo-1,2-dihydro-4H-pyrrolo[3,2,1-ij]quinoline-1-methyl derivatives), WO 2007/115947 (disclosing 3-oxo-5,6-dihydro-3H-pyrrolo[1,2,3-de]quinoxaline-6-methyl derivatives) and WO 2008/003690 (disclosing notably 1-(7-oxo-5,6,9a,9b-tetrahydro-4H,7H-1,6a-diaza-phenalen-5-yl)-piperidine-4-yl and 1-(5-oxo-2,3,7a,10b-tetrahydro-1H,5H-pyrido[3,2,1-ij]quinolin-2-yl)-piperidine-4-yl derivatives). In addition, WO 2008/116815, WO 2008/125594, WO 2008/120003, WO 2008/128953, WO 2008/128962 and WO 2009/000745 disclose further azatricyclic antibiotic compounds.

The applicant has now found a new family of azatricyclic antibiotic compounds corresponding to the formula I described hereafter.

BRIEF SUMMARY OF THE INVENTION

Various embodiments of the invention are presented hereafter:

i) The invention firstly relates to compounds of formula I wherein
n is 0 or 1;
$R^1$ represents H or F;
U represents $CH_2$ or, provided n is 1, O or NH;
"-----" is a bond or is absent;
V represents CH or N when "-----" is a bond, or V represents $CH_2$ or NH when "-----" is absent (and notably CH when "-----" is a bond or $CH_2$ when "-----" is absent);
W represents CH or N;
A is —$(CH_2)_p$—NH—$(CH_2)_q$— wherein p is 1 and q is 1 or 2 or, provided U represents $CH_2$ and n is 1, p may also be 0 and q is then 2;
G represents one of the groups $G^1$ and $G^2$ represented below wherein Z represents N or CH and Q represents O or S; and $Z^0$, $Z^1$ and $Z^2$ each represent CH, or $Z^0$ and $Z^1$ each represent CH and $Z^2$ represents N, or $Z^0$ represents CH, $Z^1$ represents N and $Z^2$ represents CH or N, or $Z^0$ represents N and $Z^1$ and $Z^2$ each represent CH;

and to salts (in particular pharmaceutically acceptable salts) of compounds of formula I.

DETAILED DESCRIPTION OF PREFERRED EMBODIMENTS

The compounds of formula I may contain one or more stereogenic or asymmetric centers, such as one or more asymmetric carbon atoms. The compounds of formula I may thus be present as mixtures of stereoisomers or diastereomers or preferably as pure stereoisomers. Mixtures of stereoisomers or diastereomers may be separated in a manner known to a person skilled in the art.

The following paragraphs provide definitions of the various chemical moieties for the compounds according to the invention and are intended to apply uniformly throughout the specification and claims, unless an otherwise expressly set out definition provides a broader or narrower definition:

- The term "alkyl", used alone or in combination, refers to a saturated straight or branched chain alkyl group containing from one to four carbon atoms. Representative examples of alkyl groups include methyl, ethyl, propyl, iso-propyl, n-butyl, iso-butyl, sec-butyl and tent-butyl. The term "$(C_1$-$C_x)$alkyl" (x being an integer) refers to a straight or branched chain alkyl group containing 1 to x carbon atoms.
- The term "alkoxy", used alone or in combination, refers to a saturated straight or branched chain alkoxy group containing from one to four carbon atoms. Representative examples of alkoxy groups include methoxy, ethoxy, propoxy, iso-propoxy, n-butoxy, iso-butoxy, sec-butoxy and tert-butoxy. The term "$(C_1$-$C_x)$alkoxy" refers to a straight or branched chain alkoxy group containing 1 to x carbon atoms.
- The term "halogen" refers to fluorine, chlorine, bromine or iodine, preferably to fluorine or chlorine.

In this text, a bond interrupted by a wavy line shows a point of attachment of the radical drawn to the rest of the molecule. For example, the radical drawn below

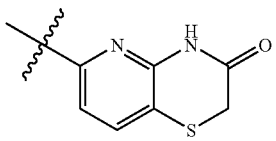 [SMILES: *c1ccc2c(n1)NC(=O)CS2]

is the 3-oxo-3,4-dihydro-2H-pyrido[3,2-b][1,4]thiazine-6-yl group.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

Moreover, the groups of the divalent radical A are always represented such that the part represented on the left (i.e. the radical —$(CH_2)_p$— is attached to the tricyclic radical of the formula I, $I_{P1}$, $I_{CE}$ or $I_{CEP1}$ and that the part represented on the right (i.e. the group —$(CH_2)_q$—) is attached to the radical G of the formula I, $I_{P1}$, $I_{CE}$ or $I_{CEP1}$.

Besides, the term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 0.5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

ii) The invention thus relates notably to compounds of formula I as defined in embodiment i) that are also compounds of formula $I_{P1}$

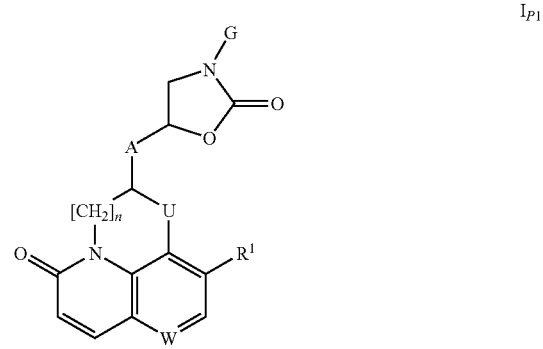

$I_{P1}$ wherein n is 0 or 1;

$R^1$ represents H or F;

U represents $CH_2$ or, provided n is 1, O;

W represents CH or N;

A is —$(CH_2)_p$—NH—$(CH_2)_q$— wherein p is 1 and q is 1 or 2 or, provided U represents $CH_2$ and n is 1, p may also be 0 and q is then 2;

G represents one of the groups $G^1$ and $G^{2'}$ represented below

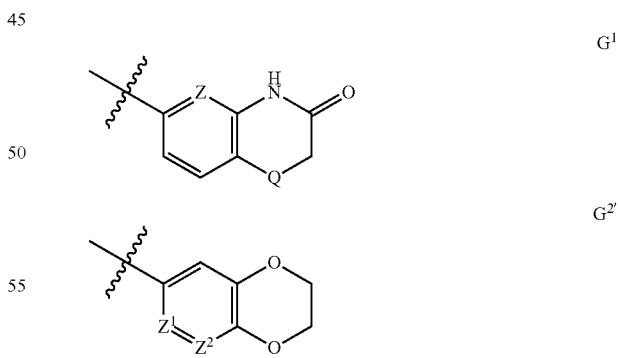

wherein Z, $Z^1$ and $Z^2$ each independently represent N or CH and Q represents O or S;

and to salts (in particular pharmaceutically acceptable salts) of compounds of formula $I_{P1}$.

iii) In particular, the invention relates to compounds of formula I as defined in embodiment i) that are also compounds of formula $I_{CEP2}$

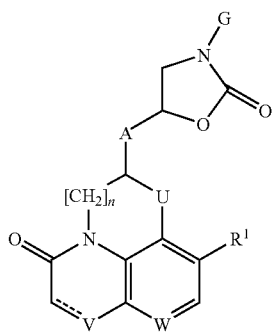

wherein
n is 0 or 1;
R¹ represents H or F;
U represents $CH_2$, or, provided n is 1, O;
"-----" is a bond or is absent;
V represents CH when "-----" is a bond or $CH_2$ when "-----" is absent;
W represents CH or N;
A is —$(CH_2)_p$—NH—$(CH_2)_q$— wherein p is 1 and q is 1 or 2 or, provided U represents $CH_2$ and
n is 1, p may also be 0 and q is then 2;
G represents one of the groups $G^{1''}$ and $G^{2''}$ represented below

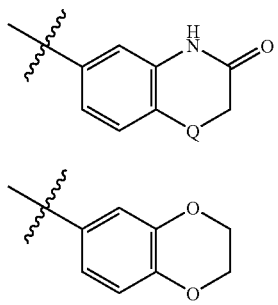

wherein Q represents O or S;
and to salts (in particular pharmaceutically acceptable salts) of compounds of formula $I_{CEP2}$.

iv) The invention furthermore relates notably to compounds of formula $I_{P1}$ as defined in embodiment ii) that are also compounds of formula $I_{CEP1}$

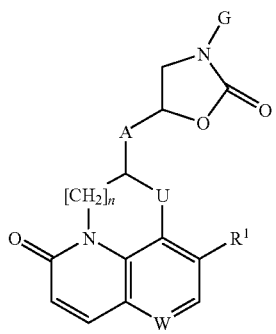

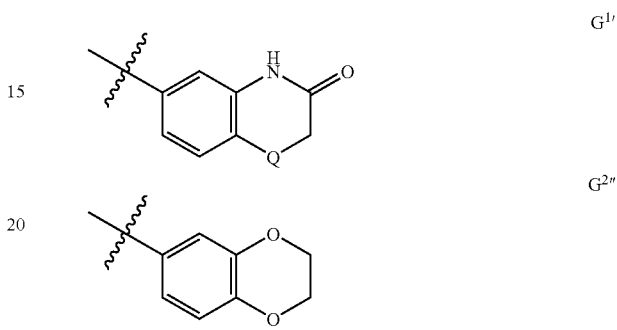

wherein
n is 0 or 1;
R¹ represents H or F;
U represents $CH_2$, or, provided n is 1, O;
W represents CH or N;
A is —$(CH_2)_p$—NH—$(CH_2)_q$— wherein p is 1 and q is 1 or 2 or, provided U represents $CH_2$ and
n is 1, p may also be 0 and q is then 2;
G represents one of the groups $G^{1''}$ and $G^{2''}$ represented below wherein Q represents O or S;
and to salts (in particular pharmaceutically acceptable salts) of compounds of formula $I_{CE}$.

v) According to a main embodiment of this invention, the compounds of formula I as defined in one of embodiments i) to iv) above or their salts (among which the pharmaceutically acceptable salts will be preferred) will be such that W represents CH.

vi) According to another main embodiment of this invention, the compounds of formula I as defined in one of embodiments i) to iv) above or their salts (among which the pharmaceutically acceptable salts will be preferred) will be such that W represents N.

vii) According to a particular variant of this invention, the compounds of formula I as defined in one of embodiments i) to vi) above or their salts (among which the pharmaceutically acceptable salts will be preferred) will be such that R¹ represents H.

viii) According to another particular variant of this invention, the compounds of formula I as defined in one of embodiments i) to vi) above or their salts (among which the pharmaceutically acceptable salts will be preferred) will be such that R¹ represents F.

ix) Another particular embodiment of this invention relates to the compounds of formula I as defined in one of embodiments i) to viii) above or their salts (among which the pharmaceutically acceptable salts will be preferred) wherein U represents O.

x) Yet another particular embodiment of this invention relates to the compounds of formula I as defined in one of embodiments i) or iii) above, optionally with the additional technical features of one of embodiments v) to viii), or their salts (among which the pharmaceutically acceptable salts will be preferred) wherein U represents NH.

xi) Yet another particular embodiment of this invention relates to the compounds of formula I as defined in one of embodiments i) to viii) above or their salts (among which the pharmaceutically acceptable salts will be preferred) wherein U represents $CH_2$.

xii) According to yet another particular variant of this invention, the compounds of formula I as defined in one of embodiments i) to xi) above or their salts (among which the pharmaceutically acceptable salts will be preferred) will be such that A represents —CH$_2$—NH—CH$_2$— or —CH$_2$—NH—(CH$_2$)$_2$—.

xiii) According to a first subvariant of the particular variant xii) above, the compounds of formula I or their salts (among which the pharmaceutically acceptable salts will be preferred) will be such that A represents —CH$_2$—NH—CH$_2$—.

xiv) According to a second subvariant of the particular variant xii) above, the compounds of formula I or their salts (among which the pharmaceutically acceptable salts will be preferred) will be such that A represents —CH$_2$—NH—(CH$_2$)$_2$—.

xv) According to a further particular variant of this invention, the compounds of formula as defined in one of embodiments i) to viii) or xi) above or their salts (among which the pharmaceutically acceptable salts will be preferred) will be such that A represents —NH—CH$_2$—CH$_2$—.

xvi) According to a further main embodiment of this invention, the compounds of formula I as defined in one of embodiments i) to xv) above or their salts (among which the pharmaceutically acceptable salts will be preferred) will be such that G represents the group G$^1$, or, in the embodiments referring to embodiment iii) or iv), the group G$^{1'}$.

xvii) Preferably, the compounds of formula I according to the main embodiment xvi) or their salts (among which the pharmaceutically acceptable salts will be preferred) will be such that Z, when present, represents CH and Q represents O or S (notably 5).

xviii) According to yet a further main embodiment of this invention, the compounds of formula I as defined in one of embodiments i) to xv) above or their salts (among which the pharmaceutically acceptable salts will be preferred) will be such that G represents the group G$^2$, or, in the embodiments referring to embodiment ii), such that G represents the group G$^{2'}$, or, in the embodiments referring to embodiment iii) or iv), such that G represents the group G$^{2''}$.

xix) Preferably, the compounds of formula I according to the main embodiment xviii) or their salts (among which the pharmaceutically acceptable salts will be preferred) will be such that Z$^1$ and Z$^2$ each represent CH (and in particular such that Z$^1$ and Z$^2$ each represent CH and Z$^0$, when present, also represents CH).

xx) According to yet a further main embodiment of this invention, the compounds of formula I as defined in one of embodiments i) to viii), xi) to xiv) and xvi) to xix) above or their salts (among which the pharmaceutically acceptable salts will be preferred) will be such that n is 0.

xxi) According to yet a further main embodiment of this invention, the compounds of formula I as defined in one of embodiments i) to xix) above or their salts (among which the pharmaceutically acceptable salts will be preferred) will be such that n is 1.

xxii) A further particular embodiment relates to compounds of formula I as defined in embodiment i) or iii) above, optionally with the additional technical features of one of embodiments v) to xxi), or their salts (among which the pharmaceutically acceptable salts will be preferred), wherein V represents CH or N (and preferably CH) and "-----" is a bond.

xxiii) Another particular embodiment relates to compounds of formula I as defined in embodiment i) or iii) above, optionally with the additional technical features of one of embodiments v) to xxi), or their salts (among which the pharmaceutically acceptable salts will be preferred), wherein V represents CH$_2$ or NH (and preferably CH$_2$) and "-----" is absent.

xxiv) According to yet a further main embodiment of this invention, the compounds of formula I as defined in one of embodiments i) to xxiii) above or their salts (among which the pharmaceutically acceptable salts will be preferred) will be such that the stereocenter at position 5 of the oxazolidin-2-one ring is in the (R) configuration.

xxv) According to yet a further main embodiment of this invention, the compounds of formula I as defined in one of embodiments i) to xxiii) above or their salts (among which the pharmaceutically acceptable salts will be preferred) will be such that the stereocenter at position 5 of the oxazolidin-2-one ring is in the (S) configuration.

xxvi) Particularly preferred are the following compounds of formula I as defined in embodiment i):

2-({[(R)-2-oxo-3-(3-oxo-3,4-dihydro-2H-benzo[1,4]thiazin-6-yl)-oxazolidin-5-ylmethyl]-amino}-methyl)-2,3-dihydro-1-oxa-3a,7-diaza-phenalen-4-one;

2-({[(R)-2-oxo-3-(3-oxo-3,4-dihydro-2H-benzo[1,4]oxazin-6-yl)-oxazolidin-5-ylmethyl]-amino}-methyl)-2,3-dihydro-1-oxa-3a,7-diaza-phenalen-4-one;

8-fluoro-6-({[(R)-2-oxo-3-(3-oxo-3,4-dihydro-2H-benzo[1,4]thiazin-6-yl)-oxazolidin-5-ylmethyl]-amino}-methyl)-6,7-dihydro-5H-pyrido[3,2,1-ij]quinolin-3-one;

8-fluoro-6-({[(R)-2-oxo-3-(3-oxo-3,4-dihydro-2H-benzo[1,4]oxazin-6-yl)-oxazolidin-5-ylmethyl]-amino}-methyl)-6,7-dihydro-5H-pyrido[3,2,1-ij]quinolin-3-one;

6-({[(R)-3-(2,3-dihydro-benzo[1,4]dioxin-6-yl)-2-oxo-oxazolidin-5-ylmethyl]-amino}-methyl)-8-fluoro-6,7-dihydro-5H-pyrido[3,2,1-ij]quinolin-3-one;

(R)-9-fluoro-2-({[(R)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one;

8-fluoro-6-{2-[2-oxo-3-(3-oxo-3,4-dihydro-2H-benzo[1,4]thiazin-6-yl)-oxazolidin-5-yl]-ethylamino}-6,7-dihydro-5H-pyrido[3,2,1-ij]quinolin-3-one;

(R)-9-fluoro-2-({[(R)-2-oxo-3-(3-oxo-3,4-dihydro-2H-benzo[1,4]oxazin-6-yl)-oxazolidin-5-ylmethyl]-amino}-methyl)-1,2-dihydro-pyrrolo[3,2,1-ij]quinolin-4-one;

9-fluoro-2-({[(R)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one;

(R)-9-fluoro-2-({2-[2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

2-({[(R)-2-oxo-3-(3-oxo-3,4-dihydro-2H-benzo[1,4]thiazin-6-yl)-oxazolidin-5-ylmethyl]-amino}-methyl)-2,3-dihydro-1-oxa-3a-aza-phenalen-4-one;

9-fluoro-2-({[(R)-2-oxo-3-(3-oxo-3,4-dihydro-2H-benzo[1,4]thiazin-6-yl)-oxazolidin-5-ylmethyl]-amino}-methyl)-2,3-dihydro-1-oxa-3a-aza-phenalen-4-one;

3-fluoro-5-({[(R)-2-oxo-3-(3-oxo-3,4-dihydro-2H-benzo[1,4]thiazin-6-yl)-oxazolidin-5-ylmethyl]-amino}-methyl)-5,6-dihydro-4H-1,6a-diaza-phenalen-7-one;

3-fluoro-5-({[(R)-2-oxo-3-(3-oxo-3,4-dihydro-2H-benzo[1,z]oxazin-6-yl)-oxazolidin-5-ylmethyl]-amino}-methyl)-5,6-dihydro-4H-1,6a-diaza-phenalen-7-one;

3-fluoro-5-({2-[(R)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;

(S)-9-fluoro-2-({[(R)-2-oxo-3-(3-oxo-3,4-dihydro-2H-benzo[1,4]oxazin-6-yl)-oxazolidin-5-ylmethyl]-amino}-methyl)-1,2-dihydro-pyrrolo[3,2,1-ij]quinolin-4-one;

(S)-9-fluoro-2-({2-[(R)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

(R)-9-fluoro-2-({2-[(R)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

(S)-9-fluoro-2-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

(R)-9-fluoro-2-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

9-fluoro-2-({2-[(R)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1-ij]quinolin-4-one;

9-fluoro-2-({2-[(S)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1-ij]quinolin-4-one;

9-fluoro-2-({2-[(R)-2-oxo-3-(3-oxo-3,4-dihydro-2H-benzo[1,4]oxazin-6-yl)-oxazolidin-5-yl]-ethylamino}-methyl)-1,2,5,6-tetrahydro-pyrrolo[3,2,1-ij]quinolin-4-one;

5-({2-[(R)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;

5-({2-[(S)-2-oxo-3-(3-oxo-3,4-dihydro-2H-benzo[1,4]oxazin-6-yl)-oxazolidin-5-yl]-ethylamino}-methyl)-4,5-dihydro-pyrrolo[3,2,1-de][1,5]naphthyridin-7-one;

2-({2-[(R)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

2-({2-[(R)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1-ij]quinolin-4-one;

2-({[(R)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one;

(S)-5-({2-[(S)-2-oxo-3-(3-oxo-3,4-dihydro-2H-benzo[1,4]thiazin-6-yl)-oxazolidin-5-yl]-ethylamino}-methyl)-5,6-dihydro-pyrrolo[1,2,3-de]quinoxalin-3-one;

(S)-5-({[(R)-2-oxo-3-(3-oxo-3,4-dihydro-2H-benzo[1,4]thiazin-6-yl)-oxazolidin-5-ylmethyl]-amino}-methyl)-5,6-dihydro-pyrrolo[1,2,3-de]quinoxalin-3-one;

5-({2-[(S)-2-oxo-3-(3-oxo-3,4-dihydro-2H-pyrido[3,2-b][1,4]oxazin-6-yl)-oxazolidin-5-yl]-ethylamino}-methyl)-5,6-dihydro-pyrrolo[1,2,3-de]quinoxalin-3-one;

as well as the salts (in particular the pharmaceutically acceptable salts) thereof, among which the 24 first compounds and their salts (among which the pharmaceutically acceptable salts will be preferred) constitute a particular embodiment and the 12 first compounds and their salts (among which the pharmaceutically acceptable salts will be preferred) constitute another particular embodiment.

xxvii) Furthermore, the following compounds of formula I as defined in embodiment i) are particularly preferred:

2-(R)-({[(R)-2-oxo-3-(3-oxo-3,4-dihydro-2H-benzo[1,4]thiazin-6-yl)-oxazolidin-5-ylmethyl]-amino}-methyl)-2,3-dihydro-1-oxa-3a,7-diaza-phenalen-4-one;

2-(S)-({[(R)-2-oxo-3-(3-oxo-3,4-dihydro-2H-benzo[1,4]thiazin-6-yl)-oxazolidin-5-ylmethyl]-amino}-methyl)-2,3-dihydro-1-oxa-3a,7-diaza-phenalen-4-one;

2-(R)-({[(R)-2-oxo-3-(3-oxo-3,4-dihydro-2H-benzo[1,4]oxazin-6-yl)-oxazolidin-5-ylmethyl]-amino}-methyl)-2,3-dihydro-1-oxa-3a,7-diaza-phenalen-4-one;

2-(S)-({[(R)-2-oxo-3-(3-oxo-3,4-dihydro-2H-benzo[1,4]oxazin-6-yl)-oxazolidin-5-ylmethyl]-amino}-methyl)-2,3-dihydro-1-oxa-3a,7-diaza-phenalen-4-one;

(6R)-8-fluoro-6-({[(R)-2-oxo-3-(3-oxo-3,4-dihydro-2H-benzo[1,4]thiazin-6-yl)-oxazolidin-5-ylmethyl]-amino}-methyl)-6,7-dihydro-5H-pyrido[3,2,1-ij]quinolin-3-one;

(6S)-8-fluoro-6-({[(R)-2-oxo-3-(3-oxo-3,4-dihydro-2H-benzo[1,4]thiazin-6-yl)-oxazolidin-5-ylmethyl]-amino}-methyl)-6,7-dihydro-5H-pyrido[3,2,1-ij]quinolin-3-one;

(6R)-8-fluoro-6-({[(R)-2-oxo-3-(3-oxo-3,4-dihydro-2H-benzo[1,4]oxazin-6-yl)-oxazolidin-5-ylmethyl]-amino}-methyl)-6,7-dihydro-5H-pyrido[3,2,1-ij]quinolin-3-one;

(6S)-8-fluoro-6-({[(R)-2-oxo-3-(3-oxo-3,4-dihydro-2H-benzo[1,4]oxazin-6-yl)-oxazolidin-5-ylmethyl]-amino}-methyl)-6,7-dihydro-5H-pyrido[3,2,1-ij]quinolin-3-one;

(6R)-6-({[(R)-3-(2,3-dihydro-benzo[1,4]dioxin-6-yl)-2-oxo-oxazolidin-5-ylmethyl]-amino}-methyl)-8-fluoro-6,7-dihydro-5H-pyrido[3,2,1-ij]quinolin-3-one;

(6S)-6-({[(R)-3-(2,3-dihydro-benzo[1,4]dioxin-6-yl)-2-oxo-oxazolidin-5-ylmethyl]-amino}-methyl)-8-fluoro-6,7-dihydro-5H-pyrido[3,2,1-ij]quinolin-3-one;

(R)-9-fluoro-2-({[(R)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one;

(6R)-8-fluoro-6-{2-[(R)-2-oxo-3-(3-oxo-3,4-dihydro-2H-benzo[1,4]thiazin-6-yl)-oxazolidin-5-yl]-ethylamino}-6,7-dihydro-5H-pyrido[3,2,1-ij]quinolin-3-one;

(6R)-8-fluoro-6-{2-[(S)-2-oxo-3-(3-oxo-3,4-dihydro-2H-benzo[1,4]thiazin-6-yl)-oxazolidin-5-yl]-ethylamino}-6,7-dihydro-5H-pyrido[3,2,1-ij]quinolin-3-one;

(6S)-8-fluoro-6-{2-[(R)-2-oxo-3-(3-oxo-3,4-dihydro-2H-benzo[1,4]thiazin-6-yl)-oxazolidin-5-yl]-ethylamino}-6,7-dihydro-5H-pyrido[3,2,1-ij]quinolin-3-one;

(6S)-8-fluoro-6-{2-[(S)-2-oxo-3-(3-oxo-3,4-dihydro-2H-benzo[1,4]thiazin-6-yl)-oxazolidin-5-yl]-ethylamino}-6,7-dihydro-5H-pyrido[3,2,1-ij]quinolin-3-one;

(R)-9-fluoro-2-({[(R)-2-oxo-3-(3-oxo-3,4-dihydro-2H-benzo[1,4]oxazin-6-yl)-oxazolidin-5-ylmethyl]-amino}-methyl)-1,2-dihydro-pyrrolo[3,2,1-ij]quinolin-4-one;

(R)-9-fluoro-2-({[(R)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one;

(S)-9-fluoro-2-({[(R)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one;

(R)-9-fluoro-2-({2-[(R)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

(R)-9-fluoro-2-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

(R)-2-({[(R)-2-oxo-3-(3-oxo-3,4-dihydro-2H-benzo[1,4]thiazin-6-yl)-oxazolidin-5-ylmethyl]-amino}-methyl)-2,3-dihydro-1-oxa-3a-aza-phenalen-4-one;

(S)-2-({[(R)-2-oxo-3-(3-oxo-3,4-dihydro-2H-benzo[1,4]thiazin-6-yl)-oxazolidin-5-ylmethyl]-amino}-methyl)-2,3-dihydro-1-oxa-3a-aza-phenalen-4-one;

(R)-9-fluoro-2-({[(R)-2-oxo-3-(3-oxo-3,4-dihydro-2H-benzo[1,4]thiazin-6-yl)-oxazolidin-5-ylmethyl]-amino}-methyl)-2,3-dihydro-1-oxa-3a-aza-phenalen-4-one;

(S)-9-fluoro-2-({[(R)-2-oxo-3-(3-oxo-3,4-dihydro-2H-benzo[1,4]thiazin-6-yl)-oxazolidin-5-ylmethyl]-amino}-methyl)-2,3-dihydro-1-oxa-3a-aza-phenalen-4-one;

(R)-3-fluoro-5-({[(R)-2-oxo-3-(3-oxo-3,4-dihydro-2H-benzo[1,4]thiazin-6-yl)-oxazolidin-5-ylmethyl]-amino}-methyl)-5,6-dihydro-4H-1,6a-diaza-phenalen-7-one;

(S)-3-fluoro-5-({[(R)-2-oxo-3-(3-oxo-3,4-dihydro-2H-benzo[1,4]thiazin-6-yl)-oxazolidin-5-ylmethyl]-amino}-methyl)-5,6-dihydro-4H-1,6a-diaza-phenalen-7-one;

(R)-3-fluoro-5-({[(R)-2-oxo-3-(3-oxo-3,4-dihydro-2H-benzo[1,4]oxazin-6-yl)-oxazolidin-5-ylmethyl]-amino}-methyl)-5,6-dihydro-4H-1,6a-diaza-phenalen-7-one;

(S)-3-fluoro-5-({[(R)-2-oxo-3-(3-oxo-3,4-dihydro-2H-benzo[1,4]oxazin-6-yl)-oxazolidin-5-ylmethyl]-amino}-methyl)-5,6-dihydro-4H-1,6a-diaza-phenalen-7-one;

(R)-3-fluoro-5-({2-[(R)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;

(S)-3-fluoro-5-({2-[(R)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;

(S)-9-fluoro-2-({[(R)-2-oxo-3-(3-oxo-3,4-dihydro-2H-benzo[1,4]oxazin-6-yl)-oxazolidin-5-ylmethyl]-amino}-methyl)-1,2-dihydro-pyrrolo[3,2,1-ij]quinolin-4-one;

(S)-9-fluoro-2-({2-[(R)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

(R)-9-fluoro-2-({2-[(R)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

(S)-9-fluoro-2-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;
(R)-9-fluoro-2-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;
(R)-9-fluoro-2-({2-[(R)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1-ij]quinolin-4-one;
(S)-9-fluoro-2-({2-[(R)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1-ij]quinolin-4-one;
(R)-9-fluoro-2-({2-[(S)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1-ij]quinolin-4-one;
(S)-9-fluoro-2-({2-[(S)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1-ij]quinolin-4-one;
(R)-9-fluoro-2-({2-[(R)-2-oxo-3-(3-oxo-3,4-dihydro-2H-benzo[1,4]oxazin-6-yl)-oxazolidin-5-yl]-ethylamino}-methyl)-1,2,5,6-tetrahydro-pyrrolo[3,2,1-ij]quinolin-4-one;
(S)-9-fluoro-2-({2-[(R)-2-oxo-3-(3-oxo-3,4-dihydro-2H-benzo[1,4]oxazin-6-yl)-oxazolidin-5-yl]-ethylamino}-methyl)-1,2,5,6-tetrahydro-pyrrolo[3,2,1-ij]quinolin-4-one;
(R)-5-({2-[(R)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;
(S)-5-({2-[(R)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;
(R)-5-({2-[(S)-2-oxo-3-(3-oxo-3,4-dihydro-2H-benzo[1,4]oxazin-6-yl)-oxazolidin-5-yl]-ethylamino}-methyl)-4,5-dihydro-pyrrolo[3,2,1-de][1,5]naphthyridin-7-one;
(S)-5-({2-[(S)-2-oxo-3-(3-oxo-3,4-dihydro-2H-benzo[1,4]oxazin-6-yl)-oxazolidin-5-yl]-ethylamino}-methyl)-4,5-dihydro-pyrrolo[3,2,1-de][1,5]naphthyridin-7-one;
(R)-2-({2-[(R)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;
(S)-2-({2-[(R)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;
(R)-2-({2-[(R)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1-ij]quinolin-4-one;
(S)-2-({2-[(R)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1-ij]quinolin-4-one;
(R)-2-({[(R)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one;
(S)-2-({[(R)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one;
(S)-5-({2-[(S)-2-oxo-3-(3-oxo-3,4-dihydro-2H-benzo[1,4]thiazin-6-yl)-oxazolidin-5-yl]-ethylamino}-methyl)-5,6-dihydro-pyrrolo[1,2,3-de]quinoxalin-3-one;
(S)-5-({[(R)-2-oxo-3-(3-oxo-3,4-dihydro-2H-benzo[1,4]thiazin-6-yl)-oxazolidin-5-ylmethyl]-amino}-methyl)-5,6-dihydro-pyrrolo[1,2,3-de]quinoxalin-3-one;
(R)-5-({2-[(S)-2-oxo-3-(3-oxo-3,4-dihydro-2H-pyrido[3,2-b][1,4]oxazin-6-yl)-oxazolidin-5-yl]-ethylamino}-methyl)-5,6-dihydro-pyrrolo[1,2,3-de]quinoxalin-3-one;
(S)-5-({2-[(S)-2-oxo-3-(3-oxo-3,4-dihydro-2H-pyrido[3,2-b][1,4]oxazin-6-yl)-oxazolidin-5-yl]-ethylamino}-methyl)-5,6-dihydro-pyrrolo[1,2,3-de]quinoxalin-3-one;
as well as the salts (in particular the pharmaceutically acceptable salts) thereof, among which the 43 first compounds and their salts (among which the pharmaceutically acceptable salts will be preferred) constitute a particular embodiment and the 24 first compounds and their salts (among which the pharmaceutically acceptable salts will be preferred) constitute another particular embodiment.

The compounds of formula I according to the invention, i.e. according to one of embodiments i) to xxvii), are suitable for the use as chemotherapeutic active compounds in human and veterinary medicine and as substances for preserving inorganic and organic materials in particular all types of organic materials for example polymers, lubricants, paints, fibres, leather, paper and wood.

The compounds of formula I according to the invention are particularly active against bacteria and bacteria-like organisms. They are therefore particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casseliflavus, S. epidermidis, S. haemolyticus,* or *Peptostreptococcus* spp.; pharyngitis, rheumatic fever, and glomerulonephritis related to infection by *Streptococcus pyogenes*, Groups C and G streptococci, *Corynebacterium diphtheriae*, or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *S. epidermidis, S. haemolyticus*, etc.), *Streptococcus pyogenes, Streptococcus agalactiae*, Streptococcal groups C-F (minute colony streptococci), viridans streptococci, *Corynebacterium minutissimum, Clostridium* spp., or *Bartonella henselae*; uncomplicated acute urinary tract infections related to infection by *Staphylococcus aureus*, coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum,* or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium*, or *Mycobacterium intracellulare*; infections caused by *Mycobacterium tuberculosis, M. leprae, M. paratuberculosis, M. kansasii,* or *M. chelonei*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter pylori* or *Chlamydia pneumoniae*.

The compounds of formula I according to the present invention are further useful for the preparation of a medicament for the treatment of infections that are mediated by bacteria such as *E. coli, Klebsiella pneumoniae* and other Enterobacteriaceae, *Acinetobacter* spp. including *Acineto-*

*bacter baumanii, Stenothrophomonas maltophilia, Neisseria meningitidis, Bacillus cereus, Bacillus anthracis, Corynebacterium* spp., *Propionibacterium acnes* and bacteroide spp. In addition, the compounds of formula I according to the present invention are useful for the preparation of a medicament for the treatment of infections that are mediated by *Clostridium difficile*.

The compounds of formula I according to the present invention are further useful to treat protozoal infections caused by *Plasmodium malaria, Plasmodium falciparum, Toxoplasma gondii, Pneumocystis carinii, Trypanosoma brucei* and *Leishmania* spp.

The present list of pathogens is to be interpreted merely as examples and in no way as limiting.

The compounds of formula I according to this invention, or the pharmaceutically acceptable salts thereof, may be used for the preparation of a medicament, and are suitable, for the prevention or treatment of a bacterial infection.

Accordingly, the compounds of Formula (I) according to this invention, or the pharmaceutically acceptable salts thereof, may be used for the preparation of a medicament, and are suitable, for the prevention or treatment of a bacterial infection selected from the group consisting of respiratory tract infections, otitis media, meningitis, skin and soft tissue infections (whether complicated or uncomplicated), pneumonia (including hospital acquired pneumonia), bacteremia, endocarditis, intraabdominal infections, gastrointestinal infections, *Clostridium difficile* infections, urinary tract infections, sexually transmitted infections, foreign body infections, osteomyelitis, lyme disease, topical infections, opthalmological infections, tuberculosis and tropical diseases (e.g. malaria), and notably for the prevention or treatment of a bacterial infection selected from the group consisting of respiratory tract infections, otitis media, meningitis, skin and soft tissue infections (whether complicated or uncomplicated), pneumonia (including hospital acquired pneumonia) and bacteremia.

As well as in humans, bacterial infections can also be treated using compounds of formula I (or pharmaceutically acceptable salts thereof) in other species like pigs, ruminants, horses, dogs, cats and poultry.

The present invention also relates to pharmacologically acceptable salts and to compositions and formulations of compounds of formula I.

Any reference to a compound of formula I is to be understood as referring also to the salts (and especially the pharmaceutically acceptable salts) of such compounds, as appropriate and expedient.

A pharmaceutical composition according to the present invention contains at least one compound of formula I (or a pharmaceutically acceptable salt thereof) as the active agent and optionally carriers and/or diluents and/or adjuvants, and may also contain additional known antibiotics.

The compounds of formula I and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment of a bacterial infection in a patient comprising the administration to said patient of a pharmaceutically active amount of a compound of formula I or a pharmaceutically acceptable salt thereof. In particular, it concerns such method wherein the bacterial infection is selected from the group consisting of respiratory tract infections, otitis media, meningitis, skin and soft tissue infections (whether complicated or uncomplicated), pneumonia (including hospital acquired pneumonia), bacteremia, endocarditis, intraabdominal infections, gastrointestinal infections, *Clostridium difficile* infections, urinary tract infections, sexually transmitted infections, foreign body infections, osteomyelitis, lyme disease, topical infections, opthalmological infections, tuberculosis and tropical diseases (e.g. malaria), and notably wherein the bacterial infection is selected from the group consisting of respiratory tract infections, otitis media, meningitis, skin and soft tissue infections (whether complicated or uncomplicated), pneumonia (including hospital acquired pneumonia) and bacteremia.

Besides, any preferences indicated for the compounds of formula I (whether for the compounds themselves, salts thereof, compositions containing the compounds or salts thereof, uses of the compounds or salts thereof, etc.) apply mutatis mutandis to compounds of formula $I_{CE}$.

Moreover, the compounds of formula I may also be used for cleaning purposes, e.g. to remove pathogenic microbes and bacteria from surgical instruments or to make a room or an area aseptic. For such purposes, the compounds of formula I could be contained in a solution or in a spray formulation.

The compounds of formula I can be manufactured in accordance with the present invention using the procedures described hereafter.

PREPARATION OF COMPOUNDS OF FORMULA I

Abbreviations:
The following abbreviations are used throughout the specification and the examples:

| | |
|---|---|
| Ac | acetyl |
| AcOH | acetic acid |
| app. | apparent |
| aq. | aqueous |
| AD-mix α | $(DHQ)_2PHAL$, $K_3Fe(CN)_6$, $K_2CO_3$ and $K_2OsO_4.2H_2O$ |
| AD-mix β | $(DHQD)_2PHAL$, $K_3Fe(CN)_6$, $K_2CO_3$ and $K_2OsO_4.2H_2O$ |
| Alloc | allyloxycarbonyl |
| Boc | tert-butoxycarbonyl |
| Bn | benzyl |
| br. | broad |
| Cbz | benzyloxycarbonyl |
| CC | column chromatography over silica gel |
| CDI | 1,1'-carbonyldiimidazole |
| DABCO | 1,4-diazabicyclo[2.2.2]octane |
| DBU | 1,8-diazabicyclo(5.4.0)undec-7-ene |
| DCC | dicyclohexylcarbodiimide |
| DCM | dichloromethane |
| DCE | 1,2-dichloroethane |
| DEAD | diethylazodicarboxylate |
| $(DHQ)_2PHAL$ | 1,4-bis(dihydroquinine)phthalazine |
| $(DHQD)_2PHAL$ | 1,4-bis(dihydroquinidine)phthalazine |
| DIAD | diisobutylazodicarboxylate |
| DIBAH | diisobutylaluminium hydride |
| DIPA | N,N-diisopropylamine |
| DIPEA | N,N-diisopropylethylamine |
| DMA | N,N-dimethylacetamide |
| DMAP | 4-dimethylaminopyridine |
| 1,2-DME | 1,2-dimethoxyethane |
| DMF | N,N-dimethylformamide |
| DMSO | dimethylsulfoxide |
| DPEphos | bis(2-diphenylphosphinophenyl)ether |
| DPPA | diphenyl phosphoryl azide |
| dppf | 1,1'-bis(diphenylphosphino)ferrocene |
| EA | ethyl acetate |

| | |
|---|---|
| EDCI | 1-(3-dimethylaminopropyl)-3-ethylcarbodiimide hydrochloride |
| eq | equivalent |
| ESI | Electron Spray Ionisation |
| Et | ethyl |
| Fmoc | 9-fluorenylmethoxycarbonyl |
| HATU | (O-(7-azabenzotriazol-1-yl)-1,1,3,3-tetramethyl-uronium hexafluorophoshate |
| Hept | heptane |
| Hex | hexane |
| HOBT | hydroxybenzotriazole |
| KHMDS | potassium hexamethyldisilazide |
| LDA | lithium diisopropylamide |
| LiHMDS | lithium hexamethyldisilazide |
| Me | methyl |
| MeCN | acetonitrile |
| min | minutes |
| Ms | methanesulfonyl |
| nBu | n-butyl |
| NMO | N-methylmorpholine-N-oxide |
| NMP | N-methylpyrrolidone |
| Pd/C | palladium on charcoal |
| Ph | phenyl |
| $PPh_3$ | triphenylphosphine |
| $PPh_3O$ | triphenylphosphine oxide |
| PTT | phenyltrimethylammonium tribromide |
| Pyr | pyridine |
| quant. | quantitative |
| rac | racemic |
| rt | room temperature |
| sat. | saturated |
| TBAF | tetrabutyl ammonium fluoride |
| TBDMS | tert-butyldimethylsilyl |
| TBDMSOTf | tert-butyldimethylsilyl-trifluoromethanesulphonate |
| TBDPS | tent-butyldiphenylsilyl |
| TBME | tert-butylmethylether |
| tBu | tert-butyl |
| TEA | triethylamine |
| TEMPO | 2,2,4,4-tetramethylpiperidine-1-oxyl |
| Tf | trifluoromethanesulfonyl (triflyl) |
| TFA | trifluoroacetic acid |
| THF | tetrahydrofuran |
| TMS | trimethylsilyl |
| Ts | p-toluenesulfonyl |
| wt % | percent in weight |

General Synthetic Methods:

General Synthetic Method 1: Alkylation of an Amine:

Ammonia or the appropriate amine derivatives is/are reacted either with the appropriate derivatives having a side group $L^2$, $L^3$ or $L^4$, wherein $L^2$, $L^3$ or $L^4$ represents OMs, OTf, OTs, Cl, Br or I, or with an allyl or homoallyl halogenide in presence of an inorganic base such as $K_2CO_3$ or an org. base such as TEA in a solvent such as THF between 0° C. and +80° C. Further details can be found in *Comprehensive Organic Transformations. A guide to Functional Group Preparations;* $2^{nd}$ Edition, R. C. Larock, Wiley-VC; New York, Chichester, Weinheim, Brisbane, Singapore, Toronto, (1999). Section Amines p. 779.

General Synthetic Method 2: Activation of an Alcohol:

The alcohol is reacted with MsCl, TfCl or TsCl in presence of an organic base such as TEA, DIPEA or Pyr in a dry aprotic solvent such as DCM, THF or Pyr between −10° C. and rt. Alternatively the alcohol can also be reacted with $Ms_2O$ or $Tf_2O$. The activated intermediate can be further transformed into its corresponding iodo or bromo derivative by reaction of the activated alcohol with NaI or NaBr in a solvent such as acetone.

General Synthetic Method 3: Dihydroxylation:

The diol is obtained by dihydroxylation of the corresponding ethylenic derivative using a catalytic amount of osmium tetroxide in the presence a co-oxidant such as NMO in an aq. solvent such as an acetone-water or DCM-water mixture (see Cha, J. K. *Chem. Rev.* (1995), 95, 1761-1795). The chiral cis-diols are obtained by using AD-mix α or AD-mix β in presence of methanesulfonamide in a water/2-methyl-2 propanol mixture as described in *Chem. Rev.* (1994), 94, 2483. The sense of induction relies on the chiral ligand contained in the AD mixture, either a dihydroquinine-based ligand in AD-mix α or a dihydroquinidine-based ligand in AD-mix β.

General Synthetic Method 4: Ester Reduction:

The ester is reduced with a boron or aluminium hydride reducing agent such as $LiBH_4$ or $LiAlH_4$ in a solvent such as THF between −20° C. and 40° C. Alternatively, the ester function is hydrolyzed into its corresponding acid using an alkali hydroxide such as NaOH, KOH or LiOH in water or in a mixture of water with polar protic or aprotic organic solvent such as THF or MeOH between −10° C. and 50° C. The resulting carboxylic acid is further reduced into the corresponding alcohol using a borane derivative such as a $BH_3.THF$ complex in a solvent such as THF between −10° C. and 40° C.

General Synthetic Method 5: Oxidation of Alcohols/Aldehydes into Acids:

Alcohols can be directly oxydized into their corresponding acids by a variety of methods as described in *Comprehensive Organic Transformations. A guide to Functional Group Preparations;* $2^{nd}$ Edition, R. C. Larock, Wiley-VC; New York, Chichester, Weinheim, Brisbane, Singapore, Toronto, 1999. Section nitriles, carboxylic acids and derivatives p. 1646-1648. Among them, [bis(acetoxy)iodo]benzene in presence of TEMPO, the Jones reagents ($CrO_3/H_2SO_4$), $NaIO_4$ in the presence of $RuCl_3$ or $KMnO_4$ are frequently used. Aldehydes can be oxidized into their corresponding acids by a variety of methods as described in *Comprehensive Organic Transformations. A guide to Functional Group Preparations;* $2^{nd}$ Edition, R. C. Larock, Wiley-VC; New York, Chichester, Weinheim, Brisbane, Singapore, Toronto, 1999. Section nitriles, carboxylic acids and derivatives, p. 1653-1655. Among them, $KMnO_4$ in an acetone-water mixture (see *Synthesis* (1987), 85) or sodium chlorite in 2-methyl-2-propanol in presence of 2-methyl-2-butene (see *Tetrahedron* (1981), 37, 2091-2096) are frequently used.

General Synthetic Method 6: Mitsunobu Reaction:

The alcohol is reacted with different nucleophiles such as phenols, phthalimide or hydrazoic acid (generated from $NaN_3$ in acidic medium) in presence of $PPh_3$ and DEAD or DIAD in a solvent such as THF, DMF, DCM or 1,2-DME between −20° C. and 60° C. as reviewed by O. Mitsunobu, in *Synthesis* (1981), 1.

General Synthetic Method 7: Removal of Hydroxy Protecting Groups;

The silyl ether groups are removed either using fluoride anion sources such as TBAF in THF between 0° C. and +40° C. or HF in MeCN between 0° C. and +40° C. or using acidic conditions such as AcOH in THF/MeOH or HCl in MeOH. Further methods to remove the TBDMS and TBDPS groups are given in T. W. Greene, P. G. M. Wuts, *Protecting Groups in Organic Synthesis,* $3^{rd}$ Ed (1999), 133-139 and 142-143 respectively (Publisher: John Wiley and Sons, Inc., New York, N.Y.). Further general methods to remove alcohol protecting groups are described in T. W. Greene, P. G. M. Wuts, *Protecting Groups in Organic Synthesis,* $3^{rd}$ Ed (1999), 23-147 (Publisher: John Wiley and Sons, Inc., New York, N.Y.). In the particular case of alkylcarboxy protecting group, the free alcohol can be obtained by the action of an inorganic base such as $K_2CO_3$ in a solvent such as MeOH.

General Synthetic Method 8: Reductive Amination:

A solution of amine (1 mmol) and aldehyde or ketone (1 mmol) in DCE/MeOH 1:1 (10 mL) is stirred at rt overnight possibly in presence of a dessicant such as $MgSO_4$ or 3 Å molecular sieves. $NaBH_4$ (2-5 eq.) is added and the reaction allowed to proceed for one hour. Alternatively, a solution of amine (1 mmol) and aldehyde or ketone (1 mmol) in DCE/MeOH 1:1 (10 mL) is treated with $NaBH(OAc)_3$ (2 eq).

General Synthetic Method 9: Removal of Amino Protecting Groups:

The benzyl carbamates are deprotected by hydrogenolysis over a noble metal catalyst (e.g. Pd/C or Pd(OH)$_2$/C). The Boc group is removed under acidic conditions such as HCl in an organic solvent such as MeOH or dioxane, or TFA neat or diluted in a solvent such DCM. Further general methods to remove amine protecting groups have been described in T. W. Greene, P. G. M. Wuts, *Protecting Groups in Organic Synthesis*, 3$^{rd}$ Ed (1999), 494-653 (Publisher: John Wiley and Sons, Inc., New York, N.Y.).

General Synthetic Method 10: Protection of Alcohols:

The alcohols are protected as silyl ethers (usually TBDMS or TBDPS ethers). The alcohol is reacted with the required silyl chloride reagent (TBDMSCl or TBDPSCl) in presence of a base such as imidazole or TEA in a solvent such as DCM or DMF between +10° C. and +40° C. Further strategies to introduce other alcohol protecting groups have been described in T. W. Greene, P. G. M. Wuts, *Protecting Groups in Organic Synthesis*, 3rd Ed (1999), 23-147 (Publisher: John Wiley and Sons, Inc., New York, N.Y.).

General Synthetic Method 11: Formation of Aldehydes:

The alcohols can be transformed into their corresponding aldehydes through oxidation under Swern (see D. Swern et al., *J. Org. Chem.* (1978), 43, 2480-2482) or Dess Martin (see D. B. Dess and J. C. Martin, *J. Org. Chem.* (1983), 48, 4155) conditions respectively. Further methods are described in *Comprehensive Organic Transformations. A guide to Functional Group Preparations;* 2$^{nd}$ Edition, R. C. Larock, Wiley-VC; New York, Chichester, Weinheim, Brisbane, Singapore, Toronto, 1999. Section aldehydes and ketones, p. 1235-1236 and 1238-1246.

General Synthetic Method 12: Amine Protection:

Amines are usually protected as carbamates such as Alloc, Cbz, Boc or Fmoc. They are obtained by reacting the amine with allyl or benzyl chloroformate, di tert-butyl dicarbonate or FmocCl in presence of a base such as NaOH, TEA, DMAP or imidazole. They can also be protected as N-benzyl derivatives by reaction with benzyl bromide or chloride in presence of a base such as Na$_2$CO$_3$ or TEA. Alternatively, N-benzyl derivatives can be obtained through reductive amination in presence of benzaldehyde and a borohydride reagent such as NaBH$_4$, NaBH$_3$CN or NaBH(OAc)$_3$ in a solvent such as MeOH, DCE or THF. Further strategies to introduce other amine protecting groups have been described in T. W. Greene, P. G. M. Wuts, *Protecting Groups in Organic Synthesis*, 3rd Ed (1999), 494-653 (Publisher: John Wiley and Sons, Inc., New York, N.Y.).

General Synthetic Method 13: Oxazolidinone Formation:

The 1,2-aminoalcohol derivative is reacted with phosgene, diphosgene or triphosgene. This reaction is preferably carried out in a dry aprotic solvent such as DCM or THF in presence of an organic base such as TEA or pyridine and at a temperature between −30° and +40° C. Alternatively the 1,2-aminoalcohol derivative is reacted with CDI or N,N'-disuccinimidyl carbonate in a dry aprotic solvent such as DCM or THF in presence of an organic base such as TEA or pyridine and at a temperature between −30° and +80° C.

General Preparation Methods:

Preparation of the Compounds of Formula I:

The compounds of formula I can be manufactured by the methods given below, by the methods given in the examples or by analogous methods. Optimum reaction conditions may vary with the particular reactants or solvents used, but such conditions can be determined by a person skilled in the art by routine optimisation procedures.

Sections a) to h) hereafter describe general methods for preparing compounds of formula I. If not indicated otherwise, the generic groups or integers $R^1$, U, V, W, A, n, p, q, G, $G^1$, $G^2$, Z, $Z^0$, $Z^1$, $Z^2$ and Q are as defined for formula I. General synthetic methods used repeatedly throughout the text below are referenced to and described in the above section entitled "General synthetic methods".

a) The compounds of formula I can be manufactured in accordance with the present invention by reacting the compounds of formula II

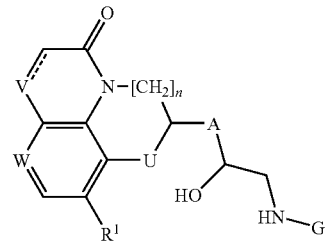

II wherein U is CH$_2$, O or NPG$^0$, PG$^0$ being a protecting group for an amino function such as Boc or Cbz, with the carbonic acid derivatives of formula III

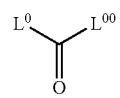

III wherein L$^0$ and L$^{00}$ both represent chloro, OCCl$_3$, imidazolyl or succinimidyloxy, or L$^0$ represents chloro and L$^{00}$ represents OCCl$_3$, followed if necessary by removal of the protecting group PG$^0$ according to general synthetic method 9.

b) The compounds of formula I can also be obtained by reacting the compounds of formula IV

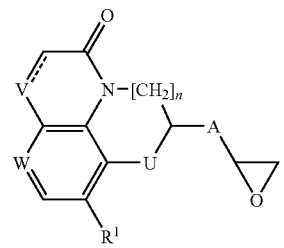

IV wherein U is CH$_2$, O or NPG$^0$, PG$^0$ being a protecting group for an amino function such as Boc or Cbz, with the anions of the compounds of formula V

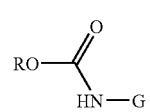

V wherein R represents alkyl or benzyl, generated with a base such as KHMDS or lithium tert-butylate, followed if necessary by removal of the protecting group PG⁰ according to general synthetic method 9.

c) The compounds of formula I can further be obtained by reacting the compounds of formula VI

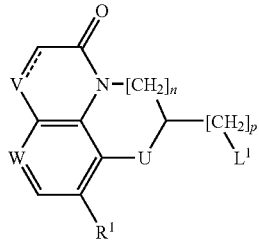

VI wherein U is CH₂, O or NPG⁰, PG⁰ being a protecting group for an amino function such as Boc or Cbz, and L¹ represents a halogen such as chlorine or bromine, or a OSO₂R$^a$ group wherein R$^a$ is alkyl, tolyl or trifluoromethyl, with the compounds of formula VII

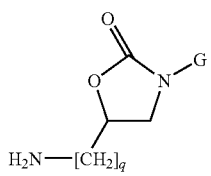

VII wherein q is the integer 1 or 2, followed by removal if necessary of the protecting group PG⁰ according to general synthetic method 9.

d) The compounds of formula I can furthermore be obtained by reacting the compounds of formula VIII

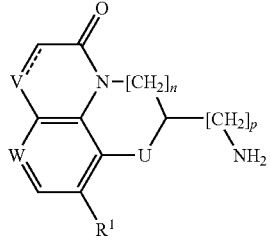

VIII wherein U is CH₂, O or NPG⁰, PG⁰ being a protecting group for an amino function such as Boc or Cbz, with the compounds of formula IX

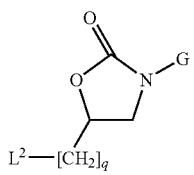

IX wherein L² represents a halogen such as iodine or bromine, or a OSO₂R$^a$ group wherein R$^a$ is alkyl, tolyl or trifluoromethyl, and q is the integer 1 or 2, followed by removal if necessary of the protecting group PG⁰ according to general synthetic method 9.

e) The compounds of formula I wherein V represents CH or N and "-----" is a bond can besides be obtained by ring closing the compounds of formula X

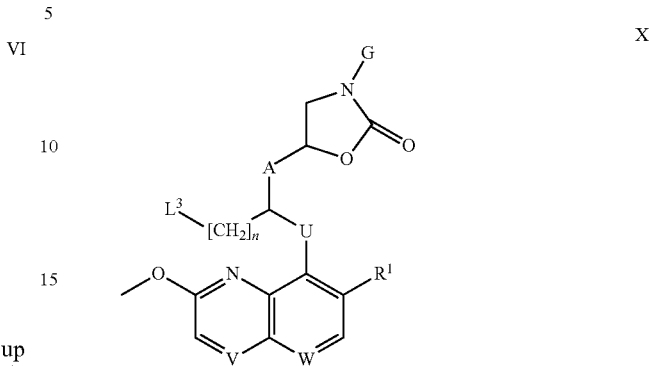

X wherein L³ represents a halogen such as iodine or bromine, or a OSO₂R$^a$ group wherein R$^a$ is alkyl, tolyl or trifluoromethyl, U is CH₂, O or NPG⁰, PG⁰ being a protecting group for an amino function such as Boc or Cbz, n is the integer 0 or 1 (with the proviso that when U represents O or NPG⁰, n is 1), and the amino group in A is either free or protected by a protecting group PG such as Boc or Cbz in a solvent such as toluene between 80° C. and 120° C. The reaction is best performed with the amino group in A being protected following general synthetic method 12. The amino protecting group(s) can be removed after the cyclisation following general synthetic method 9.

f) The compounds of formula I wherein U is CH₂, O or NH can further be obtained by reacting the compounds of formula XI

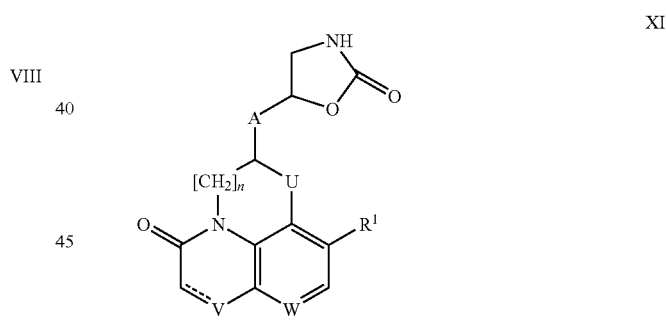

XI wherein U is CHH₂, O or NPG⁰, PG⁰ being a protecting group for an amino function such as Boc or Cbz, with the compounds of formula XII

L⁴-G    XII wherein L⁴ represents OTf or halogen such as chlorine, bromine or iodine. This reaction can be performed under conditions described for the metal catalysed N-arylation of 2-oxazolidinones or amides, in particular using CuI and 1,1,1-tris(hydroxymethyl)ethane in presence of Cs₂CO₃ (*Org. Lett.* (2006), 8, 5609-5612), or Pd(OAc)₂ and DPEphos in presence of K₃PO₄, and be followed, if necessary, by removal of the protecting group PG⁰ according to general synthetic method 9.

g) The compounds of formula I wherein A is CH₂NH(CH₂)$_q$ can also be obtained by reacting under reductive amination conditions (see general synthetic method 8) a compound of formula XIII

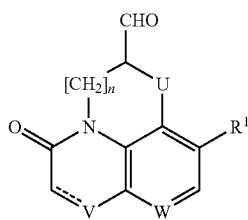

XIII wherein U is $CH_2$, O or $NPG^0$, $PG^0$ being Boc, with an amine of formula VII as described above wherein q is 1 or 2, followed if necessary by removal of the protecting $PG^0$ according to general synthetic method 9.

h) Moreover, the compounds of formula I wherein V represents $CH_2$ or NH and "-----" is absent can be obtained by hydrogenating over a noble metal catalyst such as Pd/C the corresponding compounds of formula I wherein V represents CH or N and "-----" is a bond.

The compounds of formula I thus obtained may, if desired, be converted into their salts, and notably into their pharmaceutically acceptable salts.

Besides, whenever the compounds of formula I are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as triethylamine, diethylamine) and eluent B (hexane), at a flow rate of 0.8 to 150 mL/min. Whenever the compounds of formula I are obtained in the form of mixtures of diastereoisomers, the diastereoisomers can be separated using methods known to one skilled in the art, e.g. chromatography over silica gel, HPLC or crystallisation of their corresponding salts.

Preparation of the Compounds of Formulae II and IV:

The compounds of formulae II and IV can be obtained as summarised in Scheme 1 hereafter.

Scheme 1

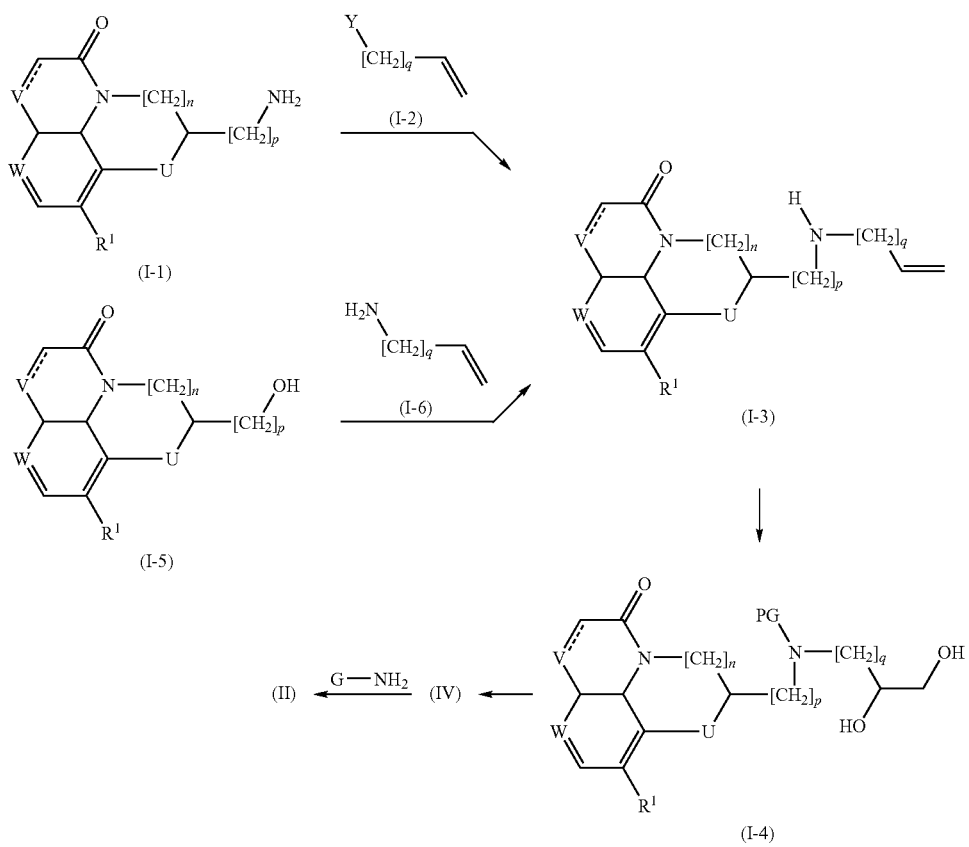

In scheme 1, Y represents a halogen such as iodine or bromine or the group $OSO_2R^a$ wherein $R^a$ is alkyl, trifluoromethyl or tolyl, and PG represents an amino protecting group such as Cbz or Boc.

The compounds of formula I-1 can be alkylated with the derivatives of formula I-2 wherein Y represents a halogen or a group $OSO_2R^a$ wherein $R^a$ is alkyl, trifluoromethyl or tolyl following general synthetic method 1. Alternatively the alcohols of formula I-5 can be activated following general synthetic method 2 and reacted with the amines of formula I-6 following general synthetic method 1. In a further variant the compounds of formula XIII can be reacted with the amines of formula I-6 under reductive amination conditions (general synthetic method 8) affording the compounds of formula I-3 wherein p represents 1. The unsaturated derivatives of formula I-3 can then be transformed into the corresponding diols of formula I-4 after prior protection of the amino group following general synthetic method 12 and cis-dihydroxylation with OsO$_4$/NMO following general synthetic method 3 or as described in *Tetrahedron Lett.* (1976), 23, 1973-76. The epoxides of formula IV can be obtained after mesylation or tosylation, ring closure under basic conditions such as K$_2$CO$_3$ or MeONa and removal of the amino protecting group following general synthetic method 9. In case chiral epoxides are required, they can be obtained by hydrolytic kinetic resolution (HKR) catalyzed by chiral (salen)-Co(III) complex (e.g. [(R,R)—N,N'-bis(3,5-di-tert-butylsalicylidene)-1,2-cyclohexanediaminato(2-)]cobalt(III)) of the racemic mixture of epoxides as described by Jacobsen et al. in *J. Am. Chem. Soc.* (2002), 124, 1307-1315 and *Science* (1997), 277, 936-938. Alternatively, the chiral epoxides can also be obtained from the ethylenic derivatives of formula I-3 through either Shi chiral epoxidation using a chiral ketone as described in *Acc. Chem. Res.* (2004), 37, 488-496 or through chiral dihydroxylation (see general synthetic method 3). The epoxides of formula IV can be further reacted with the amines of formula G-NH$_2$, affording the compounds of formula II.

Preparation of the Compounds of Formula V:

The carbamates of formula V can be prepared from the corresponding amines of formula G-NH$_2$ following general synthetic method 12.

Preparation of the Compounds of Formulae VI and VIII:

The compounds of formulae VI and VIII wherein U represents CH$_2$, n is 1 and p is 1 can be obtained as summarised in Scheme 2 hereafter.

In Scheme 2, L$^1$ represents a halogen such as iodine or bromine or the group OSO$_2$R$^a$ wherein R$^a$ is alkyl, tolyl or trifluoromethyl and PG$^1$ is a protecting group for an amino function such as Boc or Cbz.

The bromomethyl derivatives of formula II-1 can be reacted with diethyl malonate in presence of a base such as NaH. The resulting diesters of formula II-2 can be reduced into their corresponding diols with a hydride reagent following general synthetic method 4. The resulting diols can then be sequentially reacted with trimethyl orthoacetate in presence of traces of TsOH and afterwards with aq. AcOH, affording the alcohols of formula II-3. These alcohols can be transformed into their corresponding mesylate, tosylate, triflate or halogenide derivatives following general synthetic method 2 before being ring closed by heating in refluxing toluene and finally treated with K$_2$CO$_3$ in an alcohol to transform the intermediate acetates into the alcohols of formula II-4. The alcohols of formula II-4 can be transformed into their corresponding mesylate, tosylate or triflate derivatives (VI; L$^1$=OSO$_2$R$^a$) following general synthetic method 2 or their corresponding halogen derivatives (VI; L$^1$=halogen) followed by reaction with NaN$_3$ and reaction with PPh$_3$/water, affording the amines of formula VIII (p=1). The compounds of formula VIII can also be obtained by reacting the bromomethyl derivatives of formula II-1 with the β-amino esters of formula II-5 in presence of a strong base such as LiHMDS. The resulting esters of formula II-6 can be reduced into the corresponding alcohols with a hydride reagent following gen-

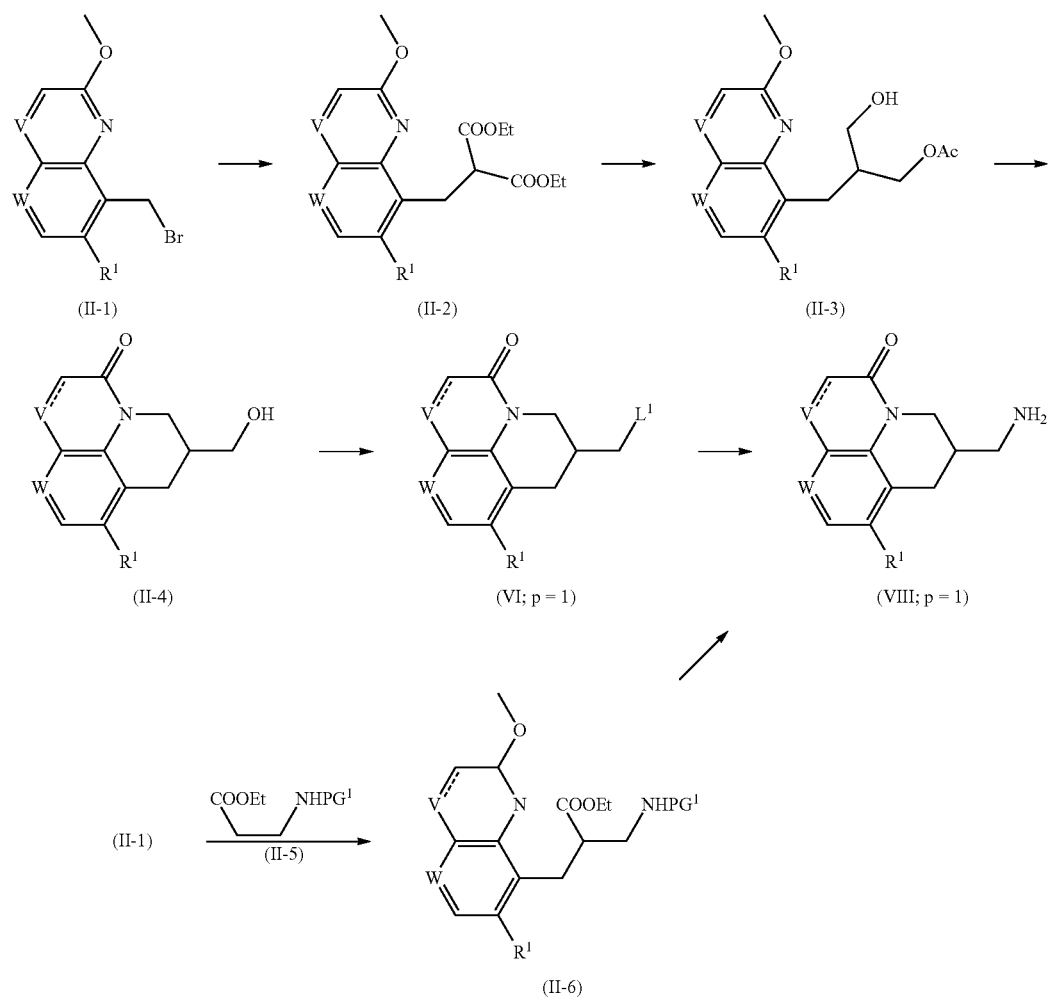

Scheme 2 eral synthetic method 4, activated following general synthetic method 2 and thermally ring closed. The amino protecting group on the tricyclic intermediate compound can then be removed following general synthetic method 9, affording the compounds of formula VIII. The compounds of formulae II-4, VI, VIII and II-6 wherein "-----" is absent can be obtained by hydrogenating the corresponding compounds wherein "-----" is a bond.

The compounds of formula VIII wherein U represents CH$_2$, n is 1 and p is 0 can be obtained as summarised in Scheme 3 hereafter.

Scheme 3

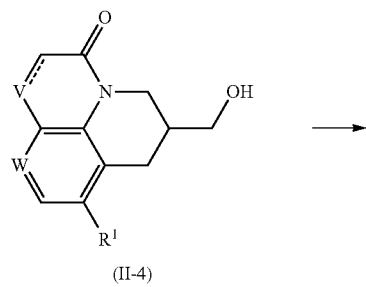

(II-4)

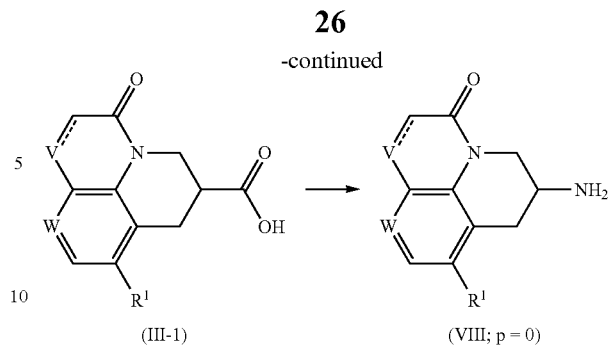

(III-1)   (VIII; p = 0)

The alcohols of formula II-4 can be oxidized (Scheme 3) into their corresponding carboxylic acids following general synthetic method 5. The resulting acids of formula III-1 can be transformed into the amino derivatives of formula VIII after reaction with DPPA and heating of the intermediate azidocarbonyl derivative in presence of water.

The compounds of formulae VI and VIII wherein U represents O and p is 1 can be obtained as summarised in Scheme 4 hereafter.

Scheme 4

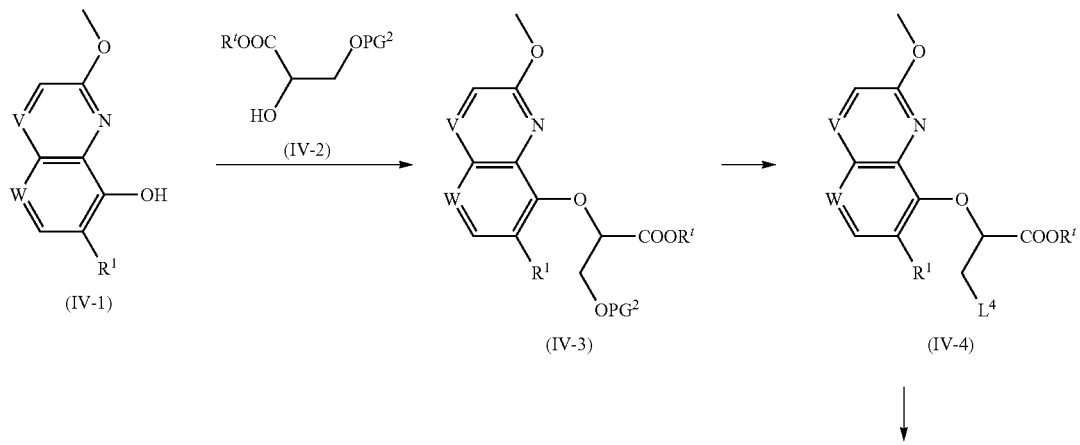

(IV-1)   (IV-3)   (IV-4)

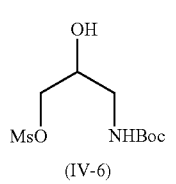

(IV-6)

↓ (IV-1)

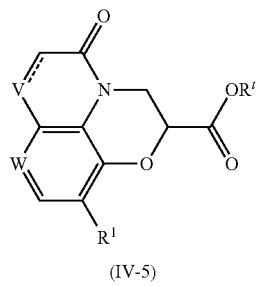

(IV-5)

↓ (IV-5)

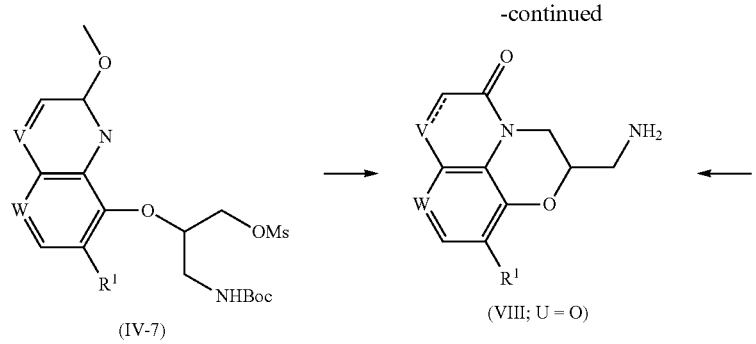 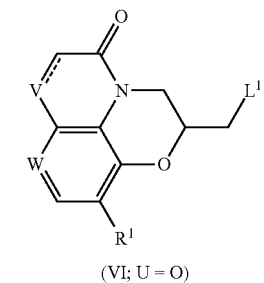

In Scheme 4, $R^t$ represents alkyl or benzyl, $PG^2$ represents a hydroxy protecting group such as TBDMS or TBDPS and each of $L^1$ and $L^4$ represents independently a halogen such as iodine or bromine or the group $OSO_2R^a$ wherein $R^a$ is alkyl, tolyl or trifluoromethyl.

The phenol derivatives of formula IV-1 can be reacted following general synthetic method 6 with the alcohols of formula IV-2. The hydroxy protecting group in the compounds of formula IV-3 can be removed following general synthetic method 7 and the resulting alcohols can be activated as mesylate, tosylate, triflate, iodo or bromo derivatives following general synthetic method 2. The resulting derivatives of formula IV-4 can be thermally ring closed in boiling toluene affording the tricyclic derivatives of formula IV-5. These tricyclic esters can then be reduced following general synthetic method 4, and the resulting alcohols can be activated following general synthetic method 2 to yield the mesylate, tosylate, triflate, iodo or bromo derivatives of formula VI, which can in turn be reacted with ammonia following general synthetic method 1, or sequentially reacted with sodium azide and with $PPh_3$ in the presence of water, affording the derivatives of formula VIII. The compounds of formula VIII can also be obtained by mono mesylation of (2,3-dihydroxypropyl)carbamic acid tert-butyl ester following general synthetic method 2 (leading to the compound of formula IV-6), followed by sequential reaction with the phenol derivatives of formula IV-1 following general synthetic method 6, ring closure of the intermediates of formula IV-7 and removal of the Boc group following general synthetic method 9. The compounds of formulae IV-5, VI and VIII wherein "-----" is absent can be obtained by hydrogenating the corresponding compounds wherein "-----" is a bond.

An alternative route for preparing the compounds of formulae VI and VIII wherein U represents O and p is 1 is shown in Scheme 4a hereafter.

Scheme 4a

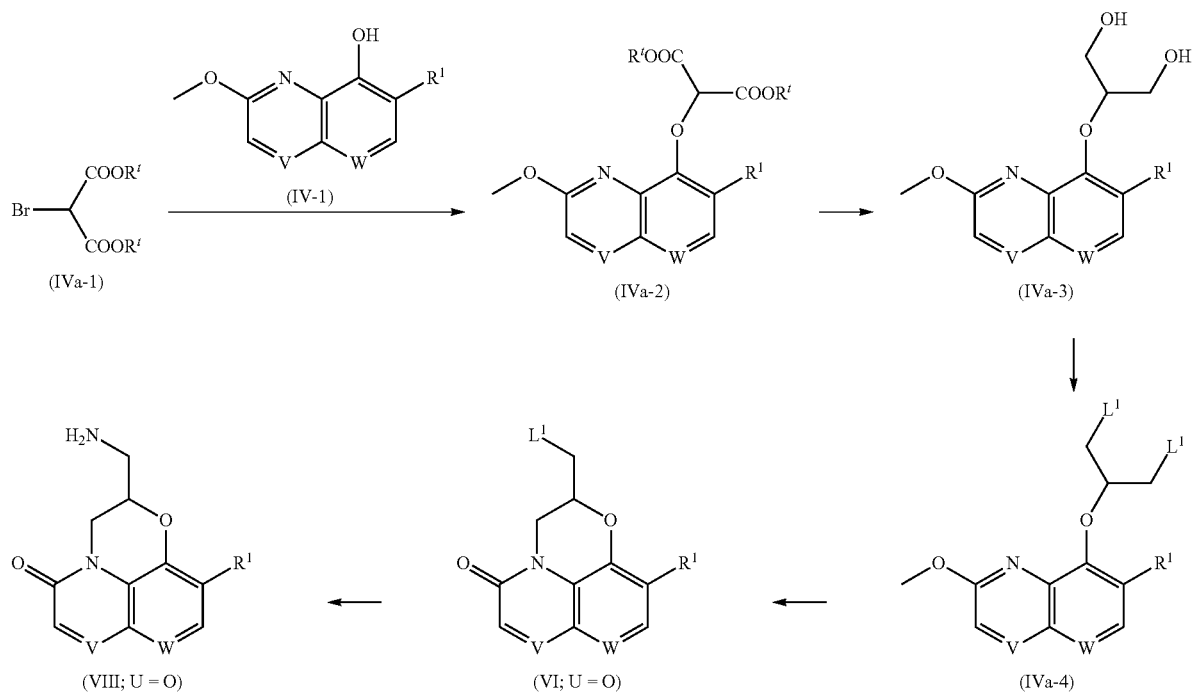

In Scheme 4a, $R^t$ represents alkyl or benzyl and $L^1$ represents a halogen such as iodine or bromine or the group $OSO_2R^a$ wherein $R^a$ is alkyl, tolyl or trifluoromethyl.

According to this alternative route, the compounds of formula VI can be obtained by reacting the phenol derivatives of formula IV-1 with a bromo malonate of formula IVa-1 in the presence of an inorganic base such as $Cs_2CO_3$ or $K_2CO_3$ in a solvent such as DMF or NMP. The resulting malonate derivatives of formula IVa-2 can then be transformed into the dials of formula IVa-3 according to general synthetic method 4 (notably using an excess of LiAlH$_4$ in THF). The dials of formula IVa-3 can then be transformed into derivatives of formula IVa-4 using general synthetic method 2. In case L$^1$ is OMs, the resulting bismesylates of formula IVa-4 can be ring closed in boiling toluene, affording the tricyclic derivatives of formula VI. The latter can be converted into the compounds of formula VIII by reaction with ammonia following general synthetic method 1, or by sequential reaction with sodium azide and with PPh$_3$ in the presence of water. The compounds of formulae VI and VIII wherein "-----" is absent can be obtained by hydrogenating the corresponding compounds wherein "-----" is a bond.

The compounds of formulae VI and VIII wherein U represents NPG$^0$ can be obtained as summarised in Scheme 4b hereafter.

iodine or bromine or the group OSO$_2$R$^a$ wherein R$^a$ is alkyl, tolyl or trifluoromethyl and each of Hal and X represents halogen such as bromine.

The aniline derivatives of formula IVb-1 can be reacted with the halogenides of formula IVb-2. The resulting derivatives of formula IVb-3 can be N-protected following general synthetic method 12 to yield the compounds of formula IVb-4. The latter can then be transformed into the compounds of formula IVb-5 after sequential reduction of the ester function following general synthetic method 4, activation of the primary alcohol function following general synthetic method 2 and removal of the silyl protecting group following general synthetic method 7. Ring closure under thermal conditions affords the intermediates of formula IVb-6 which can be activated following general synthetic method 2, affording the intermediates of formula VI. The compounds of formula VIII wherein U is NPG$^0$ can then be obtained using the same

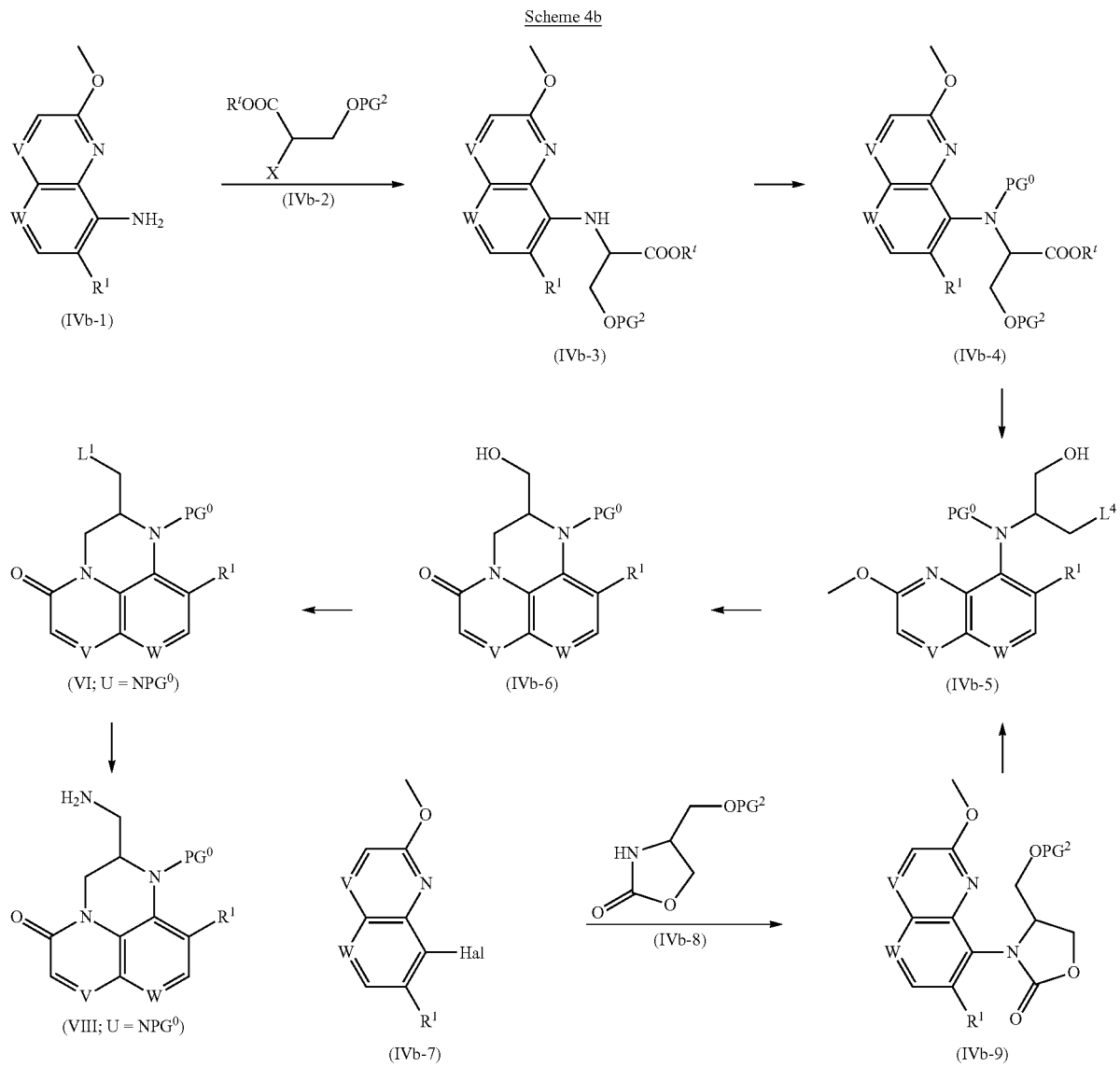

Scheme 4b

In Scheme 4b, PG$^0$ represents an amino protecting group such as Cbz or Boc, R$^r$ represents alkyl or benzyl, PG$^2$ represents a hydroxy protecting group such as TBDMS or TBDPS, L$^1$ and L$^4$ each independently represent a halogen such as iodine or bromine or the group OSO$_2$R$^a$ wherein R$^a$ is alkyl, methods described for the synthesis of compounds of formula VIII wherein U is O (see Scheme 4). Alternatively the derivatives of formula IVb-7 can be reacted with the oxazolidinone derivatives of formula IVb-8 under Buchwald coupling conditions as described in *Org. Lett.* (2000), 2, 1101-1104. The resulting derivatives of formula IVb-9 can be hydrolyzed with KOH to yield the corresponding amino-alcohol derivatives. After N-protection of the latter (general synthetic method 12), activation of the primary alcohol (general synthetic method 2) and removal of the silylether protecting group (general synthetic method 7), the intermediates of formula IVb-5 can be obtained. The compounds of formulae IVb-6, VI and VIII, wherein "-----" is absent can be obtained by hydrogenating the corresponding compounds wherein "-----" is a bond.

The compounds of formulae VI and VIII wherein U represents $CH_2$, n is 0 and p is 1 can be obtained as summarised in Scheme 5 hereafter.

The esters of formula V-1 (which can be obtained by hydrogenation of the corresponding acrylate derivatives of formula V-4 over a noble metal catalyst, said vinylic derivatives of formula V-4 being themselves obtained either by Wittig olefination of the aldehydes of formula V-7 with ethoxycarbonylmethylenetriphenylphosphorane or by reaction of the halogenide derivatives of formula IVb-7 with an alkyl acrylate derivative under Heck conditions) can be transformed into the corresponding bromo derivatives of formula V-2 after deprotonation with LDA and sequential reaction with TMSCl and PTT. The resulting bromo derivatives of formula V-2 can be ring closed in refluxing toluene affording the tricyclic esters of formula V-3. Reduction of the ester function of the com-

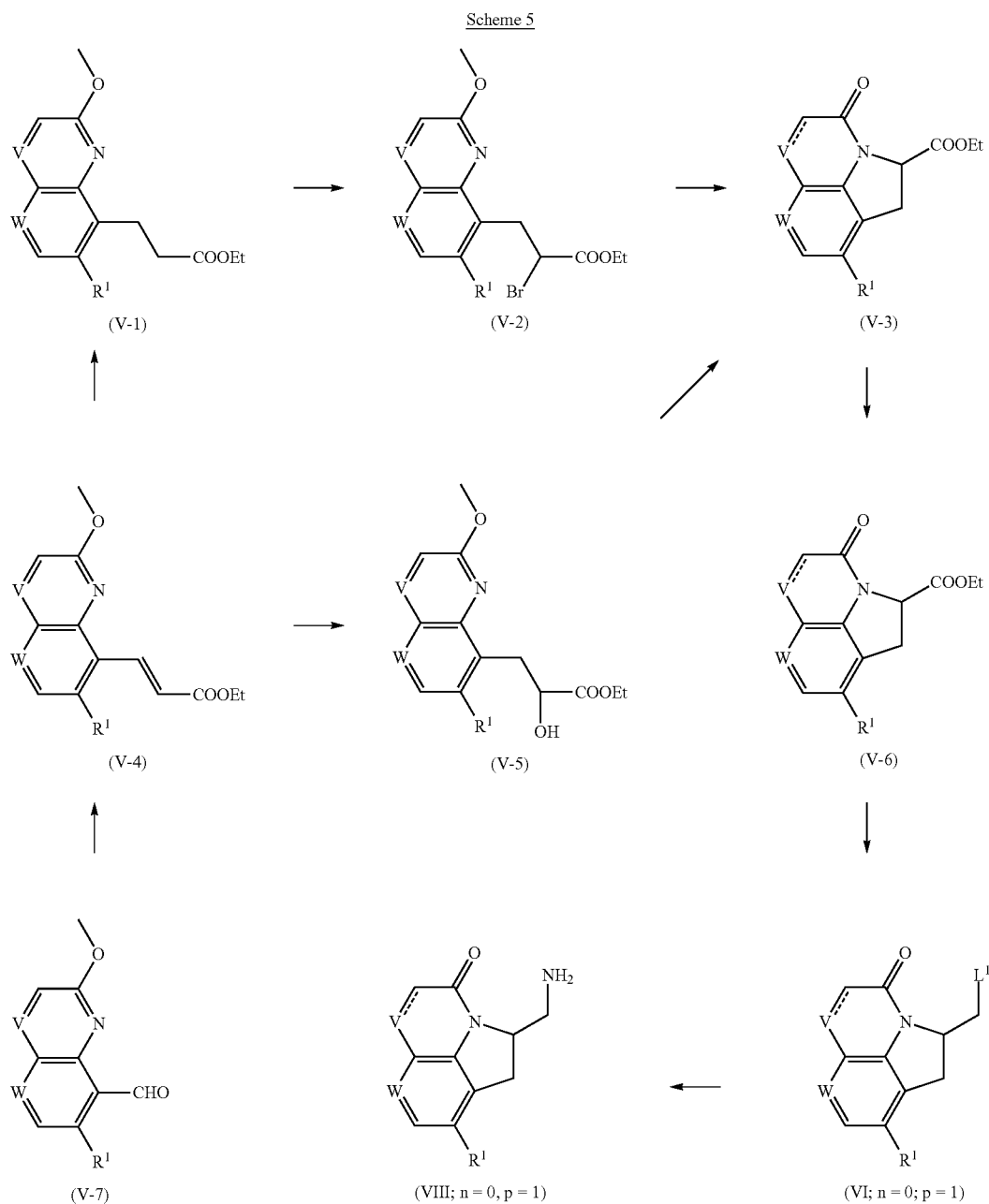

Scheme 5

In Scheme 5, $L^1$ represents a halogen such as iodine or bromine or the group $OSO_2R^a$ wherein $R^a$ is alkyl, tolyl or trifluoromethyl.

pounds of formula V-3 following general synthetic method 4 leads to the formation of the alcohols of formula V-6 which can in turn be transformed into the corresponding mesylate or bromo derivatives of formula VI following general synthetic method 2 and finally be reacted with ammonia following general synthetic method 1 or with sodium azide followed by reaction with PPh₃ in the presence of water to afford the amino derivatives of formula VIII. The esters of formula V-3 can also be obtained from the unsaturated derivatives of formula V-4 after cis-dihydroxylation following general synthetic method 3, followed by cyclic carbonate formation in presence of triphosgene and hydrogenolysis over a noble metal catalyst, thus affording the α-hydroxy esters of formula V-5. As the cis-dihydroxylation is performed either with AD-mix α or with AD-mix β, the two (R) and (S) enantiomers can be obtained accordingly. The alcohol function of the intermediates of formula V-5 can be activated following general synthetic method 2 and thermal ring closure can then be carried out to afford the intermediates of formula V-3. The compounds of formulae V-3, V-6, VI and VIII wherein "-----" is absent can be obtained by hydrogenating the corresponding compounds wherein "-----" is a bond.

Preparation of the Compounds of Formula VII:

The intermediates of formula VII wherein q is 1 or 2 can be obtained as summarised in Scheme 6 hereafter.

Scheme 6

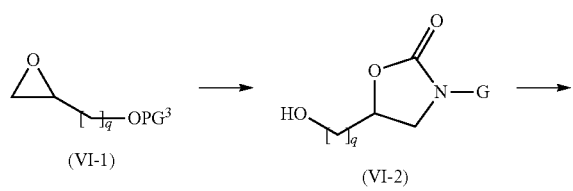

(VI-1)    (VI-2)

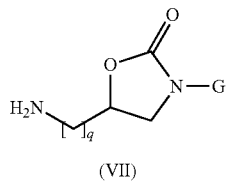

(VII)

In Scheme 6, PG³ represents —C(O)R", wherein R" represents alkyl or benzyl, or PG³ represents a silyl protecting group such as TBDMS or TBDPS.

The compounds of formula VII can thus be obtained from the corresponding alcohols of formula VI-2 after activation of the alcohol according to general synthetic method 2 followed by reaction with sodium azide and subsequent hydrogenation in presence of a noble metal catalyst such as Pd/C or reduced in presence of PPh₃/H₂O. The alcohols of formula VI-2 can be obtained by reaction of the epoxides of formula VI-1 with the anions of the carbamates of formula V following a method analogous to that of method b) of the section "Preparation of the compounds of formula I", followed by alcohol deprotection as described in general synthetic method 7.

Preparation of the Compounds of Formula IX:

The compounds of formula IX can be prepared from the compounds of formula VI-2 described in the section "Preparation of the compounds of formula VII" using general synthetic method 2.

Preparation of the Compounds of Formula X:

The compounds of formula X wherein U represents CH₂, n and p are each 1 and q is 1 or 2 can be obtained as summarised in Scheme 7 hereafter.

Scheme 7

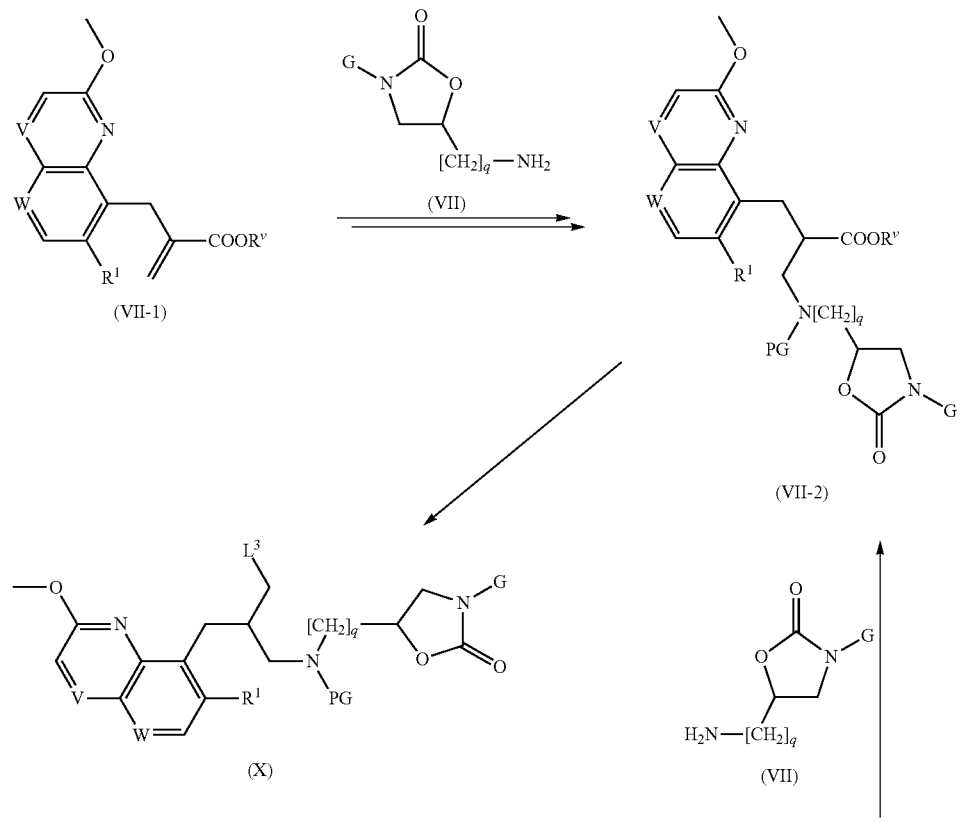

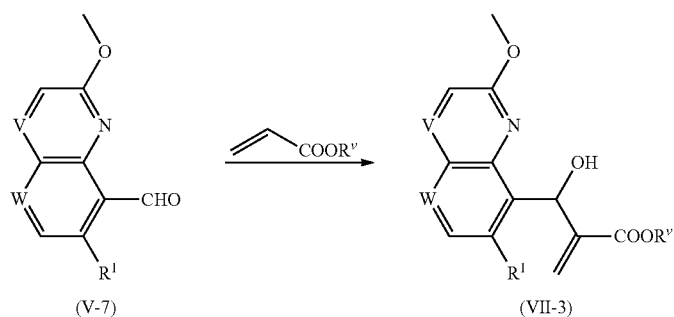

In Scheme 7, $R^v$ represents alkyl or benzyl, PG represents an amino protecting group such as Boc or Cbz and $L^3$ represents a halogen such a iodine or bromine or the group $OSO_2R^a$ wherein $R^a$ is alkyl, tolyl or trifluoromethyl.

The esters of formula VII-1 can be reacted with the amines of formula VII, affording, after protection of central amino group following general synthetic method 12, the oxazolidinones of formula VII-2. Alternatively the derivatives of formula VII-2 can also be obtained from the derivatives of formula VII-3 after sequential acylation with acetanhydride, reaction with the amines of formula VII, hydrogenation of the double bond and protection of amine function following general synthetic method 12. The required compounds of formula VII-3 are obtained by reaction of the aldehydes of formula V-7 with an acrylate in presence of DABCO. The esters of formula VII-2 can then be reduced into the corresponding alcohols following general synthetic method 4 and the hydroxy group can then be activated following general synthetic method 2, affording the compounds of formula X wherein the amino group of the radical A is protected. If desired, the compounds of formula X with the free amino group can be obtained using general synthetic method 9.

The compounds of formula X wherein U represents $CH_2$, n is 1, p is 0 and q is 2 can be obtained as summarised in Scheme 8 hereafter.

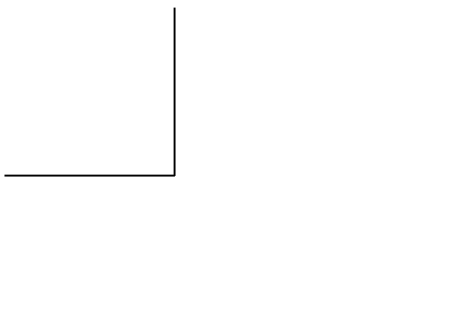

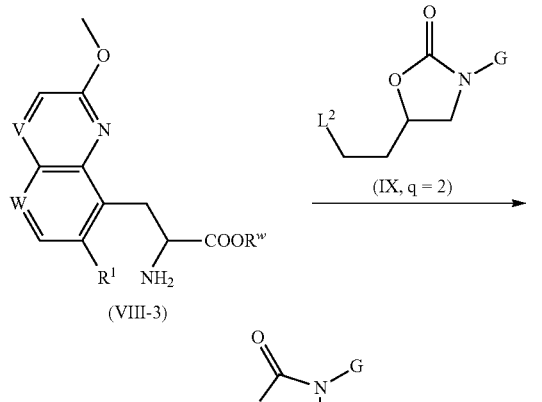

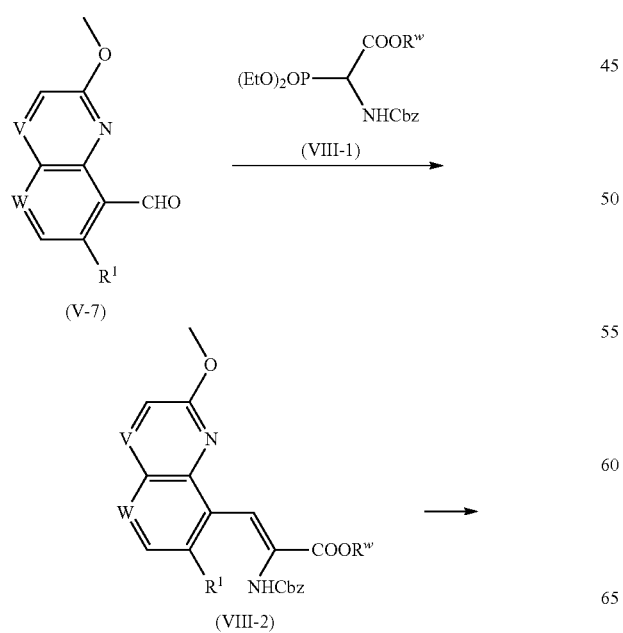

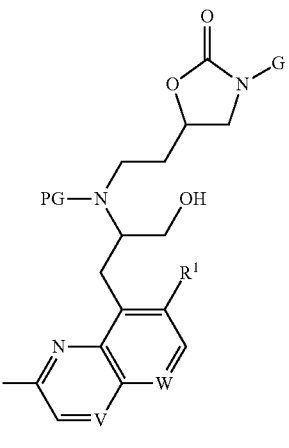

In Scheme 8, $R^w$ represents alkyl or benzyl and $L^2$ represents $OSO_2R^a$ or halogen such as bromine, $R^a$ represents methyl, trifluoromethyl or tolyl and PG represents an amino protecting group such as Boc or Cbz.

The aldehydes of formula V-7 can be reacted with the 2-(diethoxyphosphinyl)-2-[[(phenylmethoxy)carbonyl]amino]-acetic acid alkyl esters of formula VIII-1, affording the vinylic derivatives of formula VIII-2, which can be hydrogenated over a noble metal catalyst such as Pd/C. The resulting compounds of formula VIII-3 can be reacted with the derivatives of formula IX wherein q is 2 following general synthetic method 1, affording intermediate compounds which can be converted into the corresponding amino protected compounds of formula VIII-4 following general synthetic method 12. The ester function of the compounds of formula VIII-4 can be reduced to yield the corresponding alcohols of formula X following general synthetic method 4. The alcohol function of the compounds of formula X wherein PG is an amino protecting group can then be activated following general synthetic method 2. If desired, the compounds of formula X with the free amino group can be obtained using general synthetic method 9.

The compounds of formula X wherein U represents O, n and p are each 1 and q is 1 or 2 can be obtained as summarised in Scheme 9 hereafter.

In Scheme 9, $PG^4$ represents an amino protecting group such as Cbz, and $PG^5$ represents a hydroxyl protecting group such as TBDMS or TBDPS.

The oxazolidinone derivative of formula VII can be reacted with glyceraldehyde acetonide following general synthetic method 8, the amino group being then protected with CbzCl following general synthetic method 12 and the diol group being deprotected by treatment in an aq. org. solvent such as acetone or THF in presence of acid such HCl or AcOH, thus affording the diol of formula IX-1. The latter can be monoprotected with a TBDMS or TBDPS group following general synthetic method 10. The resulting alcohols of formula IX-2 can be reacted with the phenol derivatives of formula IV-1 (see section "Preparation of the compounds of formulae VI and VIII", Scheme 4) following general synthetic method 6 to afford the compounds of formula IX-3. The alcohol protecting group of the latter can then be removed following general synthetic method 7, the resulting free alcohol can be activated following general synthetic method 2 and the amino protecting group can then be removed following general synthetic method 9, thus affording the compounds of formula X wherein U represents O, n and p are each 1 and q is 1 or 2.

The compounds of formula X wherein U represents $NPG^0$, n and p are each 1 and q is 1 or 2 can be obtained as summarised in Scheme 9a hereafter.

Scheme 9

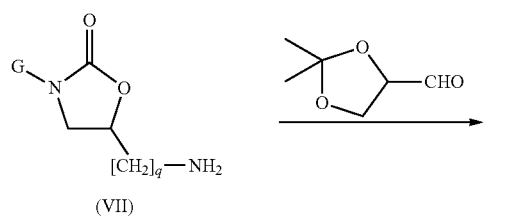

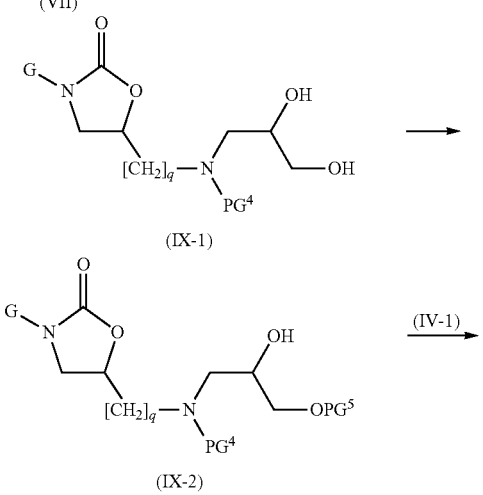

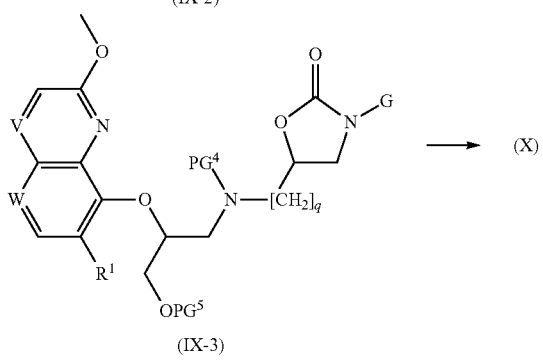

Scheme 9a

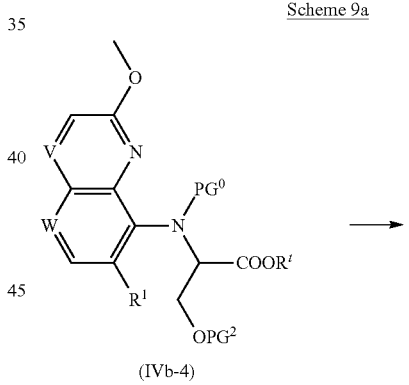

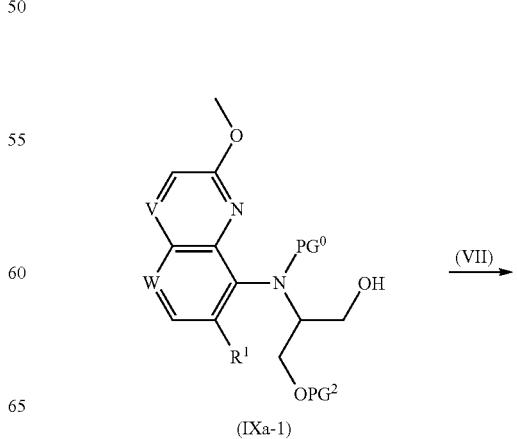

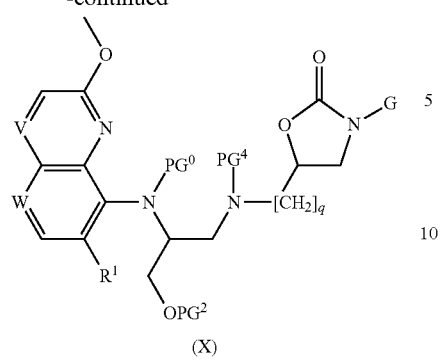

(X)

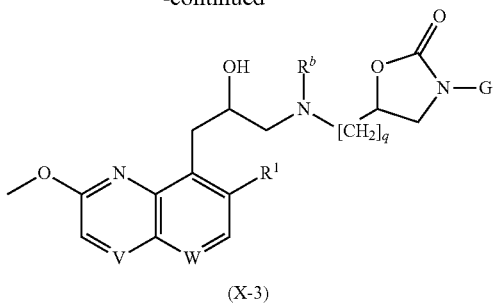

(X-3)

In Scheme 9a, $PG^4$ and $PG^0$ each independently represent an amino protecting group such as Cbz or Boc and $PG^2$ represents a hydroxyl protecting group such as TBDMS or TBDPS.

The compounds of formula X wherein U represents $NPG^0$, n and p are each 1 and q is 1 or 2 can be obtained as summarised in Scheme 9a by reduction of the ester function of intermediates of formula IVb-4 following general synthetic method 4 to give the compounds of formula IXa-1, activation of the alcohol function following general synthetic method 2, reaction with the derivatives of VII following general synthetic method I and protection of the amine function following general synthetic method 12.

The compounds of formula X wherein U represents $CH_2$, n is 0, p is 1 and q is 1 or 2 can be obtained as summarised in Scheme 10 hereafter.

Scheme 10

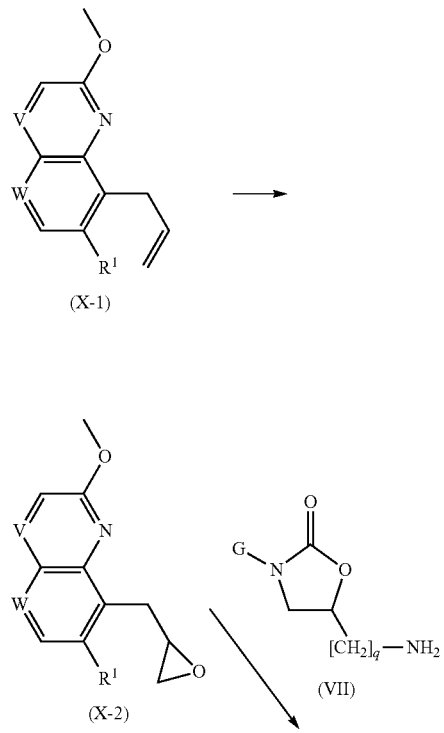

In Scheme 10, $R^b$ represents hydrogen or an amino protecting group such as Boc or Cbz and $L^3$ represents a halogen such as iodine or bromine or the group $OSO_2R^a$ wherein $R^a$ is alkyl, tolyl or trifluoromethyl.

The allylic derivatives of formula X-1 can be dihydroxylated following general synthetic method 3 and the epoxides of formula X-2 can then be formed after activation of the primary alcohols as mesylates using general synthetic method 2 and ring closure in presence of a base such as TEA. Said epoxides can be reacted with the amines of formula VII and the intermediate compounds of formula X-3 wherein $R^b$ is H can be converted into the corresponding compound of formula X-3 wherein $R^b$ is an amino protecting group using general synthetic method 12. The alcohol function of the compounds of formula X-3 wherein $R^b$ is an amino protecting group can then be activated using general synthetic method 2. In this particular case, the amino protecting group can be conserved and removed after the ring closure step.

Preparation of the Compounds of Formula XI:

The compounds of formula XI can be obtained by reacting the epoxides of formula IV with sodium azide followed by hydrogenation over a noble metal catalyst such as Pd/C or reduction in presence of $PPh_3/H_2O$ and subsequent transformation into their corresponding carbamates with CbzCl or $Boc_2O$. The oxazolidinone ring can then be formed by subsequent reaction with NaH.

Preparation of the Compounds of Formula XII:

Some compounds of formula XII are commercially available (e.g. compounds wherein $G=G^1$, Q=O and Z=N: CAS 337463-99-7; $G=G^1$, Q=S and Z=CH: CAS 6376-70-1; $G=G^1$, Q=O and Z=CH: CAS 7652-29-1). Besides, the compound of formula XII wherein G is $G^1$, Z is N, Q is S and $L^4$ is Cl can be obtained as summarised in Scheme 11 hereafter.

Scheme 11

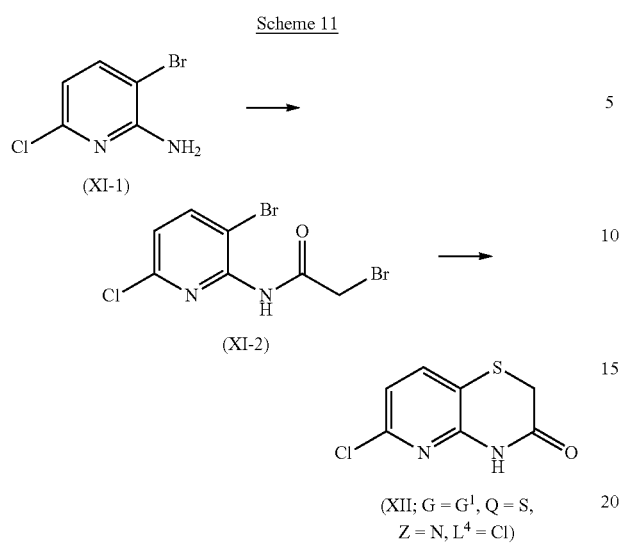

Accordingly, the bromo derivative of formula XI-1, prepared according to WO 2008/065198, can be reacted with bromoacetyl bromide and the resulting derivative of formula XI-2 can then be reacted with sodium thioacetate in the presence of NaOMe, affording the compound of formula XII wherein G is $G^1$, Z is N, Q is S and $L^4$ is Cl.

The compounds of formula XII wherein G is $G^1$, Z is CH, Q is O or S and $L^4$ is OTf and those wherein G is $G^2$, each of $Z^0$, $Z^1$ and $Z^2$ is CH and $L^4$ is OTf can be obtained from the corresponding alcohol precursors ($L^4$=OH) and $Tf_2O$ following general synthetic method 2. The latter compounds are either commercially available (CAS 53412-38-7; CAS 10288-72-9) or can be prepared as described in EP 106 816.

Preparation of the Compounds of Formula XIII:

The compounds of formula XIII can be obtained by oxidizing the alcohols of formula I-5 wherein p is 1 (see section "Preparation of the compounds of formulae II and IV") using general synthetic method 11.

Preparation of Starting Compounds:

The derivatives of formula $G-NH_2$ can be obtained as summarised in Scheme 12 hereafter.

Scheme 12

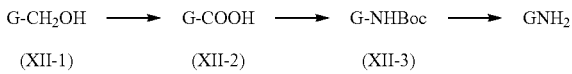

The known benzylic alcohols of formula XII-1 can thus be oxidized into the corresponding carboxylic acids following general synthetic method 5. The resulting carboxylic acids of formula XII-2 can then be reacted with diphenylphosphoryl azide in presence of tBuOH between 40° and 100° C., affording the carbamates of formula XII-3. The compounds of formula $G-NH_2$ can then be obtained following general synthetic method 9.

The compounds of formula I-1 can be obtained from the compounds of formula I-5 by activating the alcohol using general synthetic method 2 and reacting the activated intermediate either with ammonia using general synthetic method 1 or with sodium azide followed by reaction with $PPh_3$ in the presence of water. The compounds of formula I-5 can be obtained using methods described in Schemes 2, 4, 4a, 4b and 5.

The compounds of formula II-1 can be obtained according to WO 2006/046552 or WO 2007/081597. The compounds of formula II-5 can be obtained according to WO 2005/019177.

The compounds of formula IVb-1 are commercial (e.g. $R^1$=H, W=N: CAS 249889-69-8) or prepared according to WO 2006/046552 ($R^1$=F or H, W=CH). The compounds of formula IVb-2 can be prepared according to Tetrahedron (1993), 49, 4841-4858.

The compounds of formula V-7 can be prepared according to WO 2006/032466 or WO 2006/046552.

The compounds of formulae VII-1 and X-1 can be obtained as summarised in Scheme 13 hereafter.

Scheme 13

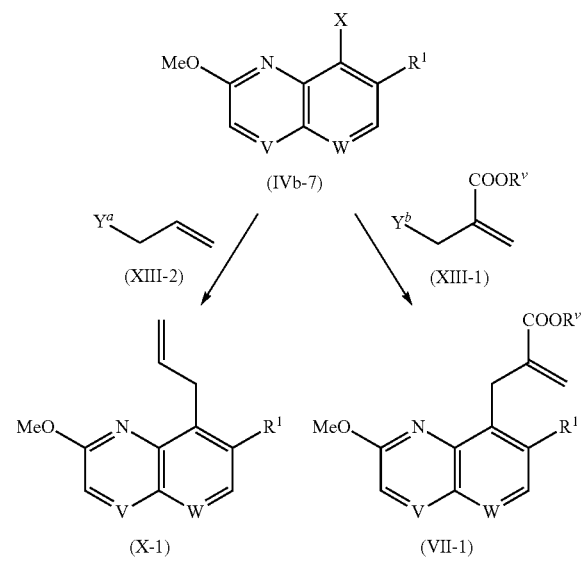

In Scheme 13, $R^v$ represents alkyl or benzyl, X represents OTf or halogen such as bromine, $Y^a$ represents halogen such as bromine or tributylstannyl and $Y^b$ represents halogen such as bromine or hydrogen.

Accordingly, the Grignard derivatives generated from the derivatives of formula IVb-7 with alkylmagnesium halides can be reacted with the bromo derivatives of formula XIII-1 ($Y^b$=Br) or XIII-2 ($Y^a$=Br), affording the compounds of formula VII-1 or X-1. Alternatively, the compounds of formula X-1 can also be obtained by reacting the compounds of formula IVb-7 with the tributylstannyl derivatives of formula XIII-2 ($Y^a$=SnBu$_3$) in the presence of a palladium catalyst such as $Pd(PPh_3)_4$. The compounds of formula VII-1 can further be obtained by reacting the compounds of formula IVb-7 with the compounds of formula XIII-1 ($Y^b$=H) in the presence of a palladium catalyst such as $Pd(OAc)_7$.

Particular embodiments of the invention are described in the following Examples, which serve to illustrate the invention in more detail without limiting its scope in any way.

EXAMPLES

All temperatures are stated in ° C. Compounds are characterized by $^1$H-NMR (300 MHz) (Varian Oxford); or by $^1$H-NMR (400 MHz) (Bruker Advance 400). Chemical shifts are given in ppm relative to the solvent used; multiplicities: s=singlet, d=doublet, t=triplet, q=quadruplet, p=pentuplet, hex=hexet, hept=heptet, m=multiplet, br.=broad, coupling constants are given in Hz. Alternatively compounds are characterized by LC-MS (Sciex API 2000 with Agilent 1100 Binary Pump and DAD, using RP-C18 based columns); by TLC (TLC-plates from Merck, Silica gel 60 $F_{254}$); or by melting point. Compounds are purified by chromatography on Silica gel 60 A. $NH_4OH$ as used for CC is 25% aq. Racemates can be separated into their enantiomers as described before. Preferred conditions of chiral HPLC are: ChiralPak AD (4.6×250 mm, 5 μm) column, using an isocratic mixture (eg. at a ratio of 10/90) of eluent A (EtOH, in presence of diethylamine in an amount of e.g. 0.1%) and eluent B (hexane), at rt, at a flow rate of eg. 0.8 mL/min.

General Methods:

General Method A: Boc Deprotection:

The Boc-protected amine (1 mmol) was dissolved in DCM (2 mL). and TFA (2 mL) and optionally $Et_3SiH$ (1.05 mmol) was/were added. The mixture was stirred at rt for 1 h, concentrated in vacuo and taken up in $DCM/NH_4OH$. The org. layer was washed with water, dried over $MgSO_4$ and concentrated under reduced pressure.

General Method B: Alkylation of Amines with Iodides and Mesylates:

A solution of the amine (1 mmol in the case of iodides; 1-2 mmol in the case of mesylates), mesylate/iodide (1 mmol) and DIPEA (1.1 mmol) in dry DMSO was heated to 70° C. until completion of the reaction (1-3 days). After cooling to rt, water and EA were added and the phases were separated. The aq. layer was extracted two more times with EA and the combined org. layers were washed with water (3×) and brine, dried over $MgSO_4$ and concentrated under reduced pressure. The residue was purified by CC.

General Method C: Mesylate Formation:

TEA or DIPEA (2 eq.) and MsCl (1.2 eq.) are added at 0° C. to a solution of the required alcohol (1 eq.) in DCM or DCE. The reaction is stirred 1 h at this temperature. In the case the resulting mesylate can undergo cyclization to form a tricyclic system, the reaction mixture is further stirred between rt and 45° C. for 6 to 72 h. Sat. aq. $NaHCO_3$ is then added and the mixture is extracted with DCM (3×). The combined org. layers are dried over $MgSO_4$, filtered and concentrated under reduced pressure to afford the desired mesylate which can be used as such in a further step.

General Method D: Oxazolidinone Formation with CDI:

A solution of the required aminoalcohol (1 eq.) in THF is treated with CDI (1.5 eq.) and heated at 50° C. overnight. The mixture is cooled to rt, diluted with EA and washed with water. The org. layer is washed with 0.5M HCl (optionally) and water, dried over $MgSO_4$ and concentrated. The residue is either triturated with an org. solvent, crystallized from Hept/EA or purified by CC.

General Method E: Deprotection of TBDMS Ethers:

A solution of TBDMS ether (1 eq) in THF is treated with TBAF (1M solution in THF, 1.2 eq.) at 0° C. The solution is stirred at 0° C. for 6 h. The mixture is partitioned between water and EA and the aq. phase is extracted with EA (3×). The combined org. layers are washed with water (3×) and brine, dried over $MgSO_4$ and concentrated under reduced pressure. The residue is triturated with an org. solvent or purified by CC.

General Method F: Asymmetric Dihydroxylation (*Chem. Rev.* (1994), 94, 2483):

A mixture of olefin (1 mmol) in tBuOH/1120 (1:1, 10 mL) at rt is treated with methylsulfonamide (1 eq.) and AD-mix α or AD-mix β (1.5 g). The mixture is vigorously stirred at rt until completion of reaction, $Na_2S_2O_3$ (1.5 g) is added and the mixture diluted with EA (30 mL). The phases are separated and the aq. phase is extracted once more with EA. The combined org. layers are washed with water and brine, dried over $MgSO_4$ and concentrated. The residue is purified by CC.

General Method G: TBDMS Protection:

A solution of alcohol (1 eq.) and imidazole (1.1 eq) in THF (10 mL/mmol) at 0° C. is treated dropwise with a solution of TBDMSCl (1 eq.) in THF. The mixture is stirred at rt until complete conversion. The mixture is diluted with EA, washed with water and brine, dried over $MgSO_4$ and concentrated. The residue is purified by CC.

PREPARATIONS

Preparation A: (2R)-2-aminomethyl-9-fluoro-1,2-dihydro-pyrrolo[3,2,1-ij]quinolin-4-one A.i. (7-fluoro-2-methoxy-quinolin-8-yl)-methanol A suspension of 8-bromomethyl-7-fluoro-2-methoxy-quinoline (25 g, 92.56 mmol) in acetone (360 mL) and water (460 mL) was treated with $NaHCO_3$ (12.74 g, 151.64 mmol, 1.6 eq). The mixture was heated to reflux overnight. After cooling, the volatiles were removed in vacuo and the residue was partitioned between EA (300 mL) and water (100 mL). The aq. layer was extracted once with EA (250 mL) and the combined org. layers were washed with brine, dried over $Na_2SO_4$, filtered and concentrated to dryness. The residue was purified by CC (Hept-EA 3:1) to afford the title alcohol as a yellowish solid (14.04 g).

$^1$H NMR (d6-DMSO) δ: 8.24 (d, J=8.0 Hz, 1H); 7.88 (dd, J=6.4, 9.1 Hz, 1H); 7.31 (t, J=9.1 Hz, 1H); 6.98 (d, J=8.8 Hz, 1H); 5.01 (dd, J=2.1, 5.9 Hz, 2H); 4.86 (t, J=5.9 Hz, 1H); 4.02 (s, 3H).

A.ii. 7-fluoro-2-methoxy-quinoline-8-carbaldehyde

To a solution of oxalyl chloride (17.2 mL, 203.28 mmol) in DCM (360 mL), cooled to −78° C., was added dropwise a solution of DMSO (17.3 mL) in DCM (150 mL) over 45 min. The mixture was stirred 15 min before a solution of intermediate A.i (14.04 g, 67.76 mmol) in DCM (400 mL) was added dropwise over 2 h. The mixture was further stirred 1 h at this temperature. A solution of TEA (70.83 mL, 508.2 mmol, 7.5 eq) in DCM (150 mL) was added dropwise over 1 h 15. The mixture was stirred 30 min before warming gradually to rt. The reaction was quenched adding a sat. $NaHCO_3$ solution (500 mL). The two layers were separated and the org. layer was dried over $Na_2SO_4$, filtered and concentrated to dryness. The residue was dissolved in EA and was purified by CC (EA) affording the aldehyde as a yellowish solid (13.9 g, quant.).

$^1$H NMR (d6-DMSO) δ: 11.12 (dd, J=0.6, 1.5 Hz, 1H); 8.35 (d, J=8.8 Hz, 1H); 8.25 (dd, J=5.9, 9.1 Hz, 1H); 7.42 (ddd, J=0.6, 9.1, 10.8 Hz, 1H); 7.11 (d, J=8.8 Hz, 1H); 4.03 (s, 3H).

MS (ESI, m/z): 206.1 [M+H$^+$].

A.iii. (E)-3-(7-fluoro-2-methoxy-quinolin-8-yl)-acrylic acid ethyl ester

To a suspension of NaH (60% dispersion in oil, 4.25 g, 106.18 mmol) in THF (336 mL) cooled to 0° C., was added triethyl-phosphonoacetate (21.5 mL, 106.18 mmol, 1.1 eq). The mixture was stirred at 0° C. for 30 minutes. Intermediate A.ii (19.81 g, 96.52 mmol) in THF (180 mL) was added at 0° C. The reaction proceeded at 0° C. for 1 h. Water (300 mL) and EA (150 mL) were added. The two layers were decanted and the aq. layer was extracted once with EA (150 mL). The combined org. layers were washed with brine (250 mL) and dried over $Na_2SO_4$. The org. solution was purified by CC to afford after evaporation to dryness the title ester as a yellow thick oil (30 g).

$^1$H NMR (CDCl$_3$) δ: 8.67 (d, J=16.5 Hz, 1H); 7.96 (d, J=9.0 Hz, 1H); 7.70 (dd, J=6.0, 9.0 Hz, 1H); 7.21 (d, J=16.5 Hz, 1H); 7.18 (dd, J=9.3, 10.5 Hz, 1H); 6.91 (d, J=9.3 Hz, 1H); 4.30 (q, J=7.2 Hz, 2H), 4.13 (s, 3H); 1.36 (t, J=7.2 Hz, 3H).

A.iv. (2S,3R)-3-(7-fluoro-2-methoxy-quinolin-8-yl)-2,3-dihydroxy-propionic acid ethyl ester To a suspension of intermediate A.iii (26.57 g, 96.52 mmol) in 2-methyl-2-propanol (440 mL), water (510 mL) and EA (70 mL) were added potassium ferricyanide (95.34 g, 289.57 mmol), $K_2CO_3$ (40.02 g, 289.57 mmol), methanesulfonamide (10.1 g, 106.18 mmol), $(DHQD)_2PHAL$ (0.83 g, 1.06 mmol) and potassium osmate dihydrate (0.18 g, 0.49 mmol). The mixture was stirred at rt overnight. Sodium bisulfite (72 g) was added portionwise. After stirring for 30 min at rt, the two layers were decanted, then the aq. layer was extracted with EA (3×250 mL). The combined org. layers were washed with brine (200 mL), dried over $Na_2SO_4$, filtrated and concentrated to dryness. The residue was purified by CC (Hept-EA 2:1 to EA) to afford the title compound as a yellowish oil (24 g, 80% yield).

$^1$H NMR (CDCl$_3$) δ: 7.99 (d, J=9.3 Hz, 1H); 7.91 (d, J=9.6 Hz, 1H); 7.67 (dd, J=5.7, 8.7 Hz, 1H); 7.17 (dd; J=8.7, 9.3 Hz, 1H); 6.90 (d, J=9.0 Hz, 1H); 5.77 (ddd, J=1.5, 3.3, 9.6 Hz, 1H); 4.72 (br. s, 1H); 4.49 (dd, J=3.3, 6.6 Hz, 1H); 4.09-4.25 (m, 2H); 4.04 (s, 3H); 1.23-1.38 (m, 3H).

A.v. (4S,5R)-5-(7-fluoro-2-methoxy-quinolin-8-yl)-2-oxo-[1,3]dioxolane-4-carboxylic acid ethyl ester To an ice-chilled solution of intermediate A.iv (24 g, 77.6 mmol) and pyridine (37.46 mL, 465.58 g, 6 eq) in DCM (700 mL) was added triphosgene (11.75 g, 38.8 mmol). The reaction proceeded 25 min at 0° C. The reaction mixture was diluted with NaHCO$_3$ (300 mL) and the two layers were decanted. The aq. layer was extracted with DCM (2×150 mL). The combined org. layers were washed with brine (250 mL), dried over Na$_2$SO$_4$, filtered and concentrated to dryness. The residue was co-evaporated twice with toluene (2×150 mL) The residue was dissolved in EA and was purified by CC (EA) to afford after evaporation, the title carbonate as a yellowish solid (19.84 g, 76% yield).

$^1$H NMR (CDCl$_3$) δ: 7.99 (d, J=9.0 Hz, 1H); 7.80 (dd, J=6.3, 9.0 Hz, 1H); 7.19 (t, J=9.0 Hz, 1H); 6.92 (d, J=9.0 Hz, 1H); 6.39 (d, J=6.6 Hz, 1H); 5.56 (d, J=6.6 Hz, 1H); 4.28-4.41 (m, 2H); 4.07 (s, 3H); 1.30-1.35 (m, 3H).

MS (ESI, m/z): 336.1 [M+H$^+$].

A.vi. 3-(7-fluoro-2-methoxy-quinolin-8-yl)-propionic acid ethyl ester (A.vi.a) and (2S)-3-(7-Fluoro-2-methoxy-quinolin-8-yl)-2-hydroxy-propionic acid ethyl ester (A.vi.b)

To a solution of intermediate A.v (9.6 g, 28.66 mmol) in EA (94 mL) and MeOH (14 mL), evacuated twice and backfilled with nitrogen, was carefully introduced Pd/C (10%, 8.83 g). The mixture was evacuated twice and backfilled with nitrogen. The same operation was conducted with hydrogen. The reaction mixture was stirred at 65° C. for 3 h. After cooling, the catalyst was removed by filtration and the filtrate was concentrated to dryness. The residue was purified by CC (Hept-EA 4:1 to 2:1) to afford first the alkane A.vi.a (2.97 g, 37% yield) as a colourless oil and then the alcohol A.vi.b (2.32 g, 28% yield) as a colourless oil.

Alkane A.vi.a:
$^1$H NMR (CDCl$_3$) δ: 7.93 (d, J=9.0 Hz, 1H); 7.56 (dd, J=6.6, 9.0 Hz, 1H); 7.12 (app. t, J=9.0 Hz, 1H); 6.84 (d, J=9.0 Hz, 1H), 4.11 (q, J=7.2 Hz, 2H); 4.06 (s, 3H); 3.47-3.53 (m, 2H); 2.75-2.78 (m, 2H); 1.20 (t, J=7.2 Hz, 3H).

MS (ESI, m/z): 278.3 [M+H$^+$].

Alcohol A.vi.b.:
$^1$H NMR (CDCl$_3$) δ: 7.97 (d, J=9.0 Hz, 1H); 7.60 (dd, J=6.0, 9.0 Hz, 1H); 6.86 (d, J=9.0 Hz, 1H); 4.62-4.70 (m, 2H); 4.06-4.22 (m, 2H); 4.09 (s, 3H); 3.57-3.72 (m, 2H); 1.55 (t, J=7.2 Hz, 3H).

MS (ESI, m/z): 294.2 [M+H$^+$].

A.vii. (S)-3-(7-fluoro-2-methoxy-quinolin-8-yl)-2-methanesulfonyloxy-propionic acid ethyl ester To a solution of intermediate A.vi.b (1.5 g, 5.11 mmol) in DCM (30 mL) cooled to 0° C., were added TEA (0.93 mL, 6.65 mmol) and MsCl (0.48 mL, 6.14 mmol). The reaction mixture was then stirred at the same temperature for 20 min. DCM (30 mL) and a sat. aq. NaHCO$_3$ solution (23 mL) were added. The org. layer was dried over Na$_2$SO$_4$, filtered and concentrated to dryness to afford the title mesylate as an off-white solid (1.92 g, quant.).

$^1$H NMR (CDCl$_3$) δ: 7.96 (d, J=8.7 Hz, 1H); 7.64 (dd, J=6.3, 8.7 Hz, 1H); 7.15 (app. t, J=9.3 Hz, 1H); 6.89 (d, J=8.7 Hz, 1H); 5.61 (dd, J=6.0, 8.4 Hz, 1H); 4.16 (q, J=7.2 Hz, 2H); 4.10 (s, 3H); 3.87 (ddd, J=1.8, 6.0, 13.5 Hz, 1H); 3.68 (ddd, J=1.5, 8.4, 13.5 Hz, 1H); 2.86 (s, 3H); 1.14 (t, J=7.2 Hz, 1H).

MS (ESI, m/z): 372.2 [M+H$^+$].

A.viii. (R)-9-fluoro-4-oxo-1,2-dihydro-4H-pyrrolo[3,2,1-ij]quinoline-2-carboxylic acid ethyl ester A solution of intermediate A.vii (1.93 g, 5.2 mmol) in toluene (27 mL) was heated at reflux for 20 h. The reaction mixture was concentrated to dryness and the residue was chromatographed (EA-Hept: 2-1) to afford the title ester as a white solid (1.31 g, 97% yield).

$^1$H NMR (CDCl$_3$) δ: 7.68 (d, J=9.3 Hz, 1H); 7.40 (dd, J=4.8, 9.0 Hz, 1H); 6.88 (dd, J=8.7, 9.3 Hz, 1H); 6.61 (d, J=9.3 Hz, 1H); 5.36 (dd, J=4.8, 10.5 Hz, 1H); 4.28 (q, J=7.2 Hz, 2H); 3.78 (dddd, J=1.2, 1.5, 10.5, 17.1 Hz, 1H); 3.42 (dddd, J=0.9, 1.2, 4.8, 17.1 Hz, 1H).

MS (ESI, m/z): 262.1 [M+H$^+$].

A.ix. (R)-9-fluoro-2-hydroxymethyl-1,2-dihydro-pyrrolo[3,2,1-ij]quinolin-4-one

To a mixture of intermediate A.viii (1.31 g, 5.02 mmol) in THF (61 ml) cooled to −10° C., was added LiAlH$_4$ (0.381 g, 10.04 mmol, 2 eq). The reaction mixture was stirred at this temperature for 5 min. A sat. Na$_2$SO$_4$ solution (7.87 mL) was added. The resulting solids were filtered off and washed with EA. The filtrate was concentrated to dryness and chromatographed (EA 100% to EA-MeOH 95:5) to afford the title alcohol as a reddish solid (0.478 g, 44% yield).

$^1$H NMR (CDCl$_3$) δ: 7.72 (d, J=9.3 Hz, 1H); 7.42 (dd, J=4.8, 9.0 Hz, 1H); 6.93 (t, J=9.3 Hz, 1H); 6.67 (d, J=9.3 Hz, 1H); 5.68 (dd, J=3.38, 8.4 Hz, 1H); 5.14 (m, 1H); 3.94-4.05 (m, 2H); 3.63 (dddd, J=1.2, 1.5, 9.9, 17.1 Hz, 1H); 3.03 (dddd, J=0.9, 1.2, 6.6, 17.1 Hz, 1H).

MS (ESI, m/z): 220.2 [M+H$^+$].

A.x. (R)-methanesulfonic acid 9-fluoro-4-oxo-1,2-dihydro-4H-pyrrolo[3,2,1-ij]quinolin-2-ylmethyl ester Starting from intermediate A.ix (0.478 g, 2.11 mmol), the title mesylate was obtained as an orange solid (0.65 g, 100% yield) using the procedure described in Preparation A, step A.vii.

MS (ESI, m/z): 298.2 [M+H$^+$].

A.xi. (2R)-2-azidomethyl-9-fluoro-1,2-dihydro-pyrrolo[3,2,1-ij]quinolin-4-one

To a solution of intermediate A.x (0.65 g, 2.18 mmol) in DMF (10 mL) was added NaN$_3$ (0.430 g, 3 eq.). The mixture was heated at 80° C. for 2 h. The reaction mixture was cooled to rt. The solvent was evaporated. The residue was partitioned between water (40 mL) and EA (30 mL). The phases were separated and the aq. layer was extracted twice with EA (2×30 mL). The combined org. layers were dried over MgSO$_4$, filtered and evaporated under reduced pressure. The residue was purified by CC (EA-Hept 2-1) to afford the title azide as a yellowish oil (0.435 g, 80% yield).

$^1$H NMR (CDCl$_3$) δ: 7.68 (d, J=9.3 Hz, 1H); 7.38 (dd, J=4.8, 8.7 Hz, 1H); 6.89 (app. t, J=9.0 Hz, 1H); 6.57 (d, J=9.3

Hz, 1H); 5.13 (m, 1H); 4.29 (dd, J=4.8, 12.3 Hz, 1H); 3.74 (dd, J=2.7, 12.3 Hz, 1H); 3.55 (dd, J=9.9, 17.1 Hz, 1H); 3.34 (dd, J=4.2, 17.1 Hz, 1H).

MS (ESI, m/z): 245.0 [M+H$^+$].

A.xii. (2R)-2-aminomethyl-9-fluoro-1,2-dihydro-pyrrolo[3,2,1-ij]quinolin-4-one To a solution of intermediate A.xi (0.43 g, 1.77 mmol) in THF (22 mL) was added PPh$_3$ (0.320 g, 0.90 mmol). The mixture was heated at 60° C. for 30 min, and water (4 mL) was added. The resulting mixture was heated at 60° C. for 2 h. Water (2 mL) was added and the reaction was stirred for 1 h at the same temperature. The reaction mixture was concentrated to dryness and the residue was purified by CC (DCM-MeOH 93:7 containing 0.7% NH$_4$OH to DCM-MeOH 9:1 containing 1% aq. NH$_4$OH) to afford the title amine as an off-white solid (0.363 g).

$^1$H NMR (CDCl$_3$) δ: 7.65 (d, J=9.3 Hz, 1H); 7.35 (dd, J=4.8, 8.7 Hz, 1H); 6.86 (app. t, J=9.0 Hz, 1H); 6.57 (d, J=9.3 Hz, 1H); 5.01 (m, 1H); 3.54 (dddd, J=1.2, 1.5, 9.6, 16.8 Hz, 1H); 3.35 (dd, J=5.7, 13.2 Hz, 1H); 3.33 (overlapped dddd, J=0.9, 1.2, 4.5, 16.8 Hz, 1H); 3.23 (dd, J=3.6, 13.2 Hz, 1H); 1.31 (br. s, 2H).

MS (ESI, m/z): 262.1 [M+H$^+$].

Preparation B: (2RS)-2-aminomethyl-9-fluoro-1,2-dihydro-pyrrolo[3,2,1-ij]quinolin-4-one

B.i. (2RS)-2-bromo-3-(7-fluoro-2-methoxy-quinolin-8-yl)-propionic acid ethyl ester To a solution of DIPA (1.9 mL, 13.5 mmol) in THF (25 mL) cooled to −78° C. was added nBuLi (1.74N, 7.7 mL, 13.4 mmol). The mixture was stirred 5 min at this temperature before warming to 0° C. The mixture was stirred 15 min before cooling again to −78° C. After 5 min, a solution of intermediate A.vi.a (3.1 g, 11.17 mmol) in THF (25 mL) was added dropwise. The solution was stirred for 90 min at this temperature. To the solution were added successively freshly distilled TMSCl (2.83 mL, 22.3 mmol) and a solution of PTT (6.3 g, 16.7 mmol) in THF (20 mL), keeping the internal temperature below −40° C. The solution was stirred 30 min at −78° C. then warmed to rt. Water (20 mL) and 10% NaHSO$_4$ (10 mL) were added the phases were separated and the aq. layer was extracted twice with EA (2×50 mL). The residue was purified by CC (EA-Hept 1:4) to give the bromide as a brown oil (3.6 g, 90% yield). $^1$H NMR (CDCl$_3$) δ: 7.95 (d, J=8.8 Hz, 1H); 7.63 (dd, J=5.9, 8.8 Hz, 1H); 7.14 (t, J=8.8 Hz, 1H); 6.87 (d, J=8.8 Hz, 1H); 5.03 (t, J=7.8 Hz, 1H); 4.17 (qd, J=2.3, 7.3 Hz, 2H); 4.08 (s, 3H); 3.97 (ddd, J=1.2, 7.8, 13.8 Hz, 1H); 3.84 (ddd, J=1.5, 7.8, 13.8 Hz, 1H); 1.20 (t, J=7.3 Hz, 3H).

B.ii. (2RS)-9-fluoro-4-oxo-1,2-dihydro-4H-pyrrolo[3,2,1-ij]quinoline-2-carboxylic acid ethyl ester A solution of intermediate B.i (3.60 g, 10.1 mmol) in toluene (25 mL) was heated to reflux for 5 h. After cooling to rt, the reaction mixture was concentrated to dryness and the residue was purified by CC (Hept-EA 1:1) to afford the title compound as a white solid (2.05 g, 78% yield).

$^1$H NMR (CDCl$_3$) δ: 7.68 (d, J=9.3 Hz, 1H); 7.40 (dd, J=4.8, 9.0 Hz, 1H); 6.88 (dd, J=8.7, 9.3 Hz, 1H); 6.61 (d, J=9.3 Hz, 1H); 5.36 (dd, J=4.8, 10.5 Hz, 1H); 4.28 (q, J=7.2 Hz, 2H); 3.78 (dddd, J=1.2, 1.5, 10.5, 17.1 Hz, 1H); 3.42 (dddd, J=0.9, 1.2, 4.8, 17.1 Hz, 1H).

B.iii. (2RS)-2-aminomethyl-9-fluoro-1,2-dihydro-pyrrolo[3,2,1-ij]quinolin-4-one Starting from intermediate B.ii (2.0 g, 7.65 mmol), the title amine (0.484 g, 2.2 mmol) was obtained as a yellowish solid using the procedures of Preparation A, steps A.ix to A.xii.

MS (ESI, m/z): 262.1 [M+H$^+$].

Preparation C: (2RS)-2-aminomethyl-2,3-dihydro-1-oxa-3a-aza-phenalen-4-one

C.i. 2-(2-methoxy-quinolin-8-yloxy)-malonic acid diethyl ester

To a solution of 2-methoxy-quinolin-8-ol (commercial; 1.75 g, 10 mmol) and diethyl bromomalonate (1.85 mL, 10 mmol) in DMF (35 mL) was added Cs$_2$CO$_3$ (6.52 g, 20 mmol). The reaction mixture was heated at 80° C. for 1.5 h then allowed to cool to rt. The reaction mixture was filtered and the filtrate concentrated to dryness. The residue was purified by CC (EA-Hept 1:3 to 1:1) to give the title compound as a yellowish oil (2.50 g, 75% yield).

$^1$H NMR (CDCl$_3$) δ: 7.98 (d, J=8.7 Hz, 1H); 7.49 (m, 1H); 7.47 (m, 1H); 7.29 (d, J=8.1 Hz, 1H); 6.90 (d, J=8.7 Hz, 1H); 6.00 (s, 1H); 4.26-4.39 (m, 4H); 4.05 (s, 3H); 1.31 (t, J=7.2 Hz, 6H).

MS (ESI, m/z): 334.1 [M+H$^+$].

C.ii. 2-(2-methoxy-quinolin-8-yloxy)-propane-1,3-diol

To an ice-chilled solution of intermediate C.i. (2.50 g, 7.49 mmol) in THF (60 mL) was added LiAlH$_4$ (0.852 g, 22.46 mmol) portionwise. The reaction mixture was stirred at this temperature for 2 h 20, then 10 minutes at rt before cooling to 0° C. The reaction mixture was diluted with THF (20 mL) and a sat. Na$_2$SO$_4$ solution (3.6 mL) was added. The suspension was filtered and the filtrate was evaporated under reduced pressure. The residue was purified by CC (EA-Hept 2:1 to 4:1) to give the title compound as a yellowish oil (0.567 g, 30% yield).

$^1$H NMR (CDCl$_3$) δ: 8.1 (d, J=8.7 Hz, 1H); 7.50 (dd, J=1.5, 7.8 Hz, 1H); 7.45 (dd, J=1.5, 7.8 Hz, 1H); 7.35 (t, J=7.8 Hz, 1H); 6.94 (d, J=9.0 Hz, 1H); 4.29 (m, 1H); 4.09 (s, 3H); 394 (dd, J=5.7, 12.3 Hz, 2H); 3.82 (dd, J=3.6, 12.3 Hz, 2H); 3.81 (overlapped br. s, 2H).

MS (ESI, m/z): 250.2 [M+H$^+$].

C.iii. Methanesulfonic acid 3-methanesulfonyloxy-2-(2-methoxy-quinolin-8-yloxy)-propyl ester To an ice-chilled solution of intermediate C.ii (0.567 g, 2.27 mmol) in DCM (25 mL) were added TEA (1.268 mL, 9.10 mmol) and MsCl (0.388 mL, 1.48 mmol). The reaction was stirred for 40 min at the same temperature, then at rt for 5 min. The reaction mixture was partitioned between sat. NaHCO$_3$ (30 mL) and DCM (15 mL). The aq. layer was extracted once with DCM (20 mL). The combined org. layers were dried over Na$_2$SO$_4$, filtered and concentrated to dryness. The residue was purified by CC (DCM-MeOH 99:1 then 98:2) to give the title mesylate as a yellowish foam (0.605 g, 66% yield).

$^1$H NMR (CDCl$_3$) δ: 8.00 (d, J=8.7 Hz, 1H); 7.51 (dd, J=1.8, 7.5 Hz, 1H); 7.35 (dd, J=1.8, 7.5 Hz, 1H); 7.31 (t, J=7.5 Hz, 1H); 6.94 (d, J=9.0 Hz, 1H); 5.23 (pent., 4.8 Hz, 1H); 4.67 (ddd, AB system, J=5.1, 11.1 Hz, Δ=0.044 ppm, 4H); 4.07 (s, 3H); 3.09 (s, 6H).

MS (ESI, m/z): 406.1 [M+H$^+$].

C.iv. (2RS)-methanesulfonic acid 4-oxo-2,3-dihydro-4H-1-oxa-3a-aza-phenalen-2-ylmethyl ester A solution of intermediate C.iii (0.606 g, 1.49 mmol) in toluene (15 mL) was heated at reflux overnight. After cooling to rt, the mixture was concentrated to dryness. The residue was purified by CC (DCM-MeOH 98:2 to 19:1) to give the title compound as an off-white solid (0.387 g).

$^1$H NMR (d6-DMSO) δ: 7.93 (d, J=9.6 Hz, 1H); 7.33 (dd, J=2.4, 6.6 Hz, 1H); 7.13-7.19 (m, 2H); 6.62 (d, J=9.6 Hz, 1H); 4.561-4.68 (m, 4H); 3.60 (dd, J=8.7, 13.8 Hz, 1H); 3.26 (s, 3H).

MS (ESI, m/z): 296.3 [M+H$^+$].

C.v. (2RS)-2-azidomethyl-2,3-dihydro-1-oxa-3a-aza-phenalen-4-one

To a solution of intermediate C.iv (0.387 g, 1.31 mmol) in DMF (3.7 mL) was added sodium azide (0.213 g, 3.27 mmol). The reaction mixture was heated at 70° C. for 20 h. After cooling, the reaction mixture was diluted with water (10 mL) and extracted with EA (3×20 mL). The combined org. layers were washed with brine (20 mL), dried over Na$_2$SO$_4$, filtered and concentrated to dryness to give the title compound as a yellowish solid (0.307 g, 97% yield).

$^1$H NMR (d6-DMSO) δ: 7.92 (d, J=9.6 Hz, 7.33 (dd, J=3.0, 6.3 Hz, 1H); 7.12-7.18 (m, 2H); 6.61 (d, J=9.6 Hz, 1H); 4.53 (dd, J=2.7, 13.8 Hz, 1H); 4.44 (m, 1H); 3.80 (dd, J=3.3, 13.5 Hz, 1H); 3.71 (dd, J=6.3, 13.5 Hz, 1H); 3.59 (dd, J=9.0, 13.8 Hz, 1H).

MS (ESI, m/z): 243.2 [M+H$^+$].

C.vi. (2RS)-2-aminomethyl-2,3-dihydro-1-oxa-3a-aza-phenalen-4-one

To a solution of intermediate C.v. (0.307 g, 0.60 mmol) in THF (15 mL) were added PPh$_3$ (0.684 g, 2.53 mmol) and water (2.3 mL). The mixture was heated at 60° C. for 2 h. The volatiles were removed under reduced pressure and the residue was diluted with DCM-MeOH 9:1 (10 mL) and aq. sat. NaHCO$_3$ (5 mL). The aq. layer was treated with 2M NaOH until pH 12 was reached. The phases were separated and the aq. layer was extracted six times with DCM-MeOH 9:1 (6×10 mL). The combined org. layers were dried over MgSO$_4$, filtered and evaporated under reduced pressure. The residue was purified by CC (DCM-MeOH 93:7 containing 0.7% aq. NH$_4$OH) to give the title amine as an off-white solid (0.188 g, 69% yield).

$^1$H NMR (d6-DMSO) δ: 7.90 (d, J=9.3 Hz, 1H); 7.29 (dd, J=3.0, 6.6 Hz, 1H); 7.09-7.16 (m, 2H); 6.60 (d, J=9.3 Hz, 1H); 4.60 (dd, J=2.7, 14.1 Hz, 1H); 4.05 (m, 1H); 3.50 (dd, J=9.3, 14.1 Hz, 1H); 2.91 (qd, J=5.7, 13.5 Hz, 2H); 1.62 (br. s, 2H).

MS (ESI, m/z): 217.4 [M+H$^+$].

Preparation D: (2RS)-2-aminomethyl-9-fluoro-2,3-dihydro-1-oxa-3a-aza-phenalen-4-one

D.i. 1-fluoro-2-benzyloxy-3-nitro-benzene

To a solution of 2-fluoro-6-nitrophenol (25.1 g, 157 mmol) in DMF (430 mL) were added K$_2$CO$_3$ (43.7 g, 313 mmol) and benzyl bromide (21 mL, 172 mmol). The reaction mixture was stirred at 80° C. overnight. After cooling to rt, the reaction mixture was filtered. The filtrate was concentrated under reduced pressure. Water (100 mL) and EA (100 mL) were added and the phases were separated. The aq. layer was extracted once with EA (100 mL) and the combined org. layers were dried over Na$_2$SO$_4$, filtered and evaporated under reduced pressure. The residue was dried under HV to give the title compound as a yellow oil (39.9 g).

$^1$H NMR (d6-DMSO) δ: 7.65-7.75 (m, 2H); 7.28-7.40 (m, 6H); 5.21 (s, 2H).

D.ii. 3-fluoro-2-benzyloxy-phenylamine

To a solution of intermediate D.i. (11.1 g, 45 mmol) in MeOH (215 mL) at was added Zn dust (29.4 g, 449 mmol) at rt. The mixture was stirred for 5 min and an aq. sat. NH$_4$Cl solution (600 mL) was added slowly over 1 h. After the addition was complete, sat. NH$_4$Cl (250 mL) was added. The reaction was stirred for 2 h. The solids were filtered over Celite, washed with MeOH and the filtrate was evaporated. The aq. residue was diluted with DCM-MeOH (9:1, 200 mL) and the pH of the aq. layer was adjusted to 12, adding 32% aq. NaOH. The phases were separated and the aq. layer was extracted twice more with DCM-MeOH (9:1, 2×200 mL). The combined org. layers were dried over MgSO$_4$, filtered and evaporated under reduced pressure to give the title compound as a yellow oil (9.43 g, 97% yield).

$^1$H NMR (d6-DMSO) δ: 7.44-7.49 (m, 2H); 7.29-7.39 (m, 3H); 6.74 (td, J=6.0, 8.1 Hz, 1H); 6.47 (td, J=1.2, 8.1 Hz, 1H); 6.33 (ddd, J=1.5, 8.1, 11.1 Hz, 1H); 5.07 (br. s, 2H); 4.92 (s, 2H).

D.iii. (E)-N-(2-benzyloxy-3-fluoro-phenyl)-3-ethoxy-acrylamide

To an ice chilled solution of intermediate D.ii (9.43 g, 43.4 mmol) in DCM (70 mL) was added pyridine (7 mL). A solution of crude (E)-3-ethoxy-acryloyl chloride (8 g; prepared as described in *J. Med. Chem.* (2005), 48, 306) in DCM (40 mL) was added dropwise and the reaction proceeded for 2 h. Sat. NaHCO$_3$ (75 mL) was added. The two layers were decanted and the aq. layer was extracted once with DCM (100 mL). The combined org. layers were dried over Na$_2$SO$_4$, filtered and concentrated to dryness. The residue was co-evaporated twice with toluene and the residue was purified by CC (Hept-Ea 3:1) to afford the title compound as a yellowish oil (11.4 g, 83% yield).

MS (ESI, m/z): 316.1 [M+H$^+$].

D.iv. 7-fluoro-8-hydroxy-1H-quinolin-2-one

To intermediate D.iii (11.4 g, 36.15 mmol), was added sulfuric acid (95-97%, 80 mL, precooled to 0° C.). The mixture was stirred 15 min and poured onto an ice-water mixture (500 mL). The mixture was diluted with EA (500 mL) and 32% aq. NaOH. The two phases were separated. The aq. layer was further extracted with EA (3×200 mL). The combined org. layers were washed with brine, dried over Na$_2$SO$_4$, filtered and concentrated to dryness. The residue was triturated in ether and the solid filtered to yield the title compound as a light beige solid (3.58 g, 55% yield).

MS (ESI, m/z): 180.1 [M+H$^+$].

D.v. 8-benzyloxy-7-fluoro-1H-quinolin-2-one

To a mixture of intermediate D.iv. (4.6 g, 25.67 mmol) in 2-propanol (60 mL) were added DBU (5.8 mL, 38.6 mmol) and BnBr (3.4 mL, 28.5 mmol). The mixture was heated to 80° C. for 90 min. After cooling, the solvent was evaporated and the residue was taken up in EA (200 mL) and water (100 mL). The aq. layer was extracted once with EA (100 mL). The combined org. layers were filtered through a pad of silica gel. The filtrate was evaporated and the residue was recrystallized from EA-Hept to yield after filtration, the title compound as a beige solid (3.58 g).

MS (ESI, m/z): 270.1 [M+H$^+$].

D.vi. 8-benzyloxy-2-chloro-7-fluoro-quinoline

A mixture of intermediate D.v (3.58 g) in phosphorous oxychloride (20 mL) was heated to 80° C. for 90 min. The solvent was evaporated and the residue was taken up in DCM (100 mL) and water (100 mL). After stirring 1 h at rt, the pH of the aq. layer was adjusted to 10 adding solid $Na_2CO_3$. The two layers were decanted and the aq. layer was extracted once with DCM (50 mL). The combined org. layers were dried over $Na_2SO_4$, filtered and concentrated to dryness. The residue was purified by CC (Hept-EA 1:1) to afford the title compound as a beige solid (3.4 g, 89% yield).

MS (ESI, m/z): 288.1 [M+H$^+$].

D.vii. 8-benzyloxy-7-fluoro-2-methoxy-quinoline

A mixture of intermediate D.vi (3.4 g, 11.81 mmol) in toluene (7 mL) was treated with 25 wt % NaOMe in MeOH (30 mL) at 70° C. for 2 h. The reaction mixture was diluted with water (200 mL) and DCM (300 mL). The pH of the aq. layer was adjusted to 2 adding 10% aq. $NaHSO_4$. The two layers were decanted and the aq. layer was extracted once with DCM (100 mL). The combined org. layers were dried over $Na_2SO_4$, filtered and concentrated to dryness. The residue was purified by CC (EA) to afford the title compound as a beige oil (3.38 g, 100% yield).

$^1$H NMR (CDCl$_3$) δ: 7.93 (d, J=9.0 Hz, 1H); 7.57-7.60 (m, 2H); 7.30-7.40 (m, 4H); 7.16 (dd, J=9.0, 9.3 Hz, 1H); 6.87 (d, J=9.3 Hz, 1H); 5.48 (s, 2H); 4.10 (s, 3H).

MS (ESI, m/z): 284.1 [M+H$^+$].

D.viii. 7-fluoro-2-methoxy-quinolin-8-ol

To a solution of intermediate D.vii (3.38 g, 11.9 mmol) in EtOH (35 mL) was added 10% Pd/C (0.48 g). The reaction was stirred under hydrogen atmosphere for 2 h. The catalyst was removed by filtration and the filtrate was concentrated to dryness. The residue was dried under HV to give the title compound as an off-white solid (2.2 g, 95% yield).

$^1$H NMR (d6-DMSO) δ: 9.35 (s, 1H); 8.16 (d, J=8.7 Hz, 1H); 7.25-7.35 (m, 2H); 6.94 (d, J=8.7 Hz, 1H); 4.05 (s, 3H).

MS (ESI, m/z): 194.2 [M+H$^+$].

D.ix. (2RS)-2-aminomethyl-9-fluoro-2,3-dihydro-4-oxa-3a-aza-phenalen-4 one

Starting from intermediate D.viii (2.0 g, 10.35 mmol) and using the procedures of Preparation C, steps C.i to C.vi, the title amine was obtained as a beige solid (1.04 g, 4.4 mmol).

$^1$H NMR (d6-DMSO) δ: 7.89 (d, J=9.6 Hz, 1H); 7.31 (dd, J=5.4, 8.7 Hz, 1H); 7.14 (dd, J=9.0, 10.8 Hz, 1H); 6.55 (d, J=9.6 Hz, 1H); 4.63 (dd, J=2.7, 14.1 Hz, 1H); 4.11 (m, 1H); 3.53 (dd, J=9.6, 14.1 Hz, 1H); 2.94 (qd, J=5.7, 13.5 Hz, 2H); 1.61 (br. s, 2H).

MS (ESI, m/z): 325.3 [M+H$^+$].

Preparation E: (6RS)-6-amino-8-fluoro-6,7-dihydro-5H-pyrido[3,2,1-ij]quinolin-3-one

E.i. 2-(7-fluoro-2-methoxy-quinolin-8-ylmethyl)-malonic acid diethyl ester

To a suspension of NaH (60% dispersion in oil, 0.88 g, 22 mmol) in THF (100 mL), was added diethyl malonate (3.79 g, 23.66 mmol). The reaction mixture was cooled to 0° C. and 8-bromomethyl-7-fluoro-2-methoxy-quinoline (5.4 g, 20 mmol) was added in one portion. The reaction proceeded 30 min at 0° C. and 15 min at rt. The reaction mixture was quenched by adding water (20 mL) and 10% $NaHSO_4$ (100 mL). The two layers were decanted and the aq. layer was extracted once with EA (100 mL). The combined org. layers were washed with brine, dried over $Na_2SO_4$, filtered and concentrated to dryness. The residue was purified by CC (Hept-EA 4:1) to afford the title compound as a yellowish oil (6.4 g). The product was contaminated with 20% of diethyl malonate.

$^1$H NMR (CDCl$_3$) δ: 7.94 (d, J=8.8 Hz, 1H); 7.58 (dd, J=6.2, 8.8 Hz, 1H); 7.12 (app. t, J=9.1 Hz, 1H); 6.85 (d, J=8.8 Hz, 1H); 4.06-4.18 (m, 5H); 4.06 (s, 3H); 3.75 (dd, J=1.5, 7.6 Hz, 2H); 1.15 (t, J=7.2 Hz, 6H).

E.ii. 2-(7-fluoro-2-methoxy-quinolin-8-ylmethyl)-propane-1,3-diol

To a solution of intermediate E.i (6.4 g) in THF (200 mL), cooled to 0° C., was added LiAlH$_4$ (2.086 g). The reaction mixture was stirred at the same temperature for 25 min. Water (4.8 mL) was carefully added, followed with 2M NaOH (8.7 mL) and water (8.7 mL). After stirring 3 min, $Na_2SO_4$ (solid, 30 g) was added and stirring was maintained for 20 min. The mixture was filtered off and the solids were washed with EA. The filtrate was concentrated to dryness and the residue was purified by CC (DCM-MeOH 97:3) to afford the title compound as a white solid (3.0 g, 62% yield).

MS (ESI, m/z): 266.3 [M+H$^+$].

E.iii. (2RS)-acetic acid 3-(7-fluoro-2-methoxy-quinolin-8-yl)-2-hydroxymethyl-propyl ester To a mixture of intermediate E.ii (3.0 g, 11.3 mmol) in DCM (55 mL) were added at rt TsOH (0.17 g) and trimethylorthoacetate (2.2 mL, 17 mmol). The mixture was stirred at rt for 15 min and water (15 mL) and AcOH (5 mL) were added. The mixture was stirred at it for 20 min. The solvents were evaporated to dryness and the residue was partitioned between sat. NaHCO$_3$ (100 mL) and EA (200 mL). The pH of the aq. layer was adjusted to 9-10 adding sat. NaHCO$_3$. The two layers were separated and the aq. layer was extracted once with EA (100 mL). The combined org. layers were washed with brine and concentrated to dryness to afford the crude monoester as a colourless oil (3.4 g, 98% yield).

MS (ESI, m/z): 308.3 [M+H$^+$].

E.iv. (2RS)-acetic acid 3-(7-fluoro-2-methoxy-quinolin-8-yl)-2-methanesulfonyloxymethylpropyl ester To a solution of intermediate E.iii (3.4 g, 11.3 mmol) in DCM (55 mL), cooled to 0° C., were added TEA (3.1 mL, 22.7 mmol) and MsCl (1.05 mL, 13.6 mmol). The reaction was stirred at 0° C. for 1 h. Sat. NaHCO$_3$ (100 mL) and DCM (200 mL) were added. The two layers were decanted and the org. layer was dried over $Na_2SO_4$, filtered and concentrated to dryness. The residue was filtered quickly through a pad of silica (EA-Hept 3:1) to afford the title compound as a colourless oil (4.5 g, 100% yield).

$^1$H NMR (CDCl$_3$) δ: 7.95 (d, J=9.0 Hz, 1H); 7.60 (dd, J=6.5, 9.0 Hz, 1H); 7.14 (t, J=9.0 Hz, 1H); 6.87 (d, J=9.0 Hz, 1H); 4.31 (dd, J=5.1, 9.6 Hz, 1H); 4.26 (dd, J=5.7, 9.6 Hz, 1H); 4.14-4.22 (m, 2H); 4.07 (s, 3H); 3.28 (app. d, J=6.9 Hz, 2H); 2.98 (s, 3H); 2.78 (m, 1H); 2.04 (s, 3H).

MS (ESI, m/z): 386.1 [M+H$^+$].

E.v. (2RS)-acetic acid 10-fluoro-5-oxo-2,3-dihydro-1H,5H-pyrrolo[3,2,1-ij]quinolin-2-ylmethyl ester A solution of intermediate E.iv (4.5 g, 11.3 mmol) in toluene (100 mL) was refluxed overnight. After cooling, the solvent was evaporated to dryness and the residue was purified by CC (Hept-EA 1:2 then EA) to afford the title compound as a white solid (2.9 g, 90% yield).

$^1$H NMR (CDCl$_3$) δ: 7.62 (d, J=9.4 Hz, 1H), 7.39 (dd, J=6.3, 8.4 Hz, 1H); 6.94 (t, J=8.4 Hz, 1H); 6.64 (d, J=9.4 Hz, 1H); 4.67 (m, 1H); 4.23 (dd, J=5.8, 11.3 Hz, 1H); 4.12 (dd, J=7.2, 11.3 Hz, 1H); 3.62 (dd, J=9.6, 13.8 Hz, 1H); 3.15 (m, 1H); 2.65 (dd, J=9.6, 16.2 Hz, 1H); 2.44 (m, 1H); 2.10 (s, 3H).

MS (ESI, m/z): 276.2 [M+H$^+$].

E.vi. (6RS)-8-fluoro-6-hydroxymethyl-6,7-dihydro-5H-pyrido[3,2,1-ij]quinolin-3-one To a solution of intermediate E.v (2.9 g, 10.53 mmol) in MeOH (45 mL) was added K$_2$CO$_3$ (3 g). The mixture was heated at 50° C. for 30 min. DCM (400 mL) and water (100 mL) were added. The two layers were separated and the org. layer was dried over Na$_2$SO$_4$, filtered and concentrated to dryness. The residue was dried in vacuo to afford the title alcohol as a white solid (2.4 g, 98% yield).

MS (EST, m/z): 234.3 [M+H$^+$].

E.vii. (2RS)-10-fluoro-5-oxo-2,3-dihydro-1H,5H-pyrido[3,2,1-ij]quinoline-2-carboxylic acid To a mixture of intermediate E.vi (1.44 g, 6.17 mmol) in DCM (20 mL), cooled to 0° C., were added DIPEA (3.2 mL, 18.5 mmol) and a solution of Pyr.SO$_3$ (50%, 2.75 g, 8.64 mmol) in DMSO (8.5 mL). The mixture was stirred at 0° C. for 30 min and then to rt for 40 min. Sat. NaHCO$_3$ (120 mL) and DCM (200 mL) were added. The two layers were decanted and the aq. layer was extracted once with DCM (200 mL). The combined org. layers were washed with brine, dried over Na$_2$SO$_4$, filtered and concentrated to dryness, then co-evaporated with toluene. The residue was taken up in 2-methyl-2-propanol (80 mL). 2-methyl-2-butene (24 mL) and a solution of sodium chlorite (8 g) and sodium di-hydrogen phosphate (8 g) in water (55 mL) were added. The mixture was stirred at rt overnight. The solvent was evaporated and the solids were filtered off, washed with water and dried in vacuo to afford the title acid as a white solid (1.35 g, 84% yield).

MS (ESI, m/z): 248.2 [M+H$^+$].

E.viii. (2RS)-(10-fluoro-5-oxo-2,3-dihydro-1H,5H-pyrido[3,2,1-ij]quinolin-2-yl)-carbamic acid tert-butyl ester To a solution of intermediate E.vii (1.35 g, 5.46 mmol) in toluene (22 mL) and 2-methyl-2-propanol (15 mL) were added TEA (0.93 mL, 6.6 mmol) and DPPA (1.30 mL, 6 mmol). The mixture was heated to 90° C. The reaction proceeded 2.5 h at this temperature. The reaction mixture was then cooled to rt, the solids were filtered and the filtrate was evaporated under reduced pressure. The residue was purified by CC (DCM-MeOH 97:3) to afford the title compound as a yellow foam (0.870 g, 50% yield).

MS (ESI, m/z): 319.1 [M+H$^+$].

E.ix. (6RS)-6-amino-8-fluoro-6,7-dihydro-5H-pyrido[3,2,1-ij]quinolin-3-one

A solution of intermediate E.viii (0.870 g, 2.73 mmol) in TFA (16 mL) was stirred at rt for 15 min. The solvent was removed in vacuo and the residue was partitioned between saturated NaHCO$_3$ (70 mL) and DCM-MeOH (9-1, 180 mL). The pH of the aq. layer was 12. The aq. layer was extracted four times with the same mixture (4×70 mL). The combined org. layers were washed with brine (50 mL), dried over Na$_2$SO$_4$, filtered and concentrated to dryness. The residue was chromatographed (DCM-MeOH 97-3 containing 0.3% aq. NH$_4$OH) to afford the title compound (0.345 g, 58% yield) as an off-white solid.

$^1$H NMR (CDCl$_3$) δ: 7.63 (d, J=9.4 Hz, 1H), 7.39 (dd, J=6.1, 8.6 Hz, 1H); 6.94 (t, J=8.6 Hz, 1H); 6.63 (d, J=9.4 Hz, 1H); 4.39 (m, 1H); 3.77 (dd, J=7.8, 13.5 Hz, 1H); 3.54 (m, 1H); 3.18 (m, 1H), 2.73 (dd, J=8.4, 16.2 Hz, 1H); 1.54 (br. s, 2H).

MS (ESI, m/z): 219.1 [M+H$^+$].

Preparation F: (2RS)-2-aminomethyl-2,3-dihydro-1-oxa-3a,7-diaza-phenalen-4-one

F.i. Methanesulfonic acid 3-tert-butoxycarbonylamino-2-hydroxy-propyl ester

A solution of rac-(2,3-dihydroxy-propyl)-carbamic acid tent-butyl ester (commercial; 1.9 g, 10 mmol) in DCM (100 mL) was treated sequentially with TEA (1.5 mL, 11 mmol) and dropwise with MsCl (0.78 mL, 10 mmol). A slightly exothermic reaction occurred and the mixture was stirred at rt for 2 h. The mixture was diluted with DCM, washed with water, dried over MgSO$_4$ and concentrated to give a colourless oil (2.54 g, 94% yield) which was used as such in the next step without further purification.

F.ii. (2RS)-(4-oxo-2,3-dihydro-4H-1-oxa-3a,7-diaza-phenalen-2-ylmethyl)-carbamic acid tent-butyl ester A mixture of intermediate F.i (2.54 g) and 6-methoxy-[1,5]naphthyridin-4-ol (1.76 g, 10 mmol) in THF (100 mL) was treated with PPh$_3$ (2.89 g, 11 mmol) and DIAD (2.18 mL, 11 mmol). The solution was stirred at rt for 6 h, concentrated in vacuo and purified by CC (EA). The intermediate mesylate, which was contaminated with PPh$_3$O was dissolved in toluene (100 mL) and heated at reflux overnight. The mixture was cooled to rt and the solvents were removed under reduced pressure. The residue was dissolved in EA, washed with water and brine, dried over MgSO$_4$ and concentrated. The product was purified by CC (Hep/EA 1:1, EA, EA/MeOH 9:1) to give the desired cyclised product as a colourless solid (0.625 g, 20% yield).

$^1$H NMR (d6-DMSO) δ: 8.32 (d, J=5.3 Hz, 1H), 7.90 (d, J=10.0 Hz, 1H), 7.21 (m, 1H), 7.09 (d, J=5.3 Hz, 1H), 6.84 (d, J=10.0 Hz, 1H), 4.53 (m, 1H), 4.35 (m, 1H), 3.55 (m, 1H), 3.37 (m, 2H), 1.38 (s, 9H).

MS (ESI, m/z): 318.1 [M+H$^+$].

F.iii. (2RS)-2-aminomethyl-2,3-dihydro-1-oxa-3a,7-diaza-phenalen-4-one

A solution of intermediate F.ii (0.6 g, 1.9 mmol) in DCM (4 mL) was treated with TFA (2 mL). The mixture was stirred at rt for 2 h, concentrated in vacuo and partitioned between DCM/MeOH 9:1 and NH$_4$OH (5 mL). The aq. phase was once more extracted with DCM/MeOH 9:1, the combined org. extracts were dried over MgSO$_4$ and concentrated to give the desired intermediate as a colourless solid (0.36 g, 87% yield).

$^1$H NMR (d6-DMSO) δ: 8.33 (d, J=5.3 Hz, 1H), 7.91 (d, J=10.0 Hz, 1H), 7.10 (d, J=5.3 Hz, 1H), 6.85 (d, J=9.7 Hz, 1H), 4.61 (dd, J=14.1, 2.9 Hz, 1H), 4.25 (m, 1H), 3.59 (dd, J=14.1, 9.4 Hz, 1H), 2.96 (m, 2H), 2.33 (m, 2H).

Preparation G: (RS)-6-aminomethyl-8-fluoro-6,7-dihydro-5H-pyrido[3,2,1-ij]quinolin-3-one

G.i. (2RS)-2-(tert-butoxycarbonylamino-methyl)-3-(7-fluoro-2-methoxy-quinolin-8-yl)-propionic acid ethyl ester To a solution of LiHMDS (1M, 20 mL), cooled to −78° C., was added dropwise a solution of 3-tert-butoxycarbonylamino-propionic acid ethyl ester (2.01 g, 9.26 mmol; prepared as in *Tetrahedron Lett.* (2003), 44(14), 2807) in THF (20 mL). The solution was stirred at the same temperature for 90 min. A solution of 8-bromomethyl-7-fluoro-2-methoxy-quinoline (2.5 g; prepared as in WO 2007/081597) in THF (10 mL) was quickly added and the reaction proceeded for 2 h, keeping the internal temperature below −50° C. Water (100 mL) and EA (200 mL) were added. The two layers were separated and the aq. layer was extracted with EA. The combined org. layers were washed with brine, dried over $Na_2SO_4$, filtered and concentrated to dryness. The residue was purified by CC (Hept-EA 2:1) to afford the title intermediate as a pale yellow oil, which solidified (2.83 g, 75% yield) after standing at rt for one day.

MS (ESI, m/z): 407.3 $[M+H^+]$.

G.ii. (3RS)-[3-(7-fluoro-2-methoxy-quinolin-8-yl)-2-hydroxymethyl-propyl]-carbamic acid tert-butyl ester To a solution of intermediate G.i (0.64 g, 1.58 mmol) in THF (25 mL), cooled to 0° C., was added in one portion $LiAlH_4$ (0.21 g). The mixture was stirred at the same temperature for 15 min and additional $LiAlH_4$ (0.07 g) was added. After 5 min, the reaction mixture was warmed to rt and further stirred 45 min. Water (0.7 mL) was carefully added, followed by 2M NaOH (1.2 mL) and water (1.2 mL). After stirring 5 min, $Na_2SO_4$ (2 g) was added and the mixture was stirred 15 min. The solids were filtered off and thoroughly washed with EA. The filtrate was concentrated to dryness. The residue was purified by CC (Hept-EA 2:1) to afford the title intermediate as a colourless oil (534 mg, 93% yield).

MS (ESI, m/z): 365.1 $[M+H^+]$.

G.iii. (3RS)-methanesulfonic acid 2-(tert-butoxycarbonylamino-methyl)-3-(7-fluoro-2-methoxy-quinolin-8-yl)-propyl ester To a solution of intermediate G.ii (497 mg, 1.36 mmol) in DCM (10 mL) were added, at 0° C., TEA (0.38 mL, 2.73 mmol) and MsCl (0.13 mL, 1.64 mmol). The reaction proceeded 1 h at this temperature. Sat. aq. $Na_2CO_3$ and DCM were added. The two layers were separated and the aq. layer was extracted once more with DCM. The combined org. layers were dried over $Na_2SO_4$, filtered and concentrated to dryness to afford the title intermediate as a colourless oil (620 mg, 100% yield).

MS (ESI, m/z): 443.0 $[M+H^+]$.

G.iv. (RS)-(10-fluoro-5-oxo-2,3-dihydro-1H,5H-pyrido[3,2,1-ij]quinolin-2-ylmethyl)-carbamic acid tert-butyl ester A solution of intermediate G.iii (620 mg, 1.40 mmol) in toluene (20 mL) was refluxed overnight. After cooling to rt, water and EA were added and the layers separated. The aq. layer was extracted once more with EA and the combined org. layers were washed with saturated $NaHCO_3$, concentrated and the residue was purified by CC (Hept/EA 1:1 to EA) to afford the title intermediate as a colourless foam (264 mg, 57% yield).

MS (ESI, m/z): 333.1 $[M+H^+]$.

G.v. (RS)-6-aminomethyl-8-fluoro-6,7-dihydro-5H pyrido[3,2,1-ij]quinolin-3-one Starting from intermediate G.iv and using General Method A, the title intermediate was obtained as a colourless solid (190 mg, 100% yield)

MS (ESI, m/z): 233.3 $[M+H^+]$.

Preparation H: 6-((S)-5-iodomethyl-2-oxo-oxazolidin-3-yl)-4H-benzo[1,4]thiazin-3-one

H.i. 6-[(S)-3-(tert-butyl-dimethyl-silanyloxy)-2-hydroxy-propylamino]-4H-benzo[1,4]thiazin-3-one To a solution of tert-butyl-dimethyl-((S)-1-oxiranyl-methoxy)-silane (commercial; 13.0 g, 69 mmol) in MeCN (220 mL) was added $LiClO_4$ (22 g, 207 mmol). 6-amino-4H-benzo[1,4]thiazin-3-one (commercial; 11.45 g, 64 mmol) was added and the mixture was stirred at 50° C. for 6 h. The solvent was removed in vacuo and the residue was purified by CC (DCM/MeOH/$NH_4OH$ 1000:25:2 to 1000:100:2) to afford the title compound as a pale brown foam (11.16 g, 44% yield).

MS (ESI, m/z): 353.3 $[M+H^+]$.

H.ii. 6-[(S)-5-(tert-butyl-dimethyl-silanyloxymethyl)-2-oxo-oxazolidin-3-yl]-4H-benzo[1,4]thiazin-3-one A solution of intermediate H.i (11.16 g, 30 mmol) and CDI (5.57 g, 33 mmol) in THF (130 mL) was heated at 50° C. for 2 h; the mixture was concentrated in vacuo and partitioned between EA and water. Some crystallized product was filtered and washed with $H_2O$ and EA to give 5.21 g of solid. The org. layer was washed with brine, dried over $MgSO_4$ and concentrated under reduced pressure. The residue was purified by CC (DCM/MeOH 1000:50:4) to give additional 2.28 g of product as a colourless solid (total: 7.49 g, 63% yield).

MS (ESI, m/z): 379.2 $[M+H^+]$.

H.iii. 6-((S)-5-hydroxymethyl-2-oxo-oxazolidin-3-yl)-4H-benzo[1,4]thiazin-3-one A suspension of intermediate H.ii (11.49 g, 29.1 mmol) in THF (30 mL) was treated with TBAF (1M in THF, 29.1 mL) at 0° C. The yellow solution was stirred at 0° C. for 3 h and then partitioned between water and EA. Some crystallized product was filtered and washed with $H_2O$ and EA to give 6.49 g of solid. The aq. phase was extracted with EA (3×). The combined org. layers were washed with brine, dried over $MgSO_4$, filtered and concentrated under reduced pressure. The additional crude product was triturated with EA to give 1.23 g of an off-white solid (overall 7.72 g, 95% yield).

MS (ESI, m/z): 265.5 $[M+H^+]$.

H.iv. Toluene-4-sulfonic acid (S)-2-oxo-3-(3-oxo-3,4-dihydro-2H-benzo[1,4]thiazin-6-yl)-oxazolidin-5-ylmethyl ester To a solution of intermediate H.iii (3.22 g, 11.5 mmol) and DMAP (1.40 g, 11.5 mmol) in DCM (80 mL) cooled to 0° C. were added TEA (4.6 mL, 33.3 mmol) and a solution of TsCl (2.19 g, 11.5 mmol) in DCM (15 mL). The mixture was stirred at rt overnight, after which water was added. The resulting solid was filtered and dried to afford the title compound as a beige solid (4.19 g, 84% yield).

MS (ESI, m/z): 435.2 $[M+H^+]$.

H.v. 6-((S)-5-iodomethyl-2-oxo-oxazolidin-3-yl)-4H-benzo[1,4]thiazin-3 one

A suspension of intermediate H.iv (4.19 g, 9.64 mmol) and NaI (5.78 g, 38.57 mmol) in acetone (70 mL) was refluxed for 5 h. The solvent was evaporated and the residue extracted with water/DCM. Thereby the desired product precipitated as a pale beige solid (3.40 g, 90% yield).

MS (ESI, m/z): 391.1 $[M+H^+]$.

Preparation I: methanesulfonic acid (S)-2-oxo-3-(3-oxo-3,4-dihydro-2H-benzo[1,4]oxazin-6-yl)-oxazolidin-5-ylmethyl ester I.i. 6-[(S)-3-(tert-butyl-dimethyl-silanyloxy)-2-hydroxy-propylamino]-4H-benzo[1,4]oxazin-3-one To a solution of tert-butyl-dimethyl-((S)-1-oxiranylmethoxy)-silane (commercial; 10.0 g, 53 mmol) in MeCN (160 mL) was added LiClO$_4$ (16.9 g, 159 mmol). 6-amino-4H-benzo[1,4]oxazin-3-one (commercial; 8.72 g, 53.1 mmol) was added and the mixture was stirred at 50° C. for 6 h. The solvent was removed in vacuo and the residue was purified by FC (DCM/MeOH/NH$_4$OH 1000:25:2 to 1000:100:2) to afford the title compound as a pale brown foam (10.24 g, 55% yield).
MS (ESI, m/z): 353.3 [M+H$^+$].

I.ii. 6-[(S)-5-(tert-butyl-dimethyl-silanyloxymethyl)-2-oxo-oxazolidin-3-yl]-4H-benzo[1,4]oxazin-3-one A solution of intermediate I.i (10.24 g, 29 mmol) and CDI (9.71 g, 58.1 mmol) in THF (140 mL) was heated at 50° C. for 2 h. The mixture was then concentrated in vacuo and partitioned between EA and water. The org. layer was washed with brine, dried over MgSO$_4$ and concentrated under reduced pressure. The residue was triturated with ether to afford the title intermediate as a yellowish solid (6.30 g, 57% yield).
MS (ESI, m/z): 379.2 [M+H$^+$].

I.iii. 6-((S)-5-hydroxymethyl-2-oxo-oxazolidin-3-yl)-4H-benzo[1,4]oxazin-3-one

A suspension of intermediate I.ii (6.30 g, 16.6 mmol) in THF (20 mL) was treated with TBAF (1M in THF, 16.6 mL) at 0° C. The yellow solution was stirred at 0° C. for 3 h and then partitioned between water and EA. The aq. phase was extracted with EA (3×). The combined org. layers were washed with brine, dried over MgSO$_4$, filtered and concentrated under reduced pressure. The crude product was triturated with EA to give the title intermediate as a colourless solid (3.49 g, 79% yield).
MS (ESI, m/z): 265.5 [M+H$^+$].

I.iv. Methanesulfonic acid (S)-2-oxo-3-(3-oxo-3,4-dihydro-2H-benzo[1,4]oxazin-6-yl)-oxazolidin-5-ylmethyl ester A solution of intermediate I.iii (2.44 g, 9.23 mmol) in DCM (50 mL) was cooled to 0° C. DIPEA (3.58 g, 3 eq.) and MsCl (1.27 g, 1.2 eq.) were added and the mixture stirred at 0° C. for 1 h. The mixture was diluted with DCM and washed with water. The org. phase was dried over MgSO$_4$ and concentrated. The residue was purified by CC (DCM/MeOH 1000:50:4) to afford the title compound as an off-white solid (1.40 g, 44% yield).
$^1$H NMR (DMSO-d6) δ: 10.72 (s, 1H), 7.29 (dd, J=2.1, 0.6 Hz, 1H), 6.94 (m, 2H), 4.95 (m, 1H), 4.52 (s, 2H), 4.49 (m, 2H), 4.11 (t, J=9.1 Hz, 1H), 3.73 (m, 2H), 3.23 (s, 3H).
MS (ESI, m/z): 343.2 [M+H$^+$].

Preparation J: (S)-3-(2,3-dihydro-benzo[1,4]dioxin-6-yl)-5-iodomethyl-oxazolidin-2-one J.i. (S)-3-(2,3-dihydro-benzo[1,4]dioxin-6-yl)-5-hydroxymethyl-oxazolidin-2-one A solution of (2,3-dihydro-benzo[1,4]dioxin-6-yl)-carbamic acid benzyl ester (3.0 g, 10.5 mmol; prepared according to WO 2007/107965) in THF (60 mL) was cooled to −78° C. before the dropwise addition of nBuLi (5.1 mL of a 2.5M solution in Hex, 1.2 eq.). The mixture was stirred at −78° C. for 1 h and then warmed to −15° C. At this temperature (S)-glycidyl butyrate (1.98 g, 1.2 eq.) was added dropwise. The mixture was stirred at rt overnight. Cs$_2$CO$_3$ (tip of a spatula) was added and the mixture heated at 40° C. until complete conversion. The mixture was diluted with EA and washed with sat. NH$_4$Cl solution and water. The org. layer was dried over MgSO$_4$, concentrated and purified by CC (Hex/EA 2:1 to 1:1) giving the desired intermediate as beige solid (1.09 g, 41% yield).
$^1$H NMR (DMSO d6) a: 7.13 (d, J=2.5 Hz, 1H), 6.96 (dd, J=2.5, 8.9 Hz, 1H), 6.86 (d, J=8.9 Hz, 1H), 5.16 (t, J=5.8 Hz, 1H), 4.70-4.50 (m, 1H), 4.30-4.1.0 (m, 4H), 4.10-3.90 (m, 1H), 4.80-4.70 (m, 1H), 4.70-4.60 (m, 1H), 4.60-4.50 (m, 1H).
MS (ESI, m/z): 252.2 [M+H$^+$].

J.ii. Methanesulfonic acid (S)-3-(2,3-dihydro-benzo[1,4]dioxin-6-yl)-2-oxo-oxazolidin-5-ylmethyl ester A solution of intermediate J.i (430 mg, 1.7 mmol) in DCM (10 mL) was cooled to 0° C. DIPEA (0.81 mL, 2.9 eq.) and MsCl (0.16 mL, 1.2 eq.) were added and the mixture was stirred at 0° C. for 1 h. Water was added and the mixture was extracted with DCM. The residue was triturated with ether to afford the title intermediate as a beige solid (0.55 g, 98% yield).
MS (ESI, m/z): 330.0 [M+H$^+$].

J.ii. (S)-3-(2,3-dihydro-benzo[1,4]dioxin-6-yl)-5-iodomethyl-oxazolidin-2-one

A mixture of intermediate J.ii (509 mg, 1.55 mmol) and NaI (927 mg, 6.18 mmol) in acetone (10 mL) was heated at reflux for 3 h. After cooling to rt the solvent was evaporated and the residue extracted with water/DCM. The org. layer was washed with brine, dried over MgSO$_4$ and concentrated. The residue was triturated with ether to afford the title compound as beige solid (0.393 g, 70% yield).
$^1$H NMR (CDCl$_3$) δ: 7.07 (d, J=2.6 Hz, 1H), 6.98 (dd, J=9.1, 2.6 Hz, 1H), 6.85 (d, J=8.9 Hz, 1H), 4.68 (m, 1H), 4.24 (s, 4H), 4.10 (t, J=9.1 Hz, 1H), 3.72 (dd, J=9.1, 5.9 Hz, 1H), 3.46 (m, 1H), 3.33 (m, 1H).
MS (ESI, m/z): 362.1 [M+H$^+$].

Preparation K: (RS)-methanesulfonic acid 2-[2-oxo-3-(3-oxo-3,4-dihydro-2H-benzo[1,4]thiazin-6-yl)-oxazolidin-5-yl]-ethyl ester K.i. (RS)-6-[4-(tert-butyl-dimethyl-silanyloxy)-2-hydroxy-butylamino]-4H-benzo[1,4]thiazin-3-one A solution of (RS)-tert-butyl-dimethyl-(2-oxiranylethoxy)-silane (4 g, 20 mmol; prepared according to *Heterocycles* (1987), 25(1), 329-32) and 6-amino-4H-benzo[1,4]thiazin-3-one (4 g, 20 mmol) in EtOH/water 9:1 (140 mL) was heated at 80° C. for 2 days. The mixture was concentrated under reduced pressure and the residue was purified by CC (DCM/MeOH/NH$_4$OH 1000:50:4) to afford the title intermediate as a brown oil (2.2 g, 29% yield).
MS (ESI, m/z): 383.2 [M+H$^+$].

K.ii. (RS)-6-{5-[2-(tert-butyl-dimethyl-silanyloxy)-ethyl]-2-oxo-oxazolidin-3-yl}-4H-benzo[1,4]thiazin-3-one Starting from intermediate K.i and using General Method D, the title intermediate was obtained after CC (DCM/MeOH/NH$_4$OH 1000:50:4) as an orange solid (1.53 g, 65% yield).
MS (ESI, m/z): 409.4 [M+H$^+$].

K.iii. (RS)-6-[5-(2-hydroxy-ethyl)-2-oxa-oxazolidin-3-yl]-4H-benzo[1,4]thiazin-3-one A solution of intermediate K.ii (1.50 g, 3.67 mmol) in THF (10 mL) was treated with a TBAF solution (1M in THF, 1 eq.). The solution was stirred at 0° C. for 2 h, after which water and EA were added. The aq. phase was extracted with EA. The combined org. layers were washed with brine, dried over $MgSO_4$, filtered and concentrated under reduced pressure. The residue was recrystallized from ether/EA to afford the title intermediate as a beige solid (730 mg, 68% yield).
MS (ESI, m/z): 295.1 [M+H$^+$].

K.iv. (RS)-methanesulfonic acid 2-[2-oxo-3-(3-oxo-3,4-dihydro-2H benzo[1,4]thiazin-6-yl)-oxazolidin-5-yl]-ethyl ester A solution of intermediate K.iii (700 mg, 2.34 mmol) in anhydrous DCM (12 mL) and DIPEA (1.1 mL, 6.8 mmol) was cooled to 0° C. and MsCl (0.23 mL, 2.9 mmol) was added dropwise. The resulting mixture was stirred at 0° C. for 1 h. Water was added and the mixture was extracted with DCM and the combined org. layers were washed with water. The yellow residue was purified by CC (DCM/MeOH/NH$_4$OH 1000:50:4) to afford the title intermediate as a beige solid (795 mg, 90% yield).
MS (ESI, m/z): 373.1 [M+H$^+$].

Preparation L: rac-5-aminomethyl-3-fluoro-5,6-dihydro-4H-1,6a-diaza-phenalen-7-one

L.i. rac-2-(tert-butoxycarbonylamino-methyl)-3-(3-fluoro-6-methoxy-[1,5]naphthyridin-4-yl)-propionic acid ethyl ester To a solution of LiHMDS (1M, 17 mL, 2.2 eq.), cooled to −78° C., was added dropwise a solution of 3-tert-butoxycarbonylamino-propionic acid ethyl ester (1.70 g, 7.82 mmol, prepared according to *Tetrahedron Lett.* (2003), 44, 2807-2811) in THF (20 mL). The solution was stirred at the same temperature for 90 min. A solution of 8-bromomethyl-7-fluoro-2-methoxy-[1,5]naphthyridine (2.12 g, 1 eq., prepared according to WO 2008/078305) in THF (10 mL) was quickly added and the reaction proceeded 2 h, keeping the internal temperature below −50° C. Water (100 mL) and EA (200 mL) were added. The two layers were decanted and the aq. layer was extracted with EA. The combined org. layers were washed with brine, dried over Na$_2$SO$_4$, filtered and concentrated to dryness. The residue was chromatographed (Hept-EA 2-1) to afford the title intermediate as a yellow oil (2.38 g, 75% yield).
MS (ESI, m/z): 408.6 [M+H$^+$].

L.ii. rac-[3-(3-fluoro-6-methoxy-[1,5]naphthyridin-4-yl)-2-hydroxymethyl-propyl]-carbamic acid tert-butyl ester To a solution of intermediate L.i (2.38 g, 5.84 mmol) in THF (80 mL), cooled to −5° C., was added in one portion LiAlH$_4$ (776 mg, 3.5 eq.). The mixture was stirred at the same temperature for 15 min. Water (2.7 mL) was carefully added, followed by 2M NaOH (4.7 mL) and water (4.7 mL). After stirring for 5 min at rt, Na$_2$SO$_4$ (7 g) was added and the mixture was stirred for 15 min. The solids were filtered off and thoroughly washed with EA. The filtrate was concentrated to dryness. The residue was purified by CC (Hept-EA 1-1) to afford the title intermediate as a pale yellow oil (1.59 g, 74% yield).
MS (ESI, m/z): 366.2 [M+H$^+$].

L.iii. rac-methanesulfonic acid 2-(tert-butoxycarbonylamino-methyl)-3-(3-fluoro-6-methoxy-[1,5]naphthyridin-4-yl)-propyl ester To a solution of intermediate L.ii (657 mg, 1.80 mmol) in DCM (15 mL) were added at 0° C., TEA (0.50 mL, 2 eq.) and MsCl (0.17 mL, 1.2 eq.). The reaction proceeded 1 h at this temperature. Sat. aq. NaHCO$_3$ and DCM were added. The two layers were decanted and the aq. layer was extracted once more with DCM (50 mL). The combined org. layers were dried over Na$_2$SO$_4$, filtered and concentrated to dryness. The residue was carried on without further purification to afford the title intermediate as an orange oil (0.794 g, quant.).
MS (ESI, m/z): 444.0 [M+H$^+$].

L.iv. rac-(3-fluoro-7-oxo-5,6-dihydro-4H,7H-1,60-diaza-phenalen-5-ylmethyl)-carbamic acid tert-butyl ester A solution of intermediate L.iii (0.794 g, 1.79 mmol) in toluene (20 mL) was heated overnight at 85° C. and then at 110° C. for 5 h. After cooling to rt, water and EA were added and the layers separated. The aq. layer was extracted once more with EA and the combined org. layers were washed with NaHCO$_3$ and concentrated under reduced pressure. The residue was purified by CC (Hept/EA 1:1 to EA) to afford the title intermediate as a pale yellow oil (0.226 g, 38% yield).
MS (ESI, m/z): 333.9 [M+H$^+$].

L.v. rac-5-aminomethyl-3-fluoro-5,6-dihydro-4H-1,6a-diaza-phenalen-7-one

Starting from intermediate L.iv and using General Method A, the title compound was obtained as a pale yellow solid (146 mg, 81% yield).
MS (ESI, m/z): 234.1 [M+H$^+$].

Preparation M: rac-5-aminomethyl-4,5-dihydro-pyrrolo[3,2,1-de][1,5]naphthyridin-7-one

M.i. 8-allyl-2-methoxy-[1,5]naphthyridine

A flask charged with trifluoro-methanesulfonic acid 6-methoxy-[1,5]naphthyridin-4-yl ester (2.50 g, 8.11 mmol; prepared according to WO 2007/107965), allyltributyltin (3.11 mL, 1.25 eq.) and DMF (20 mL) was degassed with 1\12. LiCl (1.29 g, 3.75 eq.) and Pd(PPh$_3$)$_4$ (234 mg, 0.025 eq.) were added and the mixture was stirred at 100° C. for 2 h. After cooling to rt the mixture was poured into 10% aq. NH$_4$OH and EA, the aq layer was extracted with EA and the combined org. layers were washed with water (2×) and brine, dried over MgSO$_4$ and concentrated. The residue was purified by CC (Hept/EA 2:1) to afford the title intermediate as a yellow oil (1.59 g, 98% yield).
MS (ESI, m/z): 201.5 [M+H$^+$].

M.ii. rac-3-(6-methoxy-[1,5]naphthyridin-4-yl)-propane-1,2-diol

To a solution of intermediate M.i (1.59 g, 7.94 mmol) in DCM (28 mL) was added water (4 mL), NMO (1.18 g, 1.1 eq.) and the K$_2$OsO$_4$ dihydrate (29 mg, 0.01 eq.). The resulting mixture was vigorously stirred at rt overnight. The phases were separated, the aq. layer was extracted several times with DCM and the combined org. layers was washed with 10% aq. Na$_2$S$_2$O$_3$. The residue was triturated with TBME to afford the title intermediate as a beige solid (1.28 g, 69% yield).
MS (ESI, m/z): 235.2 [M+H$^+$].

M.iii. rac-1-(tert-butyl-dimethyl-silanyloxy)-3-(6-methoxy-[1,5]naphthyridin-4-yl)-propan-2-ol To a solution of intermediate M.ii (1.275 g, 5.44 mmol) in THF (60 mL) were added imidazole (0.347 g, 1 eq.) and TBSCl (0.864 g, 1 eq.). The mixture was stirred at rt for 3 h. Water was added and the mixture extracted with DCM. The org. layer was dried over MgSO$_4$ and concentrated under reduced pressure to afford the title intermediate as a light brown solid (2 g, quant.).
MS (ESI, m/z): 349.2 [M+H$^+$].

M.iv. rac-methanesulfonic acid 1-(tert-butyl-dimethyl-silanyloxymethyl)-2-(6-methoxy-[1,5]naphthyridin-4-yl)-ethyl ester To a solution of intermediate M.iii (1.79 g, 5.13 mmol) in DCM (20 mL) were added at 0° C., TEA (1.43 mL, 2 eq.) and MsCl (0.48 mL, 1.2 eq.). The reaction proceeded 40 min at this temperature. Water was added and the two layers were decanted and the aq. layer was extracted once more with DCM. The combined org. layers were concentrated to dryness to afford the title intermediate as a yellow oil (2.11 g, 96% yield).
MS (ESI, m/z): 427.1 [M+H$^+$].

M.v. rac-5-hydroxymethyl-4,5-dihydro-pyrrolo[3,2,1-de][1,5]naphthyridin-7-one A solution of intermediate M.iv (2.12 g, 5.0 mmol) in DCE (3 mL) and toluene (6 mL) was stirred at 110° C. for 2 h. The dark brown mixture was concentrated and purified by CC (EA/MeOH 9:1, EA/MeOH/NH$_4$OH 9:1:0.1; DCM/MeOH/NH$_4$OH 1000:100:8) to afford the title intermediate as a brown oil (0.215 g, 21% yield).
MS (ESI, m/z): 203.0 [M+H$^+$].

M.vi. rac-methanesulfonic acid 7-oxo-4,5-dihydro-7H-pyrrolo[3,2,1-de][1,5]naphthyridin-5-ylmethyl ester To a solution of intermediate M.v (0.25 g, 1.24 mmol) in DCM (7 mL) were added at 0° C., TEA (0.344 mL, 2 eq.) and MsCl (0.115 mL, 1.2 eq). The reaction proceeded 1 h at this temperature. Water was added. The two layers were decanted and the aq. layer was extracted once more with DCM. The combined org. layers were concentrated to dryness to afford the title intermediate as a brown solid (0.26 g, 75% yield).
MS (ESI, m/z): 281.4 [M+H$^+$].

M.vii. rac-5-azidomethyl-4,5-dihydro-pyrrolo[3,2,1-de][1,5]naphthyridin-7-one A solution of intermediate M.vi (0.26 g, 0.93 mmol) in DMF (9 mL) was treated with sodium azide (482 mg, 8 eq.) and stirred at 50° C. for 20 h. After cooling to rt, water was added and the mixture extracted with EA. The org. layer was washed with water and brine, dried over MgSO$_4$ and concentrated to afford the title intermediate as a brown oil (0.15 g, 71% yield).
MS (ESI, m/z): 228.3 [M+H$^+$].

M.viii. rac-5-aminomethyl-4,5-dihydro-pyrrolo[3,2,1-de][1,5]naphthyridin-7-one To a solution of intermediate M.vii (145 mg, 0.64 mmol) in THF (1.5 mL) was added PPh$_3$ (335 mg, 2 eq.), water (0.115 mL, 10 eq.), AcOH (1 eq.), and 1N HCl (1 eq.). The mixture was heated at 70° C. for 2 days. The reaction mixture was concentrated and the residue was taken up in DCM and extracted with aq. 10% citric acid (2×). The comb. aq. layers were basified with NH$_4$OH and then extracted with DCM (to remove PPh$_3$O) and then with DCM/MeOH 9:1 (to get the product). The combined DCM/MeOH 9:1 layers were concentrated under reduced pressure to afford the title intermediate as a yellow foam (50 mg, 39% yield).
MS (ESI, m/z): 202.2 [M+H$^+$].

Preparation N: (2S)-2-aminomethyl-9-fluoro-1,2-dihydro-pyrrolo[3,2,1-ij]quinolin-4-one The title (S)-amine was prepared as described in Preparation A, with the only exception that during the step A.iv, (DHQ)$_2$PHAL was employed as a chiral ligand (instead of (DHQD)$_2$PHAL).
$^1$H NMR (CDCl$_3$) δ: 7.65 (d, J=9.4 Hz, 1H); 7.36 (ddt, J=13.0, 4.4, 8.5 Hz, 1H); 6.87 (t, J=9.1 Hz, 1H); 6.58 (d, J=9.4 Hz, 1H); 5.02 (m, 1H); 3.53 (ddq, J=1.4, 9.0, 17.0 Hz, 1H); 3.36 (dd, J=4.6, 11.1 Hz, 1H); 3.33 (overlapped m, 1H); 3.24 (dd, J=3.0, 11.1 Hz, 1H); 1.31 (br. s, 2H).

Preparation O: rac-5-aminomethyl-3-fluoro-4,5-dihydropyrrolo[3,2,1-de][1,5]naphthyridin-7-one

O.i. rac-1-(tert-butyl-dimethyl-silanyloxy)-3-(3-fluoro-6-methoxy-[1,5]naphthyridin-4-yl)-propan-2-ol A solution of rac-3-(3-fluoro-6-methoxy-[1,5]naphthyridin-4-yl)-propane-1,2-diol (3.6 g, 14.2 mmol, prepared as described in WO 2008/003690) in THF (150 mL) and DMF (10 mL) was treated with imidazole (1.07 g, 1.1 eq.) and a solution of TBDMSCl (2.15 g, 1 eq.) in THF (10 mL) at 0° C., the mixture was stirred at rt for 24 h, diluted with EA and washed with water (2×100 mL) and brine, dried over MgSO$_4$ and concentrated. The residue was purified by CC (Hept/EA 1:1) to give the desired intermediate as a colourless solid (4.5 g, 87% yield).
$^1$H NMR (CDCl$_3$) δ: 8.65 (d, J=0.6 Hz, 1H), 8.20 (d, J=9.1 Hz, 1H), 7.09 (d, J=8.8 Hz, 1H), 4.08 (s, 3H), 3.79 (d, J=4.7 Hz, 1H), 3.66 (t, J=5.0 Hz, 2H), 3.42 (dd, J=6.2, 1.8 Hz, 2H), 0.91 (m, 9H), 0.07 (d, J=2.3 Hz, 6H).

O.ii. rac-5-(tert-butyl-dimethyl-silanyloxymethyl)-3-fluoro-4,5-dihydropyrrolo[3,2,1-de][1,5]naphthyridin-7-one A solution of intermediate O.i (4.5 g, 12.4 mmol) in DCM (75 mL) at 0° C. was treated with TEA (2.07 mL, 1.2 eq.) and MsCl (1.06 mL, 1.1 eq.). The mixture was stirred at 0° C. for 1 h and at rt for 1 h, diluted with DCM and washed with water. The org. phase was dried over MgSO$_4$ and concentrated, dissolved in DCE (100 mL) and heated at reflux overnight. The volatiles were removed under reduced pressure and the residue purified by CC (Hept/EA 1:1, EA) to give the desired compound as a colourless solid (1.76 g, 42% yield). $^1$H NMR (CDCl$_3$) δ: 8.30 (d, J=1.5 Hz, 1H), 7.87 (d, J=9.7 Hz, 1H), 6.78 (dd, J=9.7, 0.6 Hz, 1H), 5.11 (m, 1H), 4.40 (dd, J=10.5, 3.2 Hz, 1H), 3.86 (dd, J=10.5, 2.1 Hz, 1H), 3.51 (dd, J=6.4, 1.8 Hz, 2H), 0.60 (m, 9H), −0.03 (s, 3H), −0.19 (s, 3H).

O.iii. rac-3-fluoro-5-hydroxymethyl-4,5-dihydropyrrolo[3,2,1-de][1,5]naphthyridin-7-one A solution of intermediate O.ii (1.76 g, 5.3 mmol) in THF (10 mL) was treated with TBAF (1M in THF, 6.3 mL, 1.2 eq.). The mixture was stirred at rt for 2 h and partitioned between EA and water. The org. phase was washed with water and brine, dried over MgSO$_4$ and concentrated in vacuo. The residue was purified by CC (EA, EA/MeOH 9:1), triturated with ether and filtered to give the title alcohol as a colourless solid (892 mg, 77% yield).

¹H NMR (DMSO-d6) δ: 8.41 (d, J=1.5 Hz, 1H), 7.94 (d, J=9.7 Hz, 1H), 6.72 (d, J=9.7 Hz, 1H), 4.99 (m, 2H), 4.09 (ddd, J=11.7, 6.2, 3.8 Hz, 1H), 3.62 (m, 2H), 3.37 (m, 1H).

O.iv. rac-methanesulfonic acid 3-fluoro-7-oxo-4,5-dihydro-7H-pyrrolo[3,2,1-de][1,5]naphthyridin-5-ylmethyl ester A suspension of intermediate O.iii (660 mg, 3 mmol) in DCM (20 mL) was treated with TEA (0.83 mL, 2 eq.) and cooled to 2° C. MsCl (0.28 mL, 1.2 eq.) was added dropwise. The mixture was stirred at rt for 45 min, partitioned between water and DCM. The org. phase was dried over MgSO₄ and concentrated to give the desired mesylate as a beige solid (1 g, quant.).
MS (ESI, m/z): 299.2 [M+H⁺].

O.v. rac-5-azidomethyl-3-fluoro-4,5-dihydro-pyrrolo[3,2,1-de][1,5]naphthyridin-7-one A solution of intermediate O.iv (865 mg, 2.9 mmol) in DMF (6 mL) was treated with NaN₃ (226 mg, 1.2 eq.). The mixture was heated at 80° C. overnight, cooled and partitioned between EA and water. The org. phase was washed with water and brine, dried over MgSO₄ and concentrated. The residue was purified by CC (EA) to give the title azide as a brown oil (660 mg, 84% yield).
MS (ESI, m/z): 246.0 [M+H⁺].

O.vi. rac-5-aminomethyl-3-fluoro-4,5-dihydro-pyrrolo[3,2,1-de][1,5]naphthyridin-7-one To a solution of intermediate O.v (60 mg, 2.44 mmol) in THF (14 mL) was added PPh₃ (706 mg, 1.1 eq.) and water (0.44 mL, 10 eq.). The mixture was heated at 50° C. for 5 h. The reaction mixture was partitioned between ether and water. The aq. phase was concentrated in vacuo, triturated with DCM/MeOH 9:1, decanted from insoluble material and concentrated in vacuo to give the title amine as a beige solid (0.42 g, 78% yield).
MS (ESI, m/z): 220.1 [M+H⁺].

Preparation P: 6-[(R)-5-(2-iodo-ethyl)-2-oxo-oxazolidin-3-yl]-4H-benzo[1,4]thiazin-3-one P.i. tert-butyl-dimethyl-[(R)-2-oxiranyl-ethoxy]-silane and (2,5)-4-(tert-butyl-dimethyl-silanyloxy)-butane-1,2-diol The title intermediates were prepared in analogy to Kishi et al, *Org. Lett.* (2005), 7, 3997, (intermediate S2-3) via hydrolytic kinetic resolution of (RS)-tert-butyl-dimethyl-(2-oxiranyl-ethoxy)-silane (prepared according to *J. Org. Chem.* (2008), 73, 1093). Two compounds were isolated after CC (Hept/EA 2:1).
First eluting compound: tent-butyl-dimethyl-[(R)-2-oxiranyl-ethoxy]-silane (colourless oil, 25.3 g, 48% yield). ¹H NMR (CDCl₃) δ: 3.77 (t, J=6.4 Hz, 2H), 3.04 (m, 1H), 2.78 (m, 1H), 2.51 (dd, J=5.0, 2.9 Hz, 1H), 1.74 (m, 2H), 0.90 (d, J=0.6 Hz, 9H), 0.06 (s, 6H).
Second eluting compound: (2S)-4-(tert-butyl-dimethyl-silanyloxy)-butane-1,2-diol (colourless oil, 24.9 g, 43% yield). ¹H NMR (CDCl₃) δ: 3.89 (m, 3H), 3.62 (s, 3.53 (m, 1H), 3.42 (br. s, 1H), 2.29 (m, 1H), 1.70 (m, 2H), 0.90 (s, 9H), 0.09 (s, 61-1).

P.ii. 6-[(R)-4-(tert-butyl-dimethyl-silanyloxy)-2-hydroxy-butylamino]-4H-benzo[1,4]thiazin-3-one A solution of 6-amino-4H-benzo[1,4]thiazin-3-one (10.68 g, 59.3 mmol; commercial) and tert-butyl-dimethyl-[(R)2-oxiranyl-ethoxy]-silane (first eluting compound of step P.i, 12.0 g, 59.3 mmol) in 9-1 EtOH/H₂O (320 mL) was heated at 80° C. for 2 days. The mixture was concentrated under reduced pressure. Residual starting aniline could be removed by addition of Et₂O/MeOH followed by filtration. The filtrate containing the product was concentrated under reduced pressure to afford the title intermediate as a brown oil (18.8 g, 83% yield) which was used as such in the next step.
MS (ESI, m/z): 383.2 [M+H⁺].

P.iii. 6-{(R)-5-[2-(tert-butyl-dimethyl-silanyloxy)-ethyl]-2-oxo-oxazolidin-3-yl}-4H-benzo[1,4]thiazin-3-one A solution of intermediate P.ii (23.5 g, 49.1 mmol) and CDI (9.57 g, 1.2 eq.) in THF (250 mL) was heated at 50° C. overnight. The mixture was concentrated under reduced pressure and partitioned between EA and water. The aq. layer was extracted once more with EA and the combined org. layers were dried over MgSO₄ and concentrated. The residue was purified by CC (DCM/MeOH/NH₄OH 1000:50:4) to afford the title intermediate as a colourless solid (8.4 g, 42% yield).
MS (ESI, m/z): 409.3 [M+H⁺].

P.iv. 6-[(R)-5-(2-hydroxy-ethyl)-2-oxo-oxazolidin-3-yl]-4H-benzo[1,4]thiazin-3-one A solution of intermediate P.iii (8.4 g, 20.6 mmol) in THF (50 mL) was treated with TBAF (1M solution in THF, 24.7 mL, 1.2 eq.) at 0° C. The solution was stirred at 0° C. for 6 h. The mixture was partitioned between water and EA and the aq. phase was extracted with EA (3×). The combined org. layers were washed with water and brine, dried over MgSO₄ and concentrated. The residue was triturated with Et₂O/EA to afford the title intermediate as an off-white solid (4.79 g, 79% yield).
MS (ESI, m/z): 295.5 [M+H⁺].

P.v. Methanesulfonic acid 2-[(R)-2-oxo-3-(3-oxo-3,4-dihydro-2H-benzo[1,4]thiazin-6-yl)-oxazolidin-5-yl]-ethyl ester A solution of intermediate P.iv (4.7 g, 16.0 mmol) and DIPEA (7.54 mL, 2.9 eq.) in anhydrous DCM (80 mL) was cooled to 0° C. and treated dropwise with MSCl (1.50 mL, 1.2 eq.). The resulting mixture was stirred at 0° C. for 1 h. Water and DCM were added and the phases separated. The org. layer was dried over MgSO₄ and concentrated under reduced pressure. The residue was purified by CC (DCM/MeOH/NH₄OH 1000:50:4) to afford the title intermediate as an off-white solid (5.80 g, 98% yield).
MS (ESI, m/z): 373.4 [M+H⁺].

P.vi. 6-[(R)-5-(2-iodo-ethyl)-2-oxo-oxazolidin-3-yl]-4H-benzo[1,4]thiazin-3-one

A suspension of intermediate P.v (3.5 g, 9.4 mmol) and NaI (4.23 g, 3 eq.) in 2-butanone (35 mL) was heated at 85° C. overnight. After cooling, the mixture was diluted with ether/EA (20 mL) and treated with 10% Na₂S₂O₃ (60 mL). After stirring for 10 min, the phases were separated and the aq. layer was washed with EA. The combined org. layers were washed with water (2×), dried over MgSO₄ and concentrated under reduced pressure. The residue was triturated with Et₂O/EA to afford the title compound as an off-white solid (3.52 g, 93% yield).
MS (ESI, m/z): 405.0 [M+H⁺].

Preparation Q: 6-[(S)-5-(2-Iodo-ethyl)-2-oxo-oxazolidin-3-yl]-4H-benzo[1,4]thiazin-3-one

Q.i. Toluene-4-sulfonic acid (S)-4-(test-butyl-dimethyl-silanyloxy)-2-hydroxy-butyl ester To a solution of (2S)-4-(tert-butyl-dimethyl-silanyloxy)-butane-1,2-diol (23.9 g, 108 mmol; second eluting compound of Preparation P, step P.i) and DMAP (2.65 g, 0.2 eq.) in DCM (80 mL) cooled to 0° C. were added TEA (43.8 mL, 2.9 eq.) and a solution of TsCl (20.7 g, 1.1 eq.) in DCM (15 mL). The mixture was stirred at rt for 5 h, poured on NaHCO$_3$ and extracted with DCM. The org. layer was dried over MgSO$_4$ and concentrated. The residue was purified by CC (Hept/EA 2:1) to afford the title intermediate as a colourless oil (31.3 g, 77% yield).

$^1$H NMR (CDCl$_3$) δ: 7.80 (d, J=7.6 Hz, 2H), 7.34 (d, J=7.6 Hz, 2H), 4.02 (m, 3H), 3.80 (m, 2H), 2.45 (s, 3H), 1.70 (m, 2H), 1.27 (m, 1H), 0.87 (s, 9H), 0.05 (s, 6H).

Q.ii. (2S)-tert-butyl-dimethyl-(2-oxiranyl-ethoxy)-silane

To a solution of intermediate Q.i (31.1 g, 83.1 mmol) in THF (350 mL) was added 2M NaOH (35 mL) and the mixture was vigorously stirred at rt for 3 h. The mixture was taken in 1M NaOH (200 mL) and extracted with TBME (2×). The combined org. layers were washed with water and brine, dried over MgSO$_4$ and concentrated. The resulting oil was purified by Kugelrohr-distillation to afford the title intermediate as a colourless oil (14.7 g, 87% yield).

$^1$H NMR (CDCl$_3$) δ: 3.77 (t, J=6.4 Hz, 2H), 3.04 (m, 1H), 2.78 (m, 1H), 2.51 (dd, J=5.0, 2.9 Hz, 1H), 1.74 (m, 2H), 0.90 (d, J=0.6 Hz, 9H), 0.06 (s, 6H).

Q.iii. 6-[(S)-4-(tert-butyl-dimethyl-silanyloxy)-2-hydroxy-butylamino]-4H-benzo[1,4]thiazin-3-one A solution of 6-amino-4H-benzo[1,4]thiazin-3-one (8.0 g, 44.5 mmol; commercial) and intermediate Q.ii (9.0 g, 1 eq.) in 9-1 EtOH/H$_2$O (250 mL) was heated at 80° C. for 2 days. The mixture was concentrated under reduced pressure. Residual starting aniline could be removed by addition of Et$_2$O/MeOH followed by filtration. The filtrate containing the product was concentrated under reduced pressure to afford the title intermediate as a brown oil (14.58 g, 86% yield) which was used as such in the next step.

MS (ESI, m/z): 383.2 [M+H$^+$].

Q.iv. 6-{(S)-5-[2-(tert-butyl-dimethyl-silanyloxy)-ethyl]-2-oxo-oxazolidin-3-yl}-4H-benzo[1,4]thiazin-3-one A solution of intermediate Q.iii (14.5 g, 37.9 mmol) and CDT (8.60 g, 1.4 eq.) in THF (180 mL) was heated at 50° C. overnight. The mixture was concentrated under reduced pressure and partitioned between EA and water. The aq. layer was extracted once more with EA and the combined org. layers were dried over MgSO$_4$ and concentrated. The residue was purified by CC (DCM/MeOH/NH$_4$OH 1000:50:4) to afford the title intermediate as a colourless solid (5.56 g, 36% yield).

MS (ESI, m/z): 409.3 [M+H$^+$].

Q.v. 6-[(S)-5-(2-hydroxy-ethyl)-2-oxo-oxazolidin-3-yl]-4H-benzo[1,4]thiazin-3-one A solution of intermediate Q.iv (5.50 g, 13.6 mmol) in THF (30 mL) was treated with TBAF (1M solution in THF, 16.3 mL, 1.2 eq.) at 0° C. The solution was stirred at 0° C. for 6 h. The mixture was partitioned between water and EA and the aq. phase was extracted with EA (3×). The combined org. layers were washed with water (3×) and brine, dried over MgSO$_4$ and concentrated. The residue was triturated with Et$_2$O/EA to afford the title intermediate as an off-white solid (3.08 g, 77% yield).

MS (ESI, m/z): 295.5 [M+H$^+$].

Q.vi. Methanesulfonic acid 2-[(S)-2-oxo-3-(3-oxo-3,4-dihydro-2H-benzo[1,4]thiazin-6-yl)-oxazolidin-5-yl]-ethyl ester A solution of intermediate Q.v (3.0 g, 10.2 mmol) and DIPEA (4.8 mL, 2.9 eq.) in anhydrous DCM (50 mL) was cooled to 0° C. and treated dropwise with MsCl (0.96 mL, 1.2 eq.). The resulting mixture was stirred at 0° C. for 1 h. Water and DCM were added and the phases separated. The org. layer was dried over MgSO$_4$ and concentrated under reduced pressure. The residue was triturated with ether to afford the title intermediate as an off-white solid (3.64 g, 96% yield).

MS (ESI, m/z): 373.4 [M+H$^+$].

Q.vii. 6-[(S)-5-(2-iodo-ethyl)-2-oxo-oxazolidin-3-yl]-4H-benzo[1,4]thiazin-3-one A suspension of intermediate Q.vi (2.5 g, 6.7 mmol) and NaI (3.02 g, 3 eq.) in 2-butanone (25 mL) was heated at 85° C. overnight. After cooling, the mixture was diluted with ether/EA (20 mL) and treated with 10% Na$_2$S$_2$O$_3$ (60 mL). After stirring for 10 min, the phases were separated and the aq. layer was washed with EA. The combined org. layers were washed with water (2×), dried over MgSO$_4$ and concentrated under reduced pressure. The residue was triturated with Et$_2$O/EA to afford the title compound as a slightly orange solid (2.11 g, 78% yield).

MS (ESI, m/z): 405.1 [M+H$^+$].

Preparation R: methanesulfonic acid 2-[(R)-2-oxo-3-(3-oxo-3,4-dihydro-2H-benzo[1,4]oxazin-6-yl)-oxazolidin-5-yl]-ethyl ester

R.i. 6-[(R)-4-(tert-butyl-dimethyl-silanyloxy)-2-hydroxy-butylamino]-4H-benzo[1,4]oxazin-3-one A solution of 6-amino-4H-benzo[1,4]oxazin-3-one (commercial; 6.49 g, 39.5 mmol) and tert-butyl-dimethyl-[(R)-2-oxiranyl-ethoxy]-silane (first eluting compound of step P.i of Preparation P; 8.0 g, 39.5 mmol) in EtOH/H$_2$O 9-1 (240 mL) was heated at 80° C. for 2 days. The mixture was concentrated under reduced pressure. Residual starting aniline could be removed by addition of Et$_2$O/MeOH followed by filtration. The filtrate containing the product was concentrated under reduced pressure and the residue was purified by CC (DCM/MeOH/NH$_4$OH 1000:50:4) to afford the title intermediate as a brown oil (5.82 g, 40% yield).

MS (ESI, m/z): 367.3 [M+H$^+$].

R.ii. 6-{(R)-5-[2-(tert-butyl-dimethyl-silanyloxy)-ethyl]-2-oxo-oxazolidin-3-yl}-4H-benzo[1,4]oxazin-3-one A solution of intermediate R.i (5.8 g, 15.8 mmol) and CDT (3.07 g, 1.2 eq.) in THF (50 mL) was heated at 50° C. overnight. The mixture was concentrated under reduced pressure and partitioned between EA and water. The aq. layer was extracted once more with EA and the combined org. layers were dried over MgSO$_4$ and concentrated. The residue was triturated with Et$_2$O/EA/MeOH to afford the title intermediate as a beige solid (2.7 g, 43% yield).

MS (ESI, m/z): 393.5 [M+H$^+$].

R.iii. 6-[(R)-5-(2-hydroxy-ethyl)-2-oxo-oxazolidin-3-yl]-4H-benzo[1,4]oxazin-3-one A solution of intermediate R.ii (2.70 g, 6.88 mmol) in THF (15 mL) was treated with TBAF (1M solution in THF, 8.3 mL, 1.2 eq.) at 0° C. The solution was stirred at 0° C. for 2 h. The mixture was partitioned between water and EA and the aq. phase was extracted with EA (3×). The combined org. layers were washed with water and brine, dried over MgSO$_4$ and concentrated. The residue was triturated with Et$_2$O/MeOH to afford the title compound as an off-white solid (1.25 g, 65% yield).

MS (EST, m/z): 279.5 [M+H$^+$].

R.iv. Methanesulfonic acid 2-[(R)-2-oxo-3-(3-oxo-3, 4-dihydro-2H-benzo[1,4]oxazin-6-yl)-oxazolidin-5-yl]-ethyl ester A solution of intermediate R.iii (2.1 g, 7.55 mmol) and DIPEA (3.57 mL, 2.9 eq.) in anhydrous DCM (40 mL) was cooled to 0° C. and treated dropwise with MsCl (0.71 mL, 1.2 eq.). The resulting mixture was stirred at 0° C. for 1 h. Water and DCM were added and the phases separated. The org. layer was dried over MgSO$_4$ and concentrated under reduced pressure. The residue was triturated with MeOH to afford the title intermediate as an off-white solid (1.16 g, 43% yield).

MS (ESI, m/z): 357.2 [M+H$^+$].

Preparation S: methanesulfonic acid 2-[(S)-2-oxo-3-(3-oxo-3,4-dihydro-2H-benzo[1,4]oxazin-6-yl)-oxazolidin-5-yl]-ethyl ester S.i. 6-[(S)-4-(tert-butyl-dimethyl-silanyloxy)-2-hydroxy-butylamino]-4H-benzo[1,4]oxazin-3-one A solution of 6-amino-4H-benzo[1,4]oxazin-3-one (5.03 g, 30.6 mmol; commercial) and intermediate Q.ii (6.2 g, 1 eq.) in EtOH/H$_2$O 9-1 (180 mL) was heated at 80° C. for 2 days. The mixture was concentrated under reduced pressure. Residual starting aniline could be removed by addition of Et$_2$O/MeOH followed by filtration. The filtrate containing the product was concentrated under reduced pressure to afford the title intermediate as a brown oil (9.45 g, 84% yield) which was used as such in the next step.

MS (ESI, m/z): 367.2 [M+H$^+$].

S.ii. 6-{(S)-5-[2-(tert-butyl-dimethyl-silanyloxy)-ethyl]-2-oxo-oxazolidin-3-yl}-4H-benzo[1,4]oxazin-3-one A solution of intermediate S.i (9.4 g, 25.6 mmol) and CDI (4.99 g, 1.2 eq.) in THF (100 mL) was heated at 50° C. overnight. The mixture was concentrated under reduced pressure and partitioned between EA and water. The aq. layer was extracted once more with EA and the combined org. layers were washed with 0.5M HCl (2×) and water, dried over MgSO$_4$ and concentrated. The residue was triturated, the solids filtered off (mainly starting material and impurities) and the filtrate was concentrated. The resulting solid was triturated once more, the solids filtered off (mainly starting material and impurities) and the filtrate was concentrated. The residue was purified by CC (DCM/MeOH/NH$_4$OH 1000:50:4) to afford the title intermediate as a beige solid (2.40 g, 24% yield).

MS (ESI, m/z): 393.4 [M+H$^+$].

S.iii. 6-[(S)-5-(2-hydroxy-ethyl)-2-oxo-oxazolidin-3-yl]-4H-benzo[1,4]oxazin-3-one A solution of intermediate S.ii (2.40 g, 6.11 mmol) in THF (12 mL) was treated with TBAF (1M solution in THF, 7.33 mL, 1.2 eq.) at 0° C. The solution was stirred at 0° C. for 6 h. The mixture was partitioned between water and EA and the aq. phase was extracted with EA (3×). The combined org. layers were washed with water (3×) and brine, dried over MgSO$_4$ and concentrated. The residue was triturated with Et$_2$O/EA to afford the title intermediate as an off-white solid (0.82 g, 48% yield).

MS (ESI, m/z): 279.5 [M+H$^+$].

S.iv. Methanesulfonic acid 2-[(S)-2-oxo-3-(3-oxo-3, 4-dihydro-2H-benzo[1,4]oxazin-6-yl)-oxazolidin-5-yl]-ethyl ester A solution of intermediate S.iii (0.82 g, 2.95 mmol) and DIPEA (1.4 mL, 2.9 eq.) in anhydrous DCM (15 mL) was cooled to 0° C. and treated dropwise with MsCl (0.28 mL, 1.2 eq.). The resulting mixture was stirred at 0° C. for 1 h. Water and DCM were added and the phases separated. The org. layer was dried over MgSO$_4$ and concentrated under reduced pressure. The residue was triturated with MeOH to afford the title compound as a beige solid (0.61 g, 58% yield).

MS (ESI, m/z): 357.3 [M+H$^+$].

Preparation T: rac-methanesulfonic acid 4-oxo-1,2-dihydro-4H-pyrrolo[3,2,1-ij]quinolin-2-ylmethyl ester T.i. rac-3-(2-methoxy-quinolin-8-yl)-propane-1,2-diol A mixture of trifluoro-methanesulfonic acid 2-methoxy-quinolin-8-yl ester (3.07 g, 10 mmol, prepared according to WO 2006/021448), allyltributylstannane (3.8 mL, 1.25 eq.), Pd(PPh$_3$)$_4$ (0.29 g, 0.025 eq.) and LiCl (1.6 g, 3.75 eq.) in DMF (20 mL) was stirred at 100° C. for 3 h. After cooling to rt, the mixture was poured on water and extracted with EA. The aq. layer was extracted once more with EA and the combined org. layers were washed with water and brine, dried over MgSO$_4$ and concentrated. The residue was purified by CC (Hept/EA 9:1) to give 8-allyl-2-methoxy-quinoline which was contaminated with stannane residues. This crude oil was dihydroxylated following General Method F using AD-mix β, was affording, after purification by CC (Hept/EA 2:1, 1:1, EA) a colourless solid (2.04 g, 87% yield).

$^1$H NMR (CDCl$_3$) δ: 8.02 (d, J=8.8 Hz, 1H), 7.63 (m, 1H), 7.51 (m, 1H), 7.34 (m, 1H), 6.93 (d, J=8.8 Hz, 1H), 4.10 (m, 1H), 4.10 (s, 3H); 3.62 (m, 1H), 3.49 (m, 1H), 3.37 (m, 2H), 3.09 (s, 1H).

T.ii. rac-1-(tert-butyl-dimethyl-silanyloxy)-3-(2-methoxy-quinolin-8-yl)-propan-2-ol Starting from intermediate T.i (20.3 g; 8.70 mmol) and using General Method G, the title compound was obtained a colourless oil (2.87 g; 95% yield).

$^1$H NMR (CDCl$_3$) δ: 8.00 (d, J=8.8 Hz, 1H), 7.62 (m, 1H), 7.54 (m, 1H), 7.33 (m, 1H), 6.91 (d, J=8.8 Hz, 1H), 4.10 (s, 3H), 4.07 (m, 1H), 3.65 (m, 1H), 3.53 (dd, J=10.0, 6.4 Hz, 1H), 3.37 (m, 2H), 0.91 (s, 9H), 0.08 (s, 6H).

T.iii. rac-methanesulfonic acid 1-(tert-butyl-dimethyl-silanyloxymethyl)-2-(2-methoxyquinolin-8-yl)-ethyl ester Starting from intermediate T.ii (2.80 g, 8.03 mmol) and using General Method C, the title compound was obtained a yellow oil (3.0 g; 88% yield).

$^1$H NMR (CDCl$_3$) δ: 7.98 (d, J=9.1 Hz, 1H), 7.60 (m, 2H), 7.30 (m, 1H), 6.92 (d, J=8.8 Hz, 1H), 5.29 (m, 1H), 4.07 (m, 3H), 3.82 (d, J=4.7 Hz, 2H), 3.71 (dd, J=13.2, 5.9 Hz, 1H), 3.42 (dd, J=13.2, 7.9 Hz, 1H), 2.48 (s, 3H), 0.91 (s, 9H), 0.07 (s, 6H).

T.iv. rac-2-(tert-butyl-dimethyl-silanyloxymethyl)-1, 2-dihydro-pyrrolo[3,2,1-ij]quinolin-4-one A solution of intermediate T.iii (3.0 g; 7.05 mmol) in DCE (40 mL) was heated at 85° C. overnight. The solvent was T.v. rac-2-hydroxymethyl-1,2-dihydro-pyrrolo[3,2,1-ij]quinolin-4-one Starting from intermediate T.iv (2.21 g; 7 mmol) and using General Method E, the title compound was obtained as a colourless solid (1.40 g; purity: about 70%; contaminated with NBu$_4$ salts), which was used as such without further purification in the next step.
MS (ESI, m/z): 202.3 [M+H$^+$].

T.vi. rac-methanesulfonic acid 4-oxo-1,2-dihydro-4H-pyrrolo[3,2,1-ij]quinolin-2-ylmethyl ester Starting from intermediate T.v (1.40 g, 7 mmol) and using General Method C, the title compound was obtained as a beige solid (1.3 g; 95% yield).
MS (ESI, m/z): 280.4 [M+H$^+$].

Preparation U: 6-[(R)-5-(2-amino-ethyl)-2-oxo-oxazolidin-3-yl]-4H-benzo[1,4]thiazin-3-one U.i. 6-[(R)-5-(2-azido-ethyl)-2-oxo-oxazolidin-3-yl]-4H-benzo[1,4]thiazin-3-one In analogy to Preparation A step A.xi, the compound of Preparation P (2.5 g; 6.71 mmol) was reacted with NaN$_3$, affording a beige solid (1.9 g; 89% yield).
MS (ESI, m/z): 320.2 [M+H$^+$].

U.ii. 6-[(R)-5-(2-amino-ethyl)-2-oxo-oxazolidin-3-yl]-4H-benzo[1,4]thiazin-3-one A solution of intermediate U.i (1.8 g; 5.63 mmol) in MeOH/THF (70 mL, 1:2) was hydrogenated over 10% Pd/C for 2 h. The catalyst was filtered off and the filtrate was evaporated under reduced pressure. The residue was stirred in ether, affording a colourless solid (1.40 g; 85% yield).
MS (ESI, m/z): 294.4 [M+H$^+$].

Preparation V: rac-2-aminomethyl-1,2-dihydro-pyrrolo[3,2,1-ij]quinolin-4-one

V.i. rac-2-azidomethyl-1,2-dihydro-pyrrolo[3,2,1-ij]quinolin-4-one

In analogy to Preparation A, step A.xi, a solution of intermediate T.vi (1.2 g; 4.29 mmol) in DMF was reacted with NaN$_3$, affording a yellow oil (900 mg; 93% yield).
MS (ESI, m/z): 227.4 [M+H$^+$].

V.ii. rac-2-aminomethyl-1,2-dihydro-pyrrolo[3,2,1-ij]quinolin-4-one

In analogy to Preparation A, step A.xii, intermediate V.i (850 mg; 3.75 mmol) was reacted with PPh$_3$/H$_2$O, affording a yellow oil (260 mg; 35% yield).
MS (ESI, m/z): 201.4 [M+H$^+$].

Preparation W: 6-[(R)-5-(2-iodo-ethyl)-2-oxo-oxazolidin-3-yl]-4H-benzo[1,4]oxazin-3-one In analogy to Preparation H, step H.v, the compound of Preparation R (1.16 g; 3.25 mmol) was reacted with NaI, affording an off-white solid (0.91 g; 72% yield).
MS (ESI, m/z): 389.0 [M+H$^+$]

Preparation X: (S)-5-aminomethyl-5,6-dihydro-pyrrolo[1,2,3-de]quinoxalin-3-one

X.i. 8-allyl-2-methoxy-quinoxaline

A suspension of 8-(bromomethyl)-2-methoxy-quinoxaline (8.0 g; prepared according to WO 2008/078305) and K$_2$CO$_3$ (8.74 g) in dioxane (154 mL) and water (20 mL) was degassed by bubbling N$_2$ through for 20 min and treated with Pd(dppf)Cl$_2$.DCM complex (1:1) (521 mg) and vinylboronic anhydride pyridine complex (5.12 g). The reaction was further stirred at 110° C. for 2 days and partitioned between water and ether. The org. phase was washed with water and brine, dried over MgSO$_4$, concentrated under reduced pressure and purified by CC (Hex/EA 9:1 to 4:1), affording a yellow liquid (4.70 g, 74% yield).
$^1$H NMR (CDCl$_3$) δ: 8.47 (s, 1H), 7.89 (dd, J=7.6, 1.8 Hz, 1H), 7.51 (m, 2H), 6.12 (m, 1H), 5.13 (m, 2H), 4.10 (s, 4H), 3.93 (d, J=6.7 Hz, 2H).

X.ii. (R)-3-(3-methoxy-quinoxalin-5-yl)-propane-1,2-diol

Intermediate X.i (4.7 g) was dihydroxylated using AD-mix β according to General Method F. The desired diol was isolated after CC (EA, EA/MeOH 9:1) as a colourless oil (5 g, 91% yield)
$^1$H NMR (CDCl$_3$) δ: 8.50 (s, 1H), 7.93 (m, 1H), 7.54 (m, 2H), 4.10 (s, 3H), 4.10 (m, 1H), 3.64 (m, 1H), 3.51 (m, 1H), 3.35 (m, 2H).

X.iii. (R)-1-(tert-butyl-dimethyl-silanyloxy)-3-(3-methoxy-quinoxalin-5-yl)-propan-2-ol Starting from intermediate X.ii (5.0 g) and using General Method G, the title compound was obtained as a colourless solid (6.10 g; 82% yield) after purification by CC (Hept/EA 1:1).
$^1$H NMR (CDCl$_3$) δ: 8.49 (s, 1H), 7.92 (m, 1H), 7.60 (m, 1H), 7.51 (m, 1H), 4.10 (m, 1H), 4.09 (s, 3H), 3.60 (dd, J=5.6, 1.2 Hz, 2H), 3.34 (m, 2H), 0.92 (s, 9H), 0.08 (s, 6H).

X.iv. (S)-5-(tert-butyl-dimethyl-silanyloxymethyl)-5,6-dihydropyrrolo[1,2,3-de]quinoxalin-3-one Starting from intermediate X.iii (6.0 g) and using General Method C for the formation of the mesylate, followed by heating of the reaction mixture for 3 days at 80° C. to complete the cyclisation, the title compound was obtained as a beige solid (4.80 g; 88% yield).
$^1$H NMR (CDCl$_3$) δ: 8.23 (s, 1H), 7.64 (dd, J=8.2, 0.9 Hz, 1H), 7.35 (dd, J=7.0, 0.9 Hz, 1H), 7.24 (m, 1H), 5.05 (m, 1H), 4.33 (dd, J=10.5, 3.8 Hz, 1H), 3.92 (dd, J=10.5, 2.3 Hz, 1H), 3.45 (m, 2H), 0.61 (m, 9H), −0.03 (s, 3H), −0.18 (s, 3H).

X.v. (S)-5-hydroxymethyl-5,6-dihydro-pyrrolo[1,2,3-de]quinoxalin-3-one

Starting from intermediate X.iv (4.80 g) and using General Method E, the title compound was obtained as a beige solid (2.60 g; 85% yield).
$^1$H NMR (DMSO d6) δ: 8.13 (s, 1H), 7.59 (d, J=7.9 Hz, 1H), 7.43 (d, J=7.0 Hz, 1H), 7.25 (dd, J=7.9, 7.0 Hz, 1H), 4.94 (m, 2H), 4.11 (m, 1H), 3.66 (m, 1H), 3.45 (m, 1H), 3.29 (m, 1H).

X.vi. Methanesulfonic acid (S)-3-oxo-5,6-dihydro-3H-pyrrolo[1,2,3-de]quinoxalin-5-ylmethyl ester Starting from intermediate X.v (2.60 g) and using General Method C, the title compound was obtained as a beige solid (3.0 g; 83% yield).

¹H NMR (CDCl₃) δ: 8.24 (s, 1H), 7.70 (d, J=8.2 Hz, 1H), 7.40 (d, J=7.3 Hz, 1H), 7.30 (m, 1H), 5.22 (m, 1H), 5.04 (dd, J=10.5, 4.4 Hz, 1H), 4.64 (dd, J=10.5, 2.6 Hz, 1H), 3.62 (m, 1H), 3.48 (m, 1H), 2.92 (s, 3H).

X.vii. (S)-5-azidomethyl-5,6-dihydro-pyrrolo[1,2,3-de]quinoxalin-3-one

In analogy to Preparation A, step A.xi, a solution of intermediate X.vi (3.0 g) in DMF was reacted with NaN₃, affording a beige solid (1.90 g; 78% yield).
¹H NMR (CDCl₃) δ: 8.24 (s, 1H), 7.69 (d, J=7.9 Hz, 1H), 7.39 (m, 1H), 7.29 (m, 1H), 5.10 (m, 1H), 4.26 (dd, J=12.6, 5.3 Hz, 1H), 3.84 (dd, J=12.6, 2.9 Hz, 1H), 3.55 (m, 1H), 3.34 (m, 1H).

X.viii. (S)-5-aminomethyl-5,6-dihydro-pyrrolo[1,2,3-de]quinoxalin-3-one

In analogy to Preparation A, step A.xii, intermediate X.vii (1.40 g) was reacted with PPh₃/H₂O, affording a brown foam (1.40 g; 83% yield).
MS (ESI, m/z): 202.3 [M+H⁺].

Preparation Y: rac-methanesulfonic acid 2-{3-[4-(4-methoxy-benzyl)-3-oxo-3,4-dihydro-2H-pyrido[3,2-b][1,4]oxazin-6-yl]-2-oxo-oxazolidin-5-yl}-ethyl ester Y.i. 6-bromo-4-(4-methoxy-benzyl)-4H-pyrido[3,2-b][1,4]oxazin-3-one
A suspension of 6-bromo-2H-pyrido[3,2-b]-1,4-oxazin-3 (4H)-one (2.0 g; prepared according to WO 01/30782) in DMF (40 mL) was treated with 4-methoxybenzyl chloride (1.18 mL) and Cs₂CO₃ (8.5 g) and stirred at rt for 2 h. The solvent was evaporated under reduced pressure and the residue was partitioned between EA and water. The org. layer was washed with brine, dried over MgSO₄ and evaporated under reduced pressure. The residue was triturated with Hept, affording a beige solid (2.8 g, 92% yield).
¹H NMR (CDCl₃) δ: 7.49 (d, J=8.8 Hz, 2H), 7.05 (s, 2H), 6.83 (d, J=8.8 Hz, 2H), 6.83 (d, J=8.8 Hz, 2H), 6.83 (d, J=8.8 Hz, 2H), 4.67 (s, 2H), 3.77 (s, 3H).

Y.ii. rac-1-azido-4-(tent-butyl-dimethyl-silanyloxy)-butan-2-ol

A solution of 2-[2-[[(tert-butyl)dimethylsilyl]oxy]ethyl]-oxirane (5.0 g; prepared according to WO 2007/144423) in MeOH (150 mL) was reacted with NaN₃ (3.95 g) and NH₄Cl (2.37 g). The reaction mixture was further stirred at 80° C. overnight. The solvent was evaporated under reduced pressure and the residue was partitioned between EA and water. The org layer was washed with brine, dried over Na₂SO₄ and evaporated under reduced pressure, affording a yellow oil (4.9 g, 81% yield).
¹H NMR (CDCl₃) δ: 4.01 (m, 1H), 3.87 (m, 2H), 3.30 (m, 2H), 1.72 (m, 2H), 0.90 (s, 9H), 0.08 (s, 6H).

Y.iii. rac-1-amino-4-(tert-butyl-dimethyl-silanyloxy)-butan-2-ol

A solution of intermediate Y.ii (4.85 g) in THF (100 mL) was hydrogenated for 3 h over 10% Pd/C (1.0 g). The catalyst was filtered off and the filtrate was evaporated under reduced pressure, affording a yellow oil (4.1 g, 94.5% yield).
MS (ESI, m/z): 219.8 [M+H⁺].

Y.iv. rac-5-[2-(tert-butyl-dimethyl-silanyloxy)-ethyl]-oxazolidin-2-one

Starting from intermediate Y.iii (4.0 g) and using General method D, the title compound was obtained as a light yellow oil (3.3 g; 73.8% yield).

¹H NMR (CDCl₃) δ: 5.22 (br., 1H), 4.80 (m, 1H), 3.74 (m, 3H), 3.33 (m, 1H), 1.93 (m, 2H), 0.89 (m, 9H), 0.07 (m, 6H).

Y.v. rac-6-{5-[2-(tert-butyl-dimethyl-silanyloxy)-ethyl]-2-oxa-oxazolidin-3-yl}-4-(4-methoxy-benzyl)-4H-pyrido[3,2-b][1,4]oxazin-3-one Intermediates Y.iv (1.97 g) and Y.i (2.8 g), CuI (305 mg) and K₂CO₃ (2.2 g) were placed in a round bottom flask and the flask was flushed with argon. Trans-1,2-diaminocyclohexane (1.2 mL) and dioxane (60 mL) were added to the mixture and the reaction flask was again flushed with argon. The reaction mixture was stirred at 100° C. for 2 days and partitioned between EA and water. The org. layer was washed with brine, dried over MgSO₄ and evaporated under reduced pressure. The residue was purified by CC (DCM/MeOH 19:1) affording, after crystallisation from Hept, a colourless solid (1.7 g, 41% yield).
¹H NMR (CDCl₃) δ: 7.81 (d, J=8.8 Hz, 1H), 7.28 (m, 3H), 6.81 (m, 2H), 5.20 (s, 2H), 4.82 (m, 1H), 4.28 (m, 1H), 3.85 (m, 3H), 3.77 (s, 3H), 2.00 (m, 2H), 0.89 (s, 9H), 0.07 (s, 6H).

Y.vi. rac-6-[5-(2-hydroxy-ethyl)-2-oxo-oxazolidin-3-yl]-4-(4-methoxy-benzyl)-4H-pyrido[3,2-b][1,4]oxazin-3-one Starting from intermediate Y.v (1.7 g) and using General Method E, the title compound was obtained after purification by CC (EA then EA/MeOH 9:1) as a yellow oil (1.4 g; 100% yield).
MS (ESI, m/z): 400.0 [M+H⁺].

Y.vii. rac-methanesulfonic acid 2-{3-[4-(4-methoxy-benzyl)-3-oxo-3,4-dihydro-2H-pyrido[3,2-b][1,4]oxazin-6-yl]-2-oxa-oxazolidin-5-yl}-ethyl ester Starting from intermediate Y.vi (1.32 g) and using General Method C, the title compound was obtained as a colourless foam (1.3 g; 82.5% yield)
MS (ESI, m/z): 477.8 [M+H⁺].

EXAMPLES

Example 1

2-(RS)-({[(R)-2-oxo-3-(3-oxo-3,4-dihydro-2H-benzo[1,4]thiazin-6-yl)-oxazolidin-5-ylmethyl]-amino}-methyl)-2,3-dihydro-1-oxa-3a,7-diaza-phenalen-4-one The title compound, prepared following General Method B and starting from the compound of Preparation F (0.065 g, 0.3 mmol) and the compound of Preparation H (0.117 g, 0.3 mmol), was isolated after crystallization from ether/MeOH as a yellowish solid (0.025 g, 17% yield).
MS (ESI, m/z): 480.2 [M+H⁺].

Example 2

2-(RS)-({[(R)-2-oxo-3-(3-oxo-3,4-dihydro-2H-benzo[1,4]oxazin-6-yl)-oxazolidin-5-ylmethyl]-amino}-methyl)-2,3-dihydro-1-oxa-3a,7-diaza-phenalen-4-one The title compound, prepared following General Method B and starting from the compound of Preparation F (0.065 g, 0.3 mmol) and the compound of Preparation I (0.103 g, 0.3 mmol), was isolated after crystallization from ether/MeOH as a colourless solid (0.03 g, 21% yield).

¹H NMR (d6-DMSO) δ: 10.68 (m, 1H), 8.32 (d, J=5.3 Hz, 1H), 7.91 (d, J=10.0 Hz, 1H), 7.30 (m, 1H), 7.09 (dd, J=5.3, 2.6 Hz, 1H), 6.88 (m, 3H), 4.52 (m, 4H), 4.03 (d, J=1.2 Hz, 1H), 3.75 (m, 2H), 2.96 (m, 4H).
MS (ESI, m/z): 464.4 [M+H⁺].

Example 3

(6RS)-8-fluoro-6-({[(R)-2-oxo-3-(3-oxo-3,4-dihydro-2H-benzo[1,4]thiazin-6-yl)-oxazolidin-5-ylmethyl]-amino}-methyl)-6,7-dihydro-5H-pyrido[3,2,1-ij]quinolin-3-one Starting from the compound of Preparation G and the compound of Preparation H and using General Method B, the title compound was obtained as a beige solid (27 mg, 20% yield).
¹H NMR (DMSO-d6) δ: 10.53 (s, 1H), 7.86 (d, J=9.7 Hz, 1H), 7.59 (m, 1H), 7.31 (m, 2H), 7.08 (m, 2H), 6.53 (d, J=9.4 Hz, 1H), 4.71 (m, 1H), 4.50 (m, 1H), 4.04 (m, 1H), 3.76 (m, 1H), 3.43 (m, 3H), 3.03 (m, 1H), 2.86 (m, 2H), 2.67 (m, 3H), 2.10 (m, 1H).
MS (ESI, m/z): 495.1 [M+H⁺].

Example 4

(6RS)-8-fluoro-6-({[(R)-2-oxo-3-(3-oxo-3,4-dihydro-2H-benzo[1,4]oxazin-6-yl)-oxazolidin-5-ylmethyl]-amino}-methyl)-6,7-dihydro-5H-pyrido[3,2,1-ij]quinolin-3-one Starting from the compound of Preparation G and the compound of Preparation I and using General Method B, the title compound was obtained as a beige solid (18 mg, 13% yield).
¹H NMR (CDCl₃) δ: 9.86, 9.56 (2 s, 1H), 7.64 (m, 1H), 7.41 (m, 2H), 6.93 (m, 3H), 6.71 (m, 1H), 4.95 (m, 1H), 4.74 (m, 1H), 4.55 (s, 2H), 4.12 (m, 1H), 3.97 (m, 1H), 3.48 (m, 1H), 3.16 (m, 2H), 2.79 (m, 2H), 2.52 (m, 2H), 2.17 (m, 1H), 1.85 (m, 1H).
MS (ESI, m/z): 479.1 [M+H⁺].

Example 5

(6RS)-6-({[(R)-3-(2,3-dihydro-benzo[1,4]dioxin-6-yl)-2-oxo-oxazolidin-5-ylmethyl]-amino}-methyl)-8-fluoro-6,7-dihydro-5H-pyrido[3,2,1-ij]quinolin-3-one Starting from the compound of Preparation G and the compound of Preparation J and using General Method B, the title compound was obtained as a colourless foam (3 mg, 37% yield).
¹H NMR (CDCl₃) δ: 7.62 (d, J=9.7 Hz, 1H), 7.37 (m, 1H), 7.10 (d, J=2.1 Hz, 1H), 6.93 (m, 3H), 6.63 (d, J=9.7 Hz, 1H), 4.67 (m, 2H), 4.24 (s, 4H), 3.99 (t, J=8.5 Hz, 1H), 3.83 (m, 1H), 3.59 (m, 1H), 3.16 (m, 1H), 2.96 (m, 2H), 2.81 (m, 2H), 2.59 (m, 1H), 2.18 (m, 1H).
MS (ESI, m/z): 466.2 [M+H⁺].

Example 6

(R)-9-fluoro-2-({[(R)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one Starting from the compound of Preparation A and the compound of Preparation H and using General Method B, the title compound was obtained as a colourless foam (50 mg, 28% yield).

¹H NMR (CDCl₃) δ: 8.26 (s, 1H), 7.65 (d, J=9.4 Hz, 1H), 7.43 (d, J=2.3 Hz, 1H), 7.35 (m, 1H), 7.27 (m, 1H), 6.90 (dd, J=8.5, 2.3 Hz, 1H), 6.85 (t, J=8.8 Hz, 1H), 6.59 (d, J=9.4 Hz, 1H), 5.06 (m, 1H), 4.68 (m, 1H), 3.98 (t, J=8.8 Hz, 1H), 3.79 (dd, J=8.5, 6.4 Hz, 1H), 3.52 (m, 1H), 3.41 (s, 3H), 3.26 (m, 2H), 3.00 (m, 1H), 1.63 (s, 1H).
MS (ESI, m/z): 481.3 [M+H⁺].

Example 7

(6RS)-8-fluoro-6-{2-[(RS)-2-oxo-3-(3-oxo-3,4-dihydro-2H-benzo[1,4]thiazin-6-yl)-oxazolidin-5-yl]-ethylamino}-6,7-dihydro-5H-pyrido[3,2,1-ij]quinolin-3-one Starting from the compound of Preparation E and the compound of Preparation K and using General Method B, the title compound was obtained as a pale yellow solid (6 mg, 10% yield).
MS (ESI, m/z): 495.1 [M+H⁺].

Example 8

(R)-9-fluoro-2-({[(R)-2-oxo-3-(3-oxo-3,4-dihydro-2H-benzo[1,4]oxazin-6-yl)-oxazolidin-5-ylmethyl]-amino}-methyl)-1,2-dihydro-pyrrolo[3,2,1-ij]quinolin-4-one Starting from the compound of Preparation A and the compound of Preparation I and using General Method B, the title compound was obtained as a colourless solid (43 mg, 25% yield).
MS (ESI, m/z): 465.3 [M+H⁺].

Example 9

(RS)-9-fluoro-2-({[(R)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one Starting from the compound of Preparation B and the compound of Preparation H and using General Method B, the title compound was obtained as a colourless solid (84 mg, 48% yield).
MS (ESI, m/z): 481.2 [M+H⁺].

Example 10

(R)-9-fluoro-2-({2-[(RS)-2-oxo-3-(3-oxo-3,4-dihydro-2H-benzo[1,4]thiazin-6-yl)-oxazolidin-5-yl]-ethylamino}-methyl)-1,2-dihydropyrrolo[3,2,1-ij]quinolin-4-one Starting from the compound of Preparation A and the compound of Preparation K and using General Method B, the title compound was obtained as a pale yellow solid (32 mg, 24% yield).
¹H NMR (CDCl₃) δ: 8.12 (s, 1H), 7.67 (m, 1H), 7.38 (m, 2H), 7.27 (m, 1H), 6.90 (m, 2H), 6.60 (m, 1H), 5.09 (m, 1H), 4.65 (m, 1H), 4.00 (m, 1H), 3.65 (m, 2H), 3.41 (s, 2H), 3.22 (m, 3H), 2.86 (m, 2H), 1.98 (m, 2H), 1.60 (s, 1H).
MS (ESI, m/z): 495.2 [M+H⁺].

Example 11

(RS)-2-({[(R)-2-oxo-3-(3-oxo-3,4-dihydro-2H-benzo[1,4]thiazin-6-yl)-oxazolidin-5-ylmethyl]-amino}-methyl)-2,3-dihydro-1-oxa-3a-aza-phenalen-4-one Starting from the compound of Preparation C and the compound of Preparation H and using General Method B, the title compound was obtained as a pale yellow solid (41 mg, 29% yield).
MS (ESI, m/z): 479.1 [M+H$^+$].

Example 12

(RS)-9-fluoro-2-({[(R)-2-oxo-3-(3-oxo-3,4-dihydro-2H-benzo[1,4]thiazin-6-yl)-oxazolidin-5-ylmethyl]-amino}-methyl)-2,3-dihydro-1-oxa-3a-aza-phenalen-4-one Starting from the compound of Preparation D and the compound of Preparation H and using General Method B, the title compound was obtained as a pale yellow solid (32 mg, 21% yield).
MS (ESI, m/z): 497.1 [M+H$^+$].

Example 13

(RS)-3-fluoro-5-({[(R)-2-oxo-3-(3-oxo-3,4-dihydro-2H-benzo[1,4]thiazin-6-yl)-oxazolidin-5-ylmethyl]-amino}-methyl)-5,6-dihydro-4H-1,6a-diaza-phenalen-7-one Starting from the compound of Preparation L and the compound of Preparation H and using General Method B, the title compound was obtained as a pale yellow solid (56 mg, 37% yield).
$^1$H NMR (CDCl$_3$) δ: 9.15 (s, 0.5H), 8.95 (s, 0.5H), 8.38 (d, J=0.9 Hz, 1H), 7.90 (dd, J=10.0, 3.2 Hz, 1H), 7.42 (dd, J=23.4, 2.3 Hz, 1H), 7.28 (m, 1H), 7.13 (dd, J=12.3, 2.1 Hz, 1H), 6.97 (dd, J=13.5, 10.0 Hz, 1H), 4.76 (m, 2H), 4.20-4.00 (m, 2H), 3.50 (m, 1H), 3.41 (s, 2H), 3.11 (m, 3H), 2.95-2.50 (m, 3H), 2.20 (m, 1H).
MS (ESI, m/z): 496.3 [M+H$^+$].

Example 14

(RS)-3-fluoro-5-({[(R)-2-oxo-3-(3-oxo-3,4-dihydro-2H-benzo[1,4]oxazin-6-yl)-oxazolidin-5-ylmethyl]-amino}-methyl)-5,6-dihydro-4H-1,6a-diaza-phenalen-7-one Starting from the compound of Preparation L and the compound of Preparation I and using General Method B, the title compound was obtained as a colourless solid (27 mg, 19% yield). $^1$H NMR (DMSO-d6) δ: 10.69 (s, 1H), 8.46 (d, J=0.6 Hz, 1H), 7.90 (d, J=9.7 Hz, 1H), 7.32 (m, 1H), 6.93 (m, 2H), 6.79 (dd, J=9.7, 1.5 Hz, 1H), 4.69 (m, 1H), 4.52 (s, 2H), 4.47 (m, 1H), 4.02 (t, J=8.8 Hz, 1H), 3.75 (m, 1H), 3.47 (m, 1H), 3.07 (m, 1H), 2.84 (m, 2H), 2.61 (m, 3H), 2.20 (m, 1H).
MS (ESI, m/z): 480.4 [M+H$^+$].

Example 15

(RS)-3-fluoro-5-({2-[(R)-2-oxo-3-(3-oxo-3,4-dihydro-2H-benzo[1,4]thiazin-6-yl)-oxazolidin-5-yl]-ethylamino}-methyl)-4,5-dihydropyrrolo[3,2,1-de][1,5]naphthyridin-7-one Starting from the compound of Preparation O and the compound of Preparation P and using General Method B, the title compound was obtained as a colourless solid (110 mg, 24% yield).
$^1$H NMR (DMSO-d6) δ: 10.59 (s, 1H), 8.50 (d, J=1.2 Hz, 1H), 8.03 (d, J=9.7 Hz, 1H), 7.32 (m, 2H), 7.07 (dd, J=8.5, 2.3 Hz, 1H), 6.82 (d, J=9.7 Hz, 1H), 5.32 (m, 1H), 4.80 (m, 1H), 4.14 (m, 1H), 3.73 (m, 2H), 3.58 (m, 3H), 3.42 (s, 2H), 3.14 (m, 2H), 2.15 (m, 2H).
MS (ESI, m/z): 496.2 [M+H$^+$].

Example 16

(S)-9-fluoro-2-({[(R)-2-oxo-3-(3-oxo-3,4-dihydro-2H-benzo[1,4]oxazin-6-yl)-oxazolidin-5-ylmethyl]-amino}-methyl)-1,2-dihydro-pyrrolo[3,2,1-ij]quinolin-4-one Starting from the compound of Preparation N and the compound of Preparation I and using General Method B, the title compound was obtained as a colourless solid (67 mg, 39% yield).
MS (EST, m/z): 465.3 [M+H$^+$].

Example 17

(S)-9-fluoro-2-({2-[(R)-2-oxo-3-(3-oxo-3,4-dihydro-2H-benzo[1,4]thiazin-6-yl)-oxazolidin-5-yl]-ethylamino}-methyl)-1,2-dihydro-1.5 pyrrolo[3,2,1-ij]quinolin-4-one Starting from the compound of Preparation N and the compound of Preparation P and using General Method B, the title compound was obtained as a colourless solid (67 mg, 45% yield).
MS (ESI, m/z): 495.1 [M+H$^+$].

Example 18

(R)-9-fluoro-2-({2-[(R)-2-oxo-3-(3-oxo-3,4-dihydro-2H-benzo[1,4]thiazin-6-yl)-oxazolidin-5-yl]-ethylamino}-methyl)-1,2-dihydropyrrolo[3,2,1-ij]quinolin-4-one Starting from the compound of Preparation A and the compound of Preparation P and using General Method B, the title compound was obtained as a colourless solid (24 mg, 18% yield).
MS (ESI, m/z): 495.2 [M+H$^+$].

Example 19

(S)-9-fluoro-2-({2-[(S)-2-oxo-3-(3-oxo-3,4-dihydro-2H-benzo[1,4]thiazin-6-yl)-oxazolidin-5-yl]-ethylamino}-methyl)-1,2-dihydropyrrolo[3,2,1-ij]quinolin-4-one Starting from the compound of Preparation N and the compound of Preparation Q and using General Method B, the title compound was obtained as a beige solid (71 mg, 48% yield).
$^1$H NMR (CDCl$_3$) δ: 8.01 (m, 1H), 7.67 (d, J=9.4 Hz, 1H), 7.39 (m, 2H), 7.28 (m, 1H), 6.90 (m, 2H), 6.59 (d, J=9.4 Hz, 1H), 5.11 (m, 1H), 4.71 (m, 1H), 4.01 (t, J=8.5 Hz, 1H), 3.57 (m, 2H), 3.41 (s, 2H), 3.26 (m, 2H), 2.88 (m, 2H), 1.94 (m, 2H).
MS (ESI, m/z): 495.1 [M+H$^+$].

Example 20

(R)-9-fluoro-2-({2-[(S)-2-oxo-3-(3-oxo-3,4-dihydro-2H-benzo[1,4]thiazin-6-yl)-oxazolidin-5-yl]-ethylamino}-methyl)-1,2-dihydropyrrolo[3,2,1-ij]quinolin-4-one Starting from the compound of Preparation A and the compound of Preparation Q and using General Method B, the title compound was obtained as a beige solid (75 mg, 55% yield).
MS (ESI, m/z): 495.3 [M+H$^+$].

Example 21

(RS)-9-fluoro-2-({2-[(R)-2-oxo-3-(3-oxo-3,4-dihydro-2H-benzo[1,4]oxazin-6-yl)-oxazolidin-5-yl]-ethylamino}-methyl)-1,2-dihydropyrrolo[3,2,1-ij]quinolin-4-one Starting from the compound of Preparation B and the compound of Preparation R and using General Method B, the title compound was obtained as a colourless solid (46 mg, 39% yield).

$^1$H NMR (CDCl$_3$) δ: 7.67 (m, 1H), 7.43 (m, 2H), 6.91 (m, 2H), 6.78 (dd, J=5.9, 2.6 Hz, 1H), 6.60 (dd, J=9.7, 1.5 Hz, 1H), 5.08 (m, 1H), 4.69 (s, 1H), 4.59 (s, 2H), 3.99 (t, J=8.8 Hz, 1H), 3.59 (m, 2H), 3.22 (m, 3H), 2.86 (m, 2H), 1.89 (m, 2H).

MS (ESI, tri/z): 479.2 [M+H$^+$].

Example 22

(RS)-9-fluoro-2-({2-[(S)-2-oxo-3-(3-oxo-3,4-dihydro-2H-benzo[1,4]oxazin-6-yl)-oxazolidin-5-yl]-ethylamino}-methyl)-1,2-dihydropyrrolo[3,2,1-ij]quinolin-4-one Starting from the compound of Preparation B and the compound of Preparation S and using General Method B, the title compound was obtained as a colourless solid (31 mg, 26% yield).

$^1$H NMR (CDCl$_3$) δ: 7.67 (m, 1H), 7.43 (m, 2H), 6.91 (m, 2H), 6.78 (dd, J=5.9, 2.6 Hz, 1H), 6.60 (dd, J=9.7, 1.5 Hz, 1H), 5.08 (m, 1H), 4.69 (s, 1H), 4.59 (s, 2H), 3.99 (t, J=8.8 Hz, 1H), 3.59 (m, 2H), 3.22 (m, 3H), 2.86 (m, 2H), 1.89 (m, 2H).

MS (ESI, m/z): 479.2 [M+H$^+$].

Example 23

(RS)-9-fluoro-2-({2-[(R)-2-oxo-3-(3-oxo-3,4-dihydro-2H-benzo[1,4]oxazin-6-yl)-oxazolidin-5-yl]-ethylamino}-methyl)-1,2,5,6-tetrahydropyrrolo[3,2,1-ij]quinolin-4-one A solution of the compound of Example 21 (30 mg, 0.063 mmol) in MeOH (4 mL) and AcOH (1 mL) was hydrogenated over 10% Pd/C (14 mg) at 50° C. overnight. The catalyst was filtered off, washed with MeOH/DCM and concentrated to afford the title compound as an off-white solid (20 mg, 66% yield).

MS (ESI, m/z): 481.3 [M+H$^+$].

Example 24

(RS)-5-({2-[(R)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one Starting from the compound of Preparation M and the compound of Preparation P and using General Method B, the title compound was obtained as a brown resin (6 mg, 11% yield).

MS (ESI, m/z): 478.0 [M+H$^+$].

Example 25

(RS)-5-({2-[(S)-2-oxo-3-(3-oxo-3,4-dihydro-2H-benzo[1,4]oxazin-6-yl)-oxazolidin-5-yl]-ethylamino}-methyl)-4,5-dihydro-pyrrolo[3,2,1-de][1,5]naphthyridin-7-one Starting from the compound of Preparation M and the compound of Preparation S and using General Method B, the title compound was obtained as a brown oil (10 mg, 19% yield).

MS (ESI, m/z): 462.0 [M+H$^+$].

Example 26

(RS)-2-({2-[(R)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one Starting from the compound of Preparation T and the compound of Preparation U and using General Method B, the title compound was obtained as a beige solid (55 mg, 32% yield).

MS (ESI, m/z): 476.9 [M+H$^+$].

Example 27

(RS)-2-({2-[(R)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1-ij]quinolin-4-one Starting from the compound of Preparation V and the compound of Preparation W and using General Method B, the title compound was obtained as a beige solid (41 mg, 24% yield).

MS (ESI, m/z): 461.0 [M+H$^+$].

Example 28

(RS)-2-({[(R)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one Starting from the compound of Preparation V and the compound of Preparation H and using General Method B, the title compound was obtained as a beige solid (42 mg, 24% yield).

MS (ESI, m/z): 463.0 [M+H$^+$].

Example 29

(S)-5-({2-[(S)-2-oxo-3-(3-oxo-3,4-dihydro-2H-benzo[1,4]thiazin-6-yl)-oxazolidin-5-yl]-ethylamino}-methyl)-5,6-dihydro-pyrrolo[1,2,3-de]quinoxalin-3-one Starting from the compound of Preparation X and intermediate Q.vi and using General Method B, the title compound was obtained as a beige solid (60 mg, 25% yield).

$^1$H NMR (DMSO d6) δ: 10.53 (s, 1H), 8.12 (s, 1H), 7.59 (d, J=8.5 Hz, 1H), 7.43 (d, J=7.3 Hz, 1H), 7.28 (m, 3H), 6.96 (m, 1H), 4.99 (m, 1H), 4.60 (m, 1H), 3.96 (m, 1H), 3.60 (m, 1H), 3.41 (m, 4H), 3.05 (m, 2H), 2.61 (m, 2H), 1.78 (m, 2H).

MS (ESI, m/z): 478.2 [M+H$^+$].

Example 30

(S)-5-({[(R)-2-oxo-3-(3-oxo-3,4-dihydro-2H-benzo[1,4]thiazin-6-yl) oxazolidin-5-ylmethyl]-amino}-methyl)-5,6-dihydro-pyrrolo[1,2,3-de]quinoxalin-3-one Starting from the compound of Preparation X and the compound of Preparation H and using General Method B, the title compound was obtained as a beige solid (80 mg, 34% yield). MS (ESI, m/z): 464.2 [M+H$^+$].

Example 31

(RS)-5-({2-[(S)-2-oxo-3-(3-oxo-3,4-dihydro-2H-pyrido[3,2-b][1,4]oxazin-6-yl)-oxazolidin-5-yl]-ethylamino}-methyl)-5,6-dihydropyrrolo[1,2,3-de]quinoxalin-3-one 31.i. (RS)-5-[(S)-(2-{3-[4-(4-methoxy-benzyl)-3-oxo-3,4-dihydro-2H-pyrido[3,2-b][1,4]oxazin-6-yl]-2-oxo-oxazolidin-5-yl}-ethylamino)-methyl]-5,6-dihydro-pyrrolo[1,2,3-de]quinoxalin-3-one Starting from the compound of Preparation X and the compound of Preparation Y and using General Method B, the title compound was obtained as a brown oil (250 mg, 47% yield). MS (ESI, m/z): 583.2 [M+H$^+$].

31.ii. (RS)-5-({2-[(S)-2-oxo-3-(3-oxo-3,4-dihydro-2H-pyrido[3,2-b][1,4]oxazin-6-yl)-oxazolidin-5-yl]-ethylamino}-methyl)-5,6-dihydro-pyrrolo[1,2,3-de]quinoxalin-3-one A solution of intermediate 31.i (250 mg) in TFA was stirred in a sealed flask at 90° C. for 2 days. The solvent was removed under reduced pressure and the residue was taken up in DCM and aq. NH$_4$OH. The org. layer was washed with water, brine, dried over MgSO$_4$, evaporated under reduced pressure. The residue was purified by CC (EA/MeOH 9:1 containing 1% NH$_4$OH) and crystallized from ether/EA, affording a beige solid (100 mg; 50% yield).

$^1$H NMR (DMSO d6) δ: 11.15 (m, 1H), 8.12 (s, 1H), 7.57 (m, 2H), 7.41 (m, 2H), 7.25 (m, 1H), 4.98 (m, 1H), 4.62 (m, 1H), 4.59 (s, 2H), 4.12 (m, 1H), 3.68 (m, 1H), 3.43 (m, 1H), 3.33 (m, 1H), 3.04 (m, 2H), 2.61 (m, 2H), 1.78 (m, 2H).

MS (ESI, m/z): 463.2 [M+H$^+$].

Pharmacological Properties of the Invention Compounds
In Vitro Assays
Experimental Methods:

Minimal inhibitory concentrations (MICs, in mg/l) were determined in cation-adjusted Mueller-Hinton Broth by a microdilution method following the description given in "Methods for Dilution Antimicrobial Susceptibility Tests for Bacteria that Grow Aerobically", Approved standard, 7$^{th}$ ed., Clinical and Laboratory Standards Institute (CLSI) Document M7-A7, Wayne, Pa., USA, 2006.

Results:

All Example compounds were tested against several Gram-positive and Gram-negative bacteria.

Typical antibacterial test results are given in the table hereafter (MIC in mg/l).

| Example No. | M. catarrhalis A894 |
| --- | --- |
| 1 | ≤0.063 |
| 2 | 0.5 |
| 3 | ≤0.063 |
| 4 | ≤0.063 |
| 5 | ≤0.063 |
| 6 | ≤0.063 |
| 7 | ≤0.063 |
| 8 | 0.125 |
| 9 | ≤0.063 |
| 10 | ≤0.063 |
| 11 | ≤0.063 |
| 12 | ≤0.063 |
| 13 | ≤0.063 |
| 14 | ≤0.063 |
| 15 | ≤0.063 |
| 16 | 0.125 |
| 17 | ≤0.063 |
| 18 | ≤0.063 |
| 19 | ≤0.063 |
| 20 | ≤0.063 |
| 21 | ≤0.063 |
| 22 | ≤0.063 |
| 23 | ≤0.063 |
| 24 | 2 |
| 25 | 4 |
| 26 | ≤0.063 |
| 27 | ≤0.063 |
| 28 | ≤0.063 |
| 29 | ≤0.063 |
| 30 | 0.125 |
| 31 | ≤0.063 |

The invention claimed is:

1. A compound of formula I wherein n is 0 or 1;

R$^1$ represents H or F;

U represents CH$_2$ or, provided n is 1, O or NH;

"-----" is a bond or is absent;

V represents CH or N when "-----" is a bond, or V represents CH$_2$ or NH when "-----" is absent;

W represents CH or N;

A is —(CH$_2$)$_p$—NH—(CH$_2$)$_q$— wherein p is 1 and q is 1 or 2 or, provided U represents CH$_2$ and n is 1, p may also be 0 and q is then 2;

G represents one of the groups $G^1$ and $G^2$ represented below

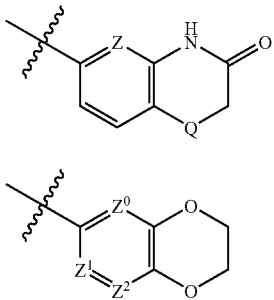

$G^1$ $G^2$ wherein
Z represents N or CH and Q represents O or S; and
$Z^0$, $Z^1$ and $Z^2$ each represent CH, or $Z^0$ and $Z^1$ each represent CH and $Z^2$ represents N, or $Z^0$ represents CH, $Z^1$ represents N and $Z^2$ represents CH or N, or $Z^0$ represents N and $Z^1$ and $Z^2$ each represent CH;
or a salt of such a compound.

2. The compound according to claim 1 of formula $I_{P1}$

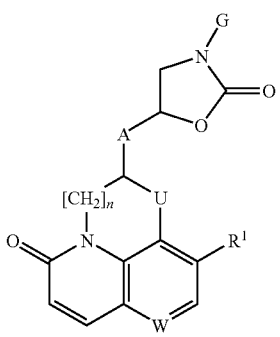

$I_{P1}$ wherein
n is 0 or 1;
$R^1$ represents H or F;
U represents $CH_2$ or, provided n is 1, O;
W represents CH or N;
A is $-(CH_2)_p-NH-(CH_2)_q-$ wherein p is 1 and q is 1 or 2, or, provided U represents $CH_2$ and n is 1,
p may also be 0 and q is then 2;
G represents one of the groups $G^1$ and $G^{2'}$ represented below

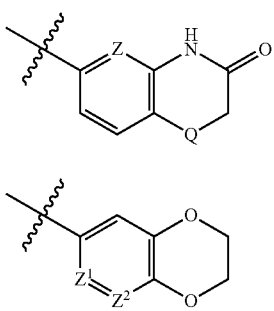

$G^1$ $G^{2'}$ wherein Z, $Z^1$ and $Z^2$ each independently represent N or CH and Q represents O or S;
or a salt of such a compound.

3. A compound of formula I according to claim 1, wherein W represents CH;
or a salt of such a compound.

4. A compound of formula I according to claim 1, wherein W represents N;
or a salt of such a compound.

5. A compound of formula I according to claim 1, wherein $R^1$ represents F;
or a salt of such a compound.

6. A compound of formula I according to claim 1, wherein U represents O;
or a salt of such a compound.

7. A compound of formula I according to claim 1, wherein U represents $CH_2$;
or a salt of such a compound.

8. A compound of formula I according to claim 1, wherein G represents the group $G^1$ and Z represents CH;
or a salt of such a compound.

9. A compound of formula I according to claim 2, wherein G represents the group $G^2$ or $G^{2'}$;
or a salt of such a compound.

10. A compound of formula I according to claim 1, which is:
- -2-({[(R)-2-oxo-3-(3-oxo-3,4-dihydro-2H-benzo[1,4]thiazin-6-yl)-oxazolidin-5-ylmethyl]-amino}-methyl)-2,3-dihydro-1-oxa-3a,7-diaza-phenalen-4-one;
- -2-({[(R)-2-oxo-3-(3-oxo-3,4-dihydro-2H-benzo[1,4]oxazin-6-yl)-oxazolidin-5-ylmethyl]-amino}-methyl)-2,3-dihydro-1-oxa-3a,7-diaza-phenalen-4-one;
- -8-fluoro-6-({[(R)-2-oxo-3-(3-oxo-3,4-dihydro-2H-benzo[1,4]thiazin-6-yl)-oxazolidin -5-ylmethyl]-amino}-methyl)-6,7-dihydro-5H-pyrido[3,2,1-ij]quinolin-3-one;
- -8-fluoro-6-({[(R)-2-oxo-3-(3-oxo-3,4-dihydro-2H-benzo[1,4]oxazin-6-yl)-oxazolidin -5-ylmethyl]-amino}-methyl)-6,7-dihydro-5H-pyrido[3,2,1-ij]quinolin-3-one;
- -6-({[(R)-3-(2,3-dihydro-benzo[1,4]dioxin-6-yl)-2-oxo-oxazolidin-5-ylmethyl]-amino}-methyl) -8-fluoro-6,7-dihydro-5H-pyrido[3,2,1-ij]quinolin-3-one;
- -(R)-9-fluoro-2-({[(R)-2-oxo-3-(3-oxo-3,4-dihydro -2H-benzo[1,4]thiazin-6-yl)-oxazolidin-5-ylmethyl]-amino}-methyl)-1,2-dihydro-pyrrolo [3,2,1-ij]quinolin-4-one;
- -8-fluoro-6-{2-[2-oxo-3-(3-oxo-3,4-dihydro-2H-benzo[1,4]thiazin-6-yl)-oxazolidin-5-yl]-ethylamino}-6,7-dihydro-5H-pyrido[3,2,1-ij]quinolin-3-one;
- -(R)-9-fluoro-2-({[(R)-2-oxo-3-(3-oxo-3,4-dihydro-2H-benzo[1,4]oxazin-6-yl)-oxazolidin-5-ylmethyl]-amino}-methyl)-1,2-dihydro-pyrrolo[3,2,1-ij]quinolin-4-one;
- -9-fluoro-2-({[(R)-2-oxo-3-(3-oxo-3,4-dihydro-2H-benzo[1,4]thiazin-6-yl)-oxazolidin-5-ylmethyl]amino}-methyl)-1,2-dihydro-pyrrolo [3,2,1-ij]quinolin-4-one ;
- -(R)-9-fluoro-2-({2-[2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;
- -2-({[(R)-2-oxo-3-(3-oxo-3,4-dihydro-2H-benzo[1,4]thiazin-6-yl)-oxazolidin-5-ylmethyl]-amino}-methyl)-2,3-dihydro-1 -oxa-3a-aza-phenalen-4-one;
- -9-fluoro-2-({[(R)-2-oxo-3-(3-oxo-3,4-dihydro-2H-benzo[1,4]thiazin-6-yl)-oxazolidin-5-ylmethyl]-amino}-methyl)-2,3-dihydro-1-oxa-3a-aza-phenalen-4-one;
- -3-fluoro-5-({[(R)-2-oxo-3-(3-oxo-3,4-dihydro-2H-benzo[1,4]thiazin-6-yl)-oxazolidin-5-ylmethyl]-amino}-methyl)-5,6-dihydro-4H-1,6a-diaza-phenalen-7-one;

- 3-fluoro-5-({[(R)-2-oxo-3-(3-oxo-3,4-dihydro-2H-benzo[1,4]oxazin-6-yl)-oxazolidin-5-ylmethyl]-amino}-methyl)-5,6-dihydro-4H-1,6a-diaza-phenalen-7-one;
- 3-fluoro-5-({2-[(R)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;
- (S)-9-fluoro-2-({[(R)-2-oxo-3-(3-oxo-3,4-dihydro-2H-benzo[1,4]oxazin-6-yl)-oxazolidin-5-ylmethyl]-amino}-methyl)- 1,2-dihydro-pyrrolo[3,2,1-ij]quinolin-4-one;
- (S)-9-fluoro-2-({2-[(R)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;
- (R)-9-fluoro-2-({2-[(R)-2-oxo-3-(3-oxo-3,4-dihydro-2H-benzo[1,4]thiazin-6-yl)-oxazolidin-5-yl]-ethylamino}-methyl)- 1,2-dihydro-pyrrolo[3,2,1-ij]quinolin-4-one;
- (S)-9-fluoro-2-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;
- (R)-9-fluoro-2-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;
- 9-fluoro-2-({2-[(R)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1 -ij]quinolin-4-one;
- 9-fluoro-2-{2-[(S)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1 -ij]quinolin-4-one;
- 9-fluoro-2-({2-[(R)-2-oxo-3-(3-oxo-3,4-dihydro-2H-benzo[1,4]oxazin-6-yl-oxazolidin-5-yl]-ethylamino}-methyl)-1,2,5,6-tetrahydro-pyrrolo[3,2,1-ij]quinolin-4-one;
- 5-({2-[(R)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;
- 5-({2-[(S)-2-oxo-3-(3-oxo-3,4-dihydro-2H-benzo[1,4]oxazin-6-yl)-oxazolidin-5-yl]-ethylamino}-methyl)-4,5-dihydro-pyrrolo[3,2,1-de][1,5]naphthyridin-7-one;
- 2-({2-[(R)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;
- 2-({2-[(R)-2-oxo-3-(3-oxo-3,4-dihydro-2H-benzo[1,4]oxazin-6-yl)-oxazolidin-5-yl]-ethylamino}-methyl)-1,2-dihydro-pyrrolo [3,2,1-ij]quinolin-4-one;
- 2-({[(R)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one;
- (S)-5-({2-[(S)-2-oxo-3-(3-oxo-3,4-dihydro-2H-benzo[1,4]thiazin-6-yl)-oxazolidin-5-yl]-ethylamino}-methyl)-5,6-dihydro-pyrrolo[1,2,3-de]quinoxalin-3-one;
- (S)-5-({[(R)-2-oxo-3-(3-oxo-3,4-dihydro-2H-benzo[1,4]thiazin-6-yl)oxazolidin-5-ylmethyl]-amino}-methyl)-5,6-dihydro-pyffolo[1,2,3-de]quinoxalin-3-one; or
- 5-({2-[(S)-2-oxo-3-(3-oxo-3,4-dihydro-2H-pyrido[3,2-b][1,4]oxazin-6-yl)-oxazolidin-5-yl]-ethylamino}-methyl)-5,6-dihydro-pyrrolo[1,2,3-de]quinoxalin-3-one;

or a salt of such a compound.

11. A pharmaceutical composition comprising, as active principle, a compound of formula I as defined in claim 1, or a pharmaceutically acceptable salt thereof, and at least one therapeutically inert excipient.

12. A method for treating a bacterial infection comprising administering a compound of formula I as defined in claim 1, or a pharmaceutically acceptable salt thereof, to a subject in need thereof.

13. A composition comprising the compound of formula I as defined in claim 1, or a pharmaceutically acceptable salt thereof, in an amount effective to treat or prevent a bacterial infection and at least one therapeutically inert excipient.

14. A compound of formula $I_{P1}$ according to claim 2, wherein W represents CH;
or a salt of such a compound.

15. A compound of formula $I_{P1}$ according to claim 2, wherein W represents N;
or a salt of such a compound.

16. A compound of formula $I_{P1}$ according to claim 2, wherein $R^1$ represents F;
or a salt of such a compound.

17. A compound of formula $I_{P1}$ according to claim 2, wherein U represents O;
or a salt of such a compound.

18. A compound of formula $I_{P1}$ according to claim 2, wherein U represents $CH_2$;
or a salt of such a compound.

19. A compound of formula $I_{P1}$ according to claim 2, wherein G represents the group $G^1$ and Z represents CH;
or a salt of such a compound.

20. A compound of formula $I_{P1}$ according to claim 2, wherein G represents the group $G^2$ or $G^{2t}$;
or a salt of such a compound.

21. A pharmaceutical composition comprising a compound of formula $I_{P1}$ as defined in claim 2, or a pharmaceutically acceptable salt thereof, and at least one therapeutically inert excipient.

22. A method for treating a bacterial infection comprising administering a compound of formula $I_{P1}$ as defined in claim 2, or a pharmaceutically acceptable salt thereof, to a subject in need thereof.

* * * * *